United States Patent
Jeffery et al.

(10) Patent No.: US 10,086,021 B2
(45) Date of Patent: *Oct. 2, 2018

(54) COMPOSITIONS COMPRISING BACTERIAL STRAINS

(71) Applicant: 4D PHARMA PLC, Leeds (GB)

(72) Inventors: Ian Jeffery, Cork (IE); Fergus Shanahan, Kinsale (IE); Paul O'Toole, Cork (IE); Alex Stevenson, Leeds (GB); Imke Mulder, Aberdeen (GB); Helene Savignac, Leeds (GB)

(73) Assignee: 4D Pharma PLC (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/915,889

(22) Filed: Mar. 8, 2018

(65) Prior Publication Data

US 2018/0207208 A1    Jul. 26, 2018

Related U.S. Application Data

(63) Continuation of application No. PCT/GB2017/053722, filed on Dec. 12, 2017.

(30) Foreign Application Priority Data

Dec. 12, 2017 (GB) .................................. 1621123.7

(51) Int. Cl.
| | | |
|---|---|---|
| *A61K 9/00* | (2006.01) | |
| *A61K 31/04* | (2006.01) | |
| *A61K 9/19* | (2006.01) | |
| *A61K 35/74* | (2015.01) | |
| *A61P 1/00* | (2006.01) | |
| *A61K 9/48* | (2006.01) | |
| *A61K 35/00* | (2006.01) | |

(52) U.S. Cl.
CPC ................ *A61K 35/74* (2013.01); *A61K 9/19* (2013.01); *A61K 9/48* (2013.01); *A61P 1/00* (2018.01); *A61K 2035/11* (2013.01)

(58) Field of Classification Search
CPC .......... A61K 2300/00; A61K 2039/505; A61K 31/194; A61K 21/215; A61K 31/708; A61K 2039/507; A61K 45/06; A61K 35/747; C07K 16/244; C07K 2317/76; C07K 2317/92; C07K 16/468; C07K 2317/33; C07K 2317/24; C07K 2317/31; C07K 2317/52; C07K 2317/55; C07K 2317/56; C07K 2317/565; C07K 2317/567; C07K 2317/622; C07K 2317/73; C07K 2319/30; C07K 14/47
See application file for complete search history.

(56) References Cited

U.S. PATENT DOCUMENTS

| | | |
|---|---|---|
| 5,589,168 A | 12/1996 | Allen et al. |
| 6,348,452 B1 | 2/2002 | Brown et al. |
| 6,645,530 B1 | 11/2003 | Borody |
| 7,749,494 B2 | 7/2010 | Renaud et al. |
| 7,998,474 B2 | 8/2011 | Kelly |
| 8,460,648 B2 | 6/2013 | Borody |
| 9,011,834 B1 | 4/2015 | McKenzie et al. |
| 9,314,489 B2 | 4/2016 | Kelly et al. |
| 9,539,293 B2 | 1/2017 | Kelly et al. |
| 9,610,307 B2 | 4/2017 | Berry et al. |
| 9,662,381 B2 | 5/2017 | Honda et al. |
| 9,796,762 B2 | 10/2017 | Kelly et al. |
| 9,808,519 B2 | 11/2017 | Honda et al. |
| 9,839,655 B2 | 12/2017 | Mulder et al. |
| 2003/0147858 A1 | 8/2003 | Renaud et al. |
| 2008/0069861 A1 | 3/2008 | Brown et al. |
| 2010/0247489 A1 | 9/2010 | Saur-Brosch |
| 2010/0284973 A1 | 11/2010 | Schiffer-Mannioui et al. |
| 2010/0303782 A1 | 12/2010 | Cobb et al. |
| 2010/0311686 A1 | 12/2010 | Kasper et al. |
| 2010/0316617 A1* | 12/2010 | Renaud ................ A61K 35/742 424/93.41 |
| 2014/0037716 A1 | 2/2014 | Nowill et al. |
| 2014/0147425 A1 | 5/2014 | Henn et al. |
| 2014/0154218 A1 | 6/2014 | Kohno et al. |
| 2014/0199281 A1 | 7/2014 | Henn et al. |
| 2014/0335131 A1 | 11/2014 | Mazmanian et al. |
| 2014/0341921 A1 | 11/2014 | Honda et al. |
| 2015/0071957 A1 | 3/2015 | Kelly et al. |
| 2015/0104418 A1 | 4/2015 | Flint et al. |
| 2016/0067188 A1 | 3/2016 | Cade et al. |

(Continued)

FOREIGN PATENT DOCUMENTS

| | | |
|---|---|---|
| CN | 101590081 A | 12/2009 |
| CN | 102940652 A | 2/2013 |

(Continued)

OTHER PUBLICATIONS

4D Pharma:"4Dpharma PLC clinical update on blautix (TM), a novel treatment to irritable bowel syndrome," 4DPharma, Jan. 19, 2016, XP002769874, Retrieved from: https://www.directorstalkinterviews.com/4d-pharma-plc-clinical-update-on-blautix-a-novel-treatment-for-irritable-bowel-syndrome/412689588. [Retrieved on May 5, 2017].

(Continued)

*Primary Examiner* — Padmavathi Baskar
(74) *Attorney, Agent, or Firm* — Wilson Sonsini Goodrich & Rosati

(57) ABSTRACT

Provided are compositions comprising a bacterial strain of the genus *Blautia*, for use in a method of increasing the microbiota diversity and/or inducing stability of the microbiota of a subject.

17 Claims, 41 Drawing Sheets

Specification includes a Sequence Listing.

(56) References Cited

U.S. PATENT DOCUMENTS

| | | | |
|---|---|---|---|
| 2016/0184370 A1 | 6/2016 | McKenzie et al. |
| 2016/0199424 A1 | 7/2016 | Berry et al. |
| 2016/0279177 A1 | 9/2016 | Kelly et al. |
| 2017/0143772 A1 | 5/2017 | Mulder et al. |
| 2017/0143773 A1 | 5/2017 | Mulder et al. |
| 2017/0143774 A1 | 5/2017 | Mulder et al. |
| 2017/0143775 A1 | 5/2017 | Mulder et al. |
| 2017/0173089 A1 | 6/2017 | Kelly |
| 2017/0319634 A1 | 11/2017 | Grant et al. |
| 2017/0326184 A1 | 11/2017 | Patterson et al. |
| 2017/0326202 A1 | 11/2017 | Kelly |
| 2017/0354695 A1 | 12/2017 | Grant et al. |
| 2017/0360856 A1 | 12/2017 | Grant et al. |
| 2017/0368110 A1 | 12/2017 | Grant et al. |

FOREIGN PATENT DOCUMENTS

| | | |
|---|---|---|
| CN | 103156888 A | 6/2013 |
| CN | 103981115 A | 8/2014 |
| CN | 102940652 B | 3/2015 |
| CN | 104546932 A | 4/2015 |
| CN | 104546933 A | 4/2015 |
| CN | 104546934 A | 4/2015 |
| CN | 104546935 A | 4/2015 |
| CN | 104546940 A | 4/2015 |
| CN | 104546942 A | 4/2015 |
| DE | 19826928 A1 | 12/1999 |
| EP | 0778778 A1 | 6/1997 |
| EP | 1448995 A1 | 8/2004 |
| EP | 2687227 A1 | 1/2014 |
| EP | 2810652 A2 | 12/2014 |
| EP | 2832859 A1 | 2/2015 |
| JP | H08259450 A | 10/1996 |
| JP | 2003261453 A | 9/2003 |
| JP | 2005097280 A | 4/2005 |
| JP | 2007084533 A | 4/2007 |
| JP | 2007116991 A | 5/2007 |
| JP | 2009507023 A | 2/2009 |
| JP | 2013527240 A | 6/2013 |
| JP | 2015500792 A | 1/2015 |
| KR | 20100128168 A | 12/2010 |
| WO | WO-9720577 A1 | 6/1997 |
| WO | WO-9855131 A1 | 12/1998 |
| WO | WO-9919459 A1 | 4/1999 |
| WO | WO-0185187 A1 | 11/2001 |
| WO | WO-0207741 A1 | 1/2002 |
| WO | WO-03046580 A1 | 6/2003 |
| WO | WO-2007027761 A2 | 3/2007 |
| WO | WO-2007136719 A2 | 11/2007 |
| WO | WO-2009027753 A1 | 3/2009 |
| WO | WO-2009072889 A1 | 6/2009 |
| WO | WO-2009154463 A2 | 12/2009 |
| WO | WO-2011110918 A1 | 9/2011 |
| WO | WO-2011149335 A1 | 12/2011 |
| WO | WO-2011152566 A2 | 12/2011 |
| WO | WO-2011153226 A2 | 12/2011 |
| WO | WO-2012024638 A2 | 2/2012 |
| WO | WO-2011153226 A3 | 3/2012 |
| WO | WO-2012142605 A1 | 10/2012 |
| WO | WO-2013008039 A2 | 1/2013 |
| WO | WO-2013037068 A1 | 3/2013 |
| WO | WO-2013050792 A1 | 4/2013 |
| WO | WO-2013080561 A1 | 6/2013 |
| WO | WO-2014001368 A1 | 1/2014 |
| WO | WO-2014067976 A1 | 5/2014 |
| WO | WO-2014075745 A1 | 5/2014 |
| WO | WO-2014078911 A1 | 5/2014 |
| WO | WO-2014121298 A2 | 8/2014 |
| WO | WO-2014121304 A1 | 8/2014 |
| WO | WO-2014137211 A1 | 9/2014 |
| WO | WO-2014145958 A2 | 9/2014 |
| WO | WO-2014150094 A1 | 9/2014 |
| WO | WO-2014167338 A1 | 10/2014 |
| WO | WO-2014201037 A2 | 12/2014 |
| WO | WO-2015006355 A2 | 1/2015 |
| WO | WO-2015013214 A2 | 1/2015 |
| WO | WO-2015021936 A1 | 2/2015 |
| WO | WO-2015095241 A2 | 6/2015 |
| WO | WO-2015156419 A1 | 10/2015 |
| WO | WO-2015156519 A1 | 10/2015 |
| WO | WO-2015169944 A1 | 11/2015 |
| WO | WO-2016019506 A1 | 2/2016 |
| WO | WO-2016057671 A1 | 4/2016 |
| WO | WO-2016086161 A1 | 6/2016 |
| WO | WO-2016086206 A1 | 6/2016 |
| WO | WO-2016086209 A1 | 6/2016 |
| WO | WO-2016102950 A1 | 6/2016 |
| WO | WO-2016102951 A1 | 6/2016 |
| WO | WO-2016203218 A1 | 12/2016 |
| WO | WO-2017091753 A1 | 6/2017 |
| WO | WO-2017148596 A1 | 9/2017 |
| WO | WO-2018011594 A1 | 1/2018 |

OTHER PUBLICATIONS

"Amedei, A. et al. Multiple sclerosis: the role of cytokines in pathogenesis and in therapies. Int J Mol Sci. Oct. 19, 2012;13(10):13438-60. doi: 10.3390/ijms131013438."

Arenberg, et al., Interferon-y-inducible Protein 10 (IP-10) Is an Angiostatic Factor That Inhibits Human Non-small Cell Lung Cancer (NSCLC) Tumorigenesis and Spontaneous Metastases. 1996. J. Exp.Med. 184:981-92.

Atarashi et al., Th17 Cell Induction by Adhesion of Microbes to Intestinal Epithelial Cells. Cell, vol. 163, No. 2, Oct. 8, 2015. pp. 367-380.

Atarashi, K. et al., Treg induction by a rationally selected mixture of Clostridia strains from the human microbiota. Nature. 2013; 500(7461):232-236.

Atlas, R. Handbook of Microbiological Media, Fourth Edition. CRC Press. 2010.

Ausubel, et al. Current Protocols in Molecular Biology. 1987. Supplement 30.

Ausubel et al., Short protocols in molecular biology. Fifth edition, 2002.

Azad, M.B. et al., Probiotic supplementation during pregnancy or infancy for the prevention of asthma and wheeze: systematic review and meta-analysis BMJ 2013; 347 :f6471.

Bagge, et al., Diversity of spore-forming bacteria in cattle manure, slaughterhouse waste and samples from biogas plants. Journal of applied microbiology. 2010;109: 1549-1565.

Balato, et al., Effects of adalimumab therapy in adult subjects with moderate-to-severe psoriasis on Th17 pathway. (2014) J Eur Acad Dermatol Venereol. 28(8):1016-24.

Banfield, J. & Murphy, K.R., Non-Th2, Late-onset, non-allergic asthma. Copd & Asthma for NPs, A peer-reviewed newsletter, Aug. 2016; 14: 8 Pages.

Berger, S. Gideon guide to medically important bacteria. Gideon E-book Series. 2017 edition. 4 pages.

Bernalier et al. *Ruminococcus hydrogenotrophicus* sp. nov., a new H2/CO2-utilizing acetogenic bacterium isolated from human feces. 1996 Arch. Microbiol. 166 (3), 176-183.

Bertram, J. et al. Establishment of a cloned line of Lewis lung carcinoma cells adapted to cell culture. (1980) Cancer let. 11:63-73.

Birdi, K.S. Handbook of Surface and Colloid Chemistry, 2nd Edition. CRC Press. 1997.

Bottacini, et al., Comparative genomics of the Bifidobacterium brevetaxon. BMC Genomics, 2014; 15:170. DOI:10.1186/1471-1471-2164-15-170.

Brand et al., Collagen-induced arthritis, 2007; Protocol 2(5):1269-1275.

Busing, K. et al., Effects of oral *Enterococcus faecium* strain DSM 10663 NCIMB 10415 on diarrhoea patterns and performance of sucking piglets. Benef Microbes. Mar. 2015;6(1):41-4. doi: 10.3920/BM2014.0008.

"Campeau, J.L. et al., Intestinal Epithelial Cells Modulate Antigen-Presenting Cell Responses to Bacterial DNA. Infectionand Immunity. Aug. 2012; 80(8): 2632-2644."

(56) References Cited

OTHER PUBLICATIONS

Caspi, P.R. Experimental autoimmune uveoretinitis in the rat and mouse. Curr Protoc Immunol. May 2003;Chapter 15:Unit 15.6. doi: 10.1002/0471142735.im1506s53.

Cekanaviciute, et al., Gut bacteria from multiple sclerosis patients modulate human T cells and exacerbate symptoms in mouse models. PNAS. Jun. 30, 2017; 1-6.

Charriot, et al., Future treatment for ashtma, Eur Respir Rev 2016; 25: 77-92.

Cheluvappa, R. et al., T helper type 17 pathway suppression by appendicitis and appendectomy protects against colitis. Clin Exp Immunol. Feb. 2014;175(2):316-22. doi: 10.1111/cei.12237.

Chen, S. et al., Live combined bacillus subtilis and *Enterococcus faecium* ameliorate murine experimental colitis by immunosuppression. International journal of inflammation. 2014(878054). 7 pages.

Chi, W. et al., IL-23 promotes CD4+ T cells to produce IL-17 in Vogt-Koyanagi-Harada disease. J Allergy Clin Immunol. May 2007;119(5):1218-24. Epub Mar. 1, 2007.

Chi, W. et al. Upregulated IL-23 and IL-17 in Behcet patients with active uveitis. Invest Ophthalmol Vis Sci. Jul. 2008;49(7):3058-64. doi: 10.1167/iovs.07-1390.

Chiu, et al., Monocolonization of germ-free mice with bacteroides fragilis protects against dectran sulfate sodium-induced acute colitis. Biomed Research International 2014. vol. 2014. Article ID 675786. 9 Pages.

Claesson, et al. Gut microbiota composition correlates with diet and health in the elderly. 2012. Nature, 488, 178-184.

Collins, M.D., et al., *Enterococcus avium* nom. rev., comb. nov.; *E. casseliflavus* nom. rev., comb. nov.; *E. durans* nom. rev., comb. nov.; *E. gallinarum* comb. nov.; and *E. malodoratus* sp. nov. (1984) Int J Syst Evol Microbiol. 34: 220-223.

Colowick, S. and Kaplan, N., Methods of Enzymology. Academic Press, Inc.

Constantinescu et al. Experimental autoimmune encephalomyelitis (EAE) as a model for multiple sclerosis (MS). 2011. Br J Pharmacol. 164(4):1079-1106.

Co-pending U.S. Appl. No. 15/704,245, filed Sep. 14, 2017.
Co-pending U.S. Appl. No. 15/803,721, filed Nov. 3, 2017.
Co-pending U.S. Appl. No. 15/803,723, filed Nov. 3, 2017.
Co-pending U.S. Appl. No. 15/842,635, filed Dec. 14, 2017.
Co-pending U.S. Appl. No. 15/915,885, filed Mar. 8, 2018.
Co-pending U.S. Appl. No. 15/916,167, filed Mar. 8, 2018.
Co-pending U.S. Appl. No. 15/916,202, filed Mar. 8, 2018.
Co-pending U.S. Appl. No. 15/916,205, filed Mar. 8, 2018.

Dahya V. et al., Clostridium ramosum Osteomyelitis in an immunocompetent patient after traumatic injury, Infectious Diseases in Clinical Practice 20150312 Lippincott Williams and Wilkins USA, vol. 23, No. 2, Mar. 12, 2015, pp. 102-104, XP009193312, ISSN: 1056-9103 the whole document.

Darfeuille-Michaud et al. High prevalence of adherent-invasive *Escherichia coli* associated with ileal mucosa in Crohn's disease. .2004. Gastroenterology 127(2):412-21.

Darlington, G.J., Liver Cell Lines. (1987) Meth Enzymol. 151:19-38.

Day, J.G. et al., Cryopreservation and Freeze-Drying Protocols. Springer. 2007. 2nd edition.

Demarche, et al., Detailed analysis of sputum and systemic inflammation in asthma phenotypes: are paucigranulocytic asthmatics really non-inflammatory?, BMC Pulmonary Medicine, 2016; (16)46: 1-13.

Distrutti, et al., Gut Microbiota role in irritable bowel syndrome: New therapeutic strategies. World Journal of Gastroenterology. Feb. 21, 2016; 22(7): p. 2219-2241, XP002769875.

Divyashri et al. Probiotic attributes, antioxidant, anti-inflammatory and neuromodulatory effects of *Enterococcus faecium* CFR 3003: in vitro and in vivo evidence. (2015) J Med Microbiol. doi: 10.1099/jmm.0.000184.

Duncan et al. (2002) "*Roseburia intestinal is* sp. nov., a novel saccharolytic, butyrate-producing bacterium from human faeces," International Journal System Evolutionary Microbiology. 52:1615-1620.

Duncan et al. (2006) "Proposal of *Roseburia faecis* sp. nov., *Roseburia hominis* sp. nov. and *Roseburia inulinivorans* sp. nov., based on isolates from human faeces," International Journal of Systematic and Evolutionary Microbiology. vol. 56, No. Pt 10, pp. 2437-2441.

Eckburg, PB. et al., Diversity of the human intestinal microbial flora.Science. Jun. 10, 2005;308(5728):1635-8. Epub Apr. 14, 2005.

Fabro, A. et al., The Th17 pathway in the peripheral lung microenvironment interacts with expression of collagen V in the late state of experimental pulmonary fibrosis. (2015) Immunobiology. 220(1):124-35.

Faghih, Z. et a., IL-17 and IL-4 Producing CD8+ T Cells in Tumor Draining Lymph Nodes of Breast Cancer Patients: Positive Association with Tumor Progression. (2013). Iranian Journal of Immunology. 10(4):193-204.

Fahy, J.V. Eosinophilic and neutrophilic inflammation in asthma: insights from clinical studies. Proc Am Thorac Soc. May 1, 2009;6(3):256-9. doi: 10.1513/pats.200808-087RM.

Faith et al. The long-term stability of the human gut microbiota. 2013. Science, 341(6141): 1237439.

Farooq, P.D. et al., Pseudomembranous colitis, Disease-A-Month 2015 Mosby Inc. USA, vol. 61, No. 5, May 1, 2015, pp. 181-206, XP009193313, ISSN: 0011-5029 p. 195.

FDA Orphan Drug Designations. Total Orphan Drugs website. Aug. 2014. Available at http://www.orphan-drugs.org/2014/09/01/fda-orphandrug- designations-august-2014. Accessed on Apr. 13, 2016.

Fenner, et al., *Bacteroides massiliensis* sp. nov., isolated from blood culture of a newborn. International Journal of systematic and evolutionary microbiology, 2005. 55: 1335-1337.

Frank, D. et al., Molecular-phylogenetic characterization of microbial community imbalances in human inflammatory bowel diseases. 2007. PNAS. 104(34):13780-5.

GB Exam and search report dated Aug. 30, 2016 for GB Application No. 1520638.6.

GB Search and Exam report dated Mar. 31, 2016 for GB application 1510469.8.

GB Search and Exam report dated Mar. 31, 2016 for GB application 1510470.6.

GB Search and Exam report dated Apr. 15, 2016 for GB application 1510467.2.

GB Search and Exam report dated Apr. 20, 2016 for GB application 1510466.4.

GB Search and Exam report dated Apr. 20, 2016 for GB application 1510468.0.

GB Search and Exam report dated Aug. 30, 2016 for GB application No. 1520631.1.

GB Search and Exam report dated Nov. 17, 2016 for GB application 1520502.4.

GB Search and Exam report dated Sep. 13, 2016 for GB application 1520497.7.

Gennaro, A.R. "Quality Assurance and Control," from Remington: The Science and Practice of Pharmacy, 2000, Lippincott Williams & Wilkins, 20th ed., pp. 980-983.

Gennaro, A.R., Remington's Pharmaceutical sciences, Mack publishin co. 1985.

Ghadimi, D. et al., Epigenetic imprinting by commensal probiotics inhibits the IL-23/IL-17 axis in an in vitro model of the intestinal mucosal immune system. JLB. 2012;92(4):895-911.

Goldin, B.R. et al., Clinical indications for probiotics: an overview. Clin Infect Dis. Feb. 1, 2008;46 Suppl 2:S96-100; discussion S144-51. doi: 10.1086/523333.

Guide for the care and use of laboratory animals: 8th edition. The national academic press; 2011.

Haabeth et al. A model for cancer-suppressive inflammation. (2012) OncoImmunology 1(1):1146-1152.

Hammerich, L. et al., Interleukins in chronic liver disease: lessons learned from experimental mouse models. (2014) Clin Exp Gastroenterol. 7:297-306.

(56) References Cited

OTHER PUBLICATIONS

Handbook of Experimental Immunology, vol. I IV (D.M. Weir and C.C. Blackwell, eds, 1986, Blackwell Scientific Publications).
International search report with written opinion dated Feb. 26, 2018 for PCT/GB2017/053722.
Hansen, et al., The role of mucosal immunity and host genetics in defining intestinal commensal bacteria. 2010. Curr. Opin. Gastroenterol., 26(6): 564-571.
Holdeman, et al., *Eubacterium contortum* (*Prevot*) comb. nov.: Emendation of description and designation of the type strain. International journal of systematic bacteriology. Oct. 1971;21(4): 304-306.
Hougee, et al., Oral treatment with probiotics reduces allergic symptoms in ovalbumin-sensitized mice:a bacterial strain comparative study. Int Arch Allergy Immunol. 2010; 151:107-117.
International Search Report dated Jan. 27, 2017 for International Application No. PCT/GB2016/053622.
International Search Report dated Feb. 17, 2017 for International Application No. PCT/GB2016/053676.
International Search Report dated Aug. 26, 2016 for International application No. PCT/GB2016/051774.
International Search Report dated Aug. 26, 2016 for International application No. PCT/GB2016/051776.
International Search Report dated Sep. 6, 2016 for International application No. PCT/GB2016/051768.
International Search Report dated Sep. 6, 2016 for International application No. PCT/GB2016/051773.
International Search Report dated Sep. 6, 2016 for International application No. PCT/GB2016/051770.
International Search Report dated Feb. 2, 2017 for International application No. PCT/GB2016/053620.
International Search Report dated Mar. 6, 2017 for International Application No. PCT/GB2016/053677.
International search report with written opinion dated Jun. 8, 2017 for GB Application No. 1616016.
International search report with written opinion dated Sep. 29, 2017 for GB Application No. 1621123.
International search report with written opinion dated Oct. 16, 2017 for PCT/GB2017/052076.
Ispirli, H. et al., Characterization of functional properties of *Enterococcus faecium* strains isolated from human gut.Can. J. Microbiol. 61: 861-870 (2015) dx.doi.org/10.1139/cjm-2015-0446.
Jawad, S. et al., Elevated serum levels of interleukin-17A in uveitis patients. Ocul Immunol Inflamm. Dec. 2013;21(6):434-9. doi: 10.3109/09273948.2013.815786. Epub Aug. 19, 2013.
Jiao et al., Blockade of Notch Signaling Ameliorates Murine Collagen-Induced Arthritis via Suppressing Th1 and Th17 Cell Responses. 2014; Pathology, 184(4):1085-1093.
Kailasapathy, K. Microencapsulation of Probiotic Bacteria:Technology and Potential Applications. Curr. Issues Intest. Microbiol. (2002) 3: 39-48.
Kanauchi, et al., Eubacterium limosum ameliorates experimental colitis and metabolite of microbe attenuates colonic inflammatory action with increase of mucosal integrity introduction, China World J Gastroenterol February, Jan. 1, 2006. pp. 1071-1077.
Kanauchi, et al., Eubacterium limosum (probiotic) and its metabolites showed anti-inflammatory effects and increased mucosal barrier function in colitis. S1912.
Kang, S. et al., Dysbiosis of fecal microbiota in Crohn's disease patients as revealed by a custom phylogenetic microarray.Inflamm Bowel Dis. Dec. 2010;16(12):2034-42. doi: 10.1002/ibd.21319.
Karaffova, et al., Interaction of TGF-B4 and IL-17 with IgA secretion in the intestine of chickens fed with E. faecium AL41 and challenged with S. Enteritidis. Research in Veterinary science. 2015:75-79.
Karin, M. Nuclear factor-kappaB in cancer development and progression. Nature. May 25, 2006;441(7092):431-6.
Kitahara, M. et al., *Bacteroides plebeius* sp. nov. and *Bacteroides coprocola* sp. nov., isolated from human faeces. International journal of systematic and evolutionary microbiology. 2005; 55: 2143-2147.
Koenders, M.I. et al., Interleukin-17 Acts Independently of TNF-a under Arthritic Conditions. (2006) J. Immunol. 176:6262-6269.
Kverka, M. et al., Oral administration of Parabacteroides distasonis antigens attenuates experimental murine colitis through modulation of immunity and microbiota composition. Clinical & Experimental Immunology. 2010; 163:250-259.
Laukova, A. et al. Benefits of Combinative Application of Probiotic, Enterocin M-Producing Strain *Enterococcus faecium* AL41 and Eleutherococcus Senticosus in Rabbits. Folia Microbiol (Praha) 61 (2), 169-177. Sep. 9, 2015.
Lee, et al. Intestinal microbiota in pathophysiology and management of irritable bowel syndrome . 2014. World J Gastroenterol. 20(27): 8886-8897.
Lejeune, FJ. et al., Efficiency of Recombinant Human TNF in Human Cancer Therapy. (2006) Cancer Immun. 6:6.
Leslie, et al., Trehalose and sucrose protect both membranes and proteins in intact bacteria during drying. (1995) Appl. Environ. Microbiol. 61, 3592-3597.
Liu et al. Reclassification of Clostridium coccoides, Ruminococcus hansenii, Ruminococcus hydrogenotrophicus, Ruminococcus luti, Ruminococcus productus and Ruminococcus schinkii as *Blautia coccoides* gen. nov., comb. nov., *Blautia hansenii* comb. nov., *Blautia hydrogenotrophica* comb. nov., *Blautia luti* comb. nov., *Blautia producta* comb. nov., *Blautia schinkii* comb. nov. and description of *Blautia wexlerae* sp. nov., isolated from human faeces. 2008. Int J Syst Evol Microbiol 58,1896-1902.
Lodemann, U. et al., Effects of the Probiotic *Enterococcus faecium* and pathogenic *Escherichia coli* strains in a pig and human epithelial intestinal cell model. Hindawi publishing corporation scientifica. 2015(235184) 10 pages.
Lopetuso et al. Commensal Clostridia: leading players in the maintenance of gut homeostasis. 2013. Gut Pathogens, 5: 23.
Lozupone. Diversity, stability and resilience of the human gut microbiota. 2012. Nature. Sep. 13, 2012; 489 (7415): 220-230.
Luger, D. and Caspi, R.R., New perspectives on effector mechanisms in uveitis. (2008) Semin. Immunopathol. 30(2): 134-143.
Lyons, et al., Bacterial strain-specific induction of Foxp3 T regulatory cells is protective in murine allergy models. Clinical & Experimental Allergy. 2010; 40:811-819.
Machiels, K. A decrease of the butyrate-producing species *Roseburia hominis* and *Faecalibacterium prausnitzii* defines dysbiosis in patients with ulcerative colitis.Gut. Aug. 2014;63(8):1275-83. doi: 10.1136/gutjnl-2013-304833. Epub Sep. 10, 2013.
MacPherson, AJ. et al., IgA responses in the intestinal mucosa against pathogenic and non-pathogenic microorganisms. Oct. 2001. 3(12). 1021-1035.
MacPherson, AJ., et al., The functions of mucosal T cells in containing the indigenous commensal flora of the intestine.Cell Mol Life Sci. Dec. 2002;59(12):2088-96.
MacSharry et al., Immunomodulatory effects of feeding with bifidobacterium longum on allergen-induced lung inflammation in the mouse. Pulmonary pharmacology & Therapeutics. 2012; 25:325-334.
Maintaining Cultures for Biotechnology and Industry (1996) Jennie C. Hunter-Cevera, Academic Press.
Manni et al., A tale of two cytokines: IL-17 and IL-22 in asthma and infection. Expert Rev Respir Med. Feb. 2014; 8(1): 25-42. doi:10.1586/17476348.2014.854167.
Mansour et al. Isolation of *Enterococcus faecium* NM113, *Enterococcus faecium* NM213 and Lactobacillus casei NM512 as novel probiotics with immunomodulatory properties. (2014) Microbiol Immunol. 58(10):559-69.
Masco, L., et al., Identification of *Bifidobacterium* Species Using rep-PCR Fingerprinting. Systematic and Applied Microbiology 26(4):557-63 • Dec. 2003.
Maya, J.R. et al., Emerging Therapies for Noninfectious Uveitis: What May Be Coming to the Clinics. (2014) J. Ophthalmology. 310329.

(56) References Cited

OTHER PUBLICATIONS

Mazmanian, SK., An immunomodulatory molecule of symbiotic bacteria directs maturation of the host immune system.Cell. Jul. 15, 2005;122(1):107-18.
Meyza, et al. The BTBR mouse model of idiopathic autism—Current view on mechanisms. 2017. Neurosci Biobehav Rev.;76(Pt A):99-110.
Miossec, P. et al. Targeting IL-17 and TH17 cells in chronic inflammation. Nat Rev Drug Discov. Oct. 2012;11(10):763-76. doi: 10.1038/nrd3794.
Mitropoulou, G. et al. Immobilization Technologies in Probiotic Food Production. (2013) Journal Nutr Metab. (2013) 716861.
Miyake, T. et al., Phylogenetic Analysis of the Genus *Bifidobacterium* and Related Genera Based on 16S rDNA Sequences. Microbiol. Immunol. 1998; 42(10):661-667.
Miyamoto-Shinohara et al. Survival of freeze-dried bacteria. J Gen Appl Microbiol 54(1):9-24 (2008).
Miyauchi, E., Control of multiple sclerosis by gut microbiota. Journal of clinical and experimental medicine. 2015. vol. 253 No. 5.2, pp. 445-450.
Molecular Biology Techniques: An Intensive Laboratory Course, (Ream et al., eds., 1998, Academic Press).
Monteleone, I. et al., Th17-related cytokines: new players in the control of chronic intestinal inflammation. (2011) BMC Medicine. 2011, 9:122.
Mucientes, A. et al., Specific association of IL17A genetic variants with panuveitis. (2015) Br J Ophthalmol. 99(4):566-70.
Mukai et al., SH3BP2 Gain-of-Function Mutation Exacerbates Inflammation and Bone Loss in a Murine Collagen-Induced Arthritis Model, 2014 PLoS One 9(8): e105518.
Narushima, et al., Characterization of the 17 strains of regulatory T cell-inducing human-derived Clostridia. Gut Microbes Mar. 18, 2014; 5:3, 333-339.
Notice of allowance dated Sep. 1, 2017 for U.S. Appl. No. 15/357,850.
Notice of Allowance dated Nov. 22, 2017 for U.S. Appl. No. 15/359,988.
Numasaki, M. et al., IL-17 Enhances the Net Angiogenic Activity and In Vivo Growth of Human Non-Small Cell Lung Cancer in SCID Mice through Promoting CXCR-2-Dependent Angiogenesis. (2005) J. Immunol. 175: 6177-6189.
Numasaki, M. et al., Interleukin-17 promotes angiogenesis and tumor growth. Blood. Apr. 1, 2003;101(7):2620-7. Epub Oct. 31, 2002.
Office Action dated Jan. 2, 2018 for U.S. Appl. No. 15/357,936.
Office Action dated Jan. 11, 2005 for U.S. Appl. No. 10/285,224.
Office Action dated Jan. 26, 2009 for U.S. Appl. No. 10/275,706.
Office Action dated Feb. 18, 2010 for U.S. Appl. No. 10/285,224.
Office Action dated Mar. 13, 2013 for U.S. Appl. No. 12/760,926.
Office Action dated Mar. 26, 2007 for U.S. Appl. No. 10/275,706.
Office Action dated Apr. 4, 2008 for U.S. Appl. No. 10/285,224.
Office Action dated May 2, 2007 for U.S. Appl. No. 10/285,224.
Office Action dated May 2, 2008 for U.S. Appl. No. 10/275,706.
Office Action dated May 25, 2016 for U.S. Appl. No. 14/249,710.
Office Action dated May 26, 2009 for U.S. Appl. No. 10/285,224.
Office Action dated May 26, 2017 for U.S. Appl. No. 15/357,850.
Office Action dated May 30, 2006 for U.S. Appl. No. 10/285,224.
Office Action dated Jun. 26, 2017 for U.S. Appl. No. 15/357,936.
Office Action dated Jul. 6, 2017 for U.S. Appl. No. 15/070,605.
Office action dated Jul. 8, 2015 for U.S. Appl. No. 14/349,907.
Office Action dated Jul. 31, 2017 for U.S. Appl. No. 15/359,988.
Office Action dated Aug. 10, 2017 for U.S. Appl. No. 15/357,850.
Office Action dated Aug. 21, 2013 for U.S. Appl. No. 12/760,926.
Office Action dated Sep. 4, 2015 for U.S. Appl. No. 14/249,710.
Office Action dated Sep. 17, 2010 for U.S. Appl. No. 10/285,224.
Office Action dated Oct. 12, 2005 for U.S. Appl. No. 10/285,224.
Office Action dated Oct. 28, 2009 for U.S. Appl. No. 10/275,706.
Office Action dated Oct. 30, 2008 for U.S. Appl. No. 10/285,224.
Office Action dated Nov. 2, 2017 for U.S. Appl. No. 15/700,007.
Office Action dated Nov. 6, 2006 for U.S. Appl. No. 10/285,224.
Office Action dated Nov. 23, 2015 for U.S. Appl. No. 14/232,475.
Office Action dated Nov. 24, 2017 for U.S. Appl. No. 15/359,972.
Office Action dated Nov. 24, 2017 for U.S. Appl. No. 15/679,857.
Office Action dated Dec. 6, 2017 for U.S. Appl. No. 15/592,178.
Office Action dated Dec. 13, 2012 for U.S. Appl. No. 12/760,926.
Office Action dated Dec. 19, 2005 for U.S. Appl. No. 10/275,706.
Oladipo, et al., Bioprotective potential of bacteriocinogenic *Enterococcus gallinarum* strains isolated from some Nigerian fermented foods, and of their bacteriocins. Polish Journal of Microbiology. 2014; 63(4): 415-422.
Overstreet et al. 'Dysbiosis Characterized by Reduced Abundance of Roseburia is Associated With Increased Severity of Colitis in IL-10-/- Mice'. Gastroenterology. 2011, vol. 140, No. 5, Suppl. 1, pp. S-696.
Pace et al. Macrophage activiation: Priming activity from a T-cell hybridoma is attributable to interferon. (1983) PNAS. 80:3782-6.
Parabacteroides distasonis (Eggerth and Gagnon) Sakamoto and Benno (ATCC 8503). Sep. 19, 2017. 2 Pages.
Park, S.K. et al., *Blautia stercoris* sp. nov., isolated from human faeces. International journal of systematic and evolutionary microbiology. 2012; 62(4): 776-779.
Patel., R. et al., Determination of 16S rRNA sequences of enterococci and application to species identification of nonmotile *Enterococcus gallinarum* isolates. Journal of clinical microbiology, 1998; 36(11):3399-3407.
PCR (Introduction to Biotechniques Series), 2nd ed. (Newton & Graham eds., 1997, Springer Verlag).
PCT/EP2017/025038 Written Opinion of the International Preliminary Examining Authority dated Jan. 1, 2018.
Pearson, Wr. An introduction to sequence similarity ("Homology") searching. Current protocols in bioinformatics/editoral board, Andreas D Baxevanis. 2013; 0 3:10. 1002/0471250953. bi0301s42. doi:10. 1002/0471250953.bi0301542.
Petersen et al. Intestinal colonization with phylogenetic group B2 *Escherichia coli* related to inflammatory bowel disease: a systematic review and meta-analysis. 2015. Scand J Gastroenterol. ;50(10):1199-207.
Rajilic-Stojanovic, et al. The first 1000 cultures species of the human gastrointestinal micriobiota. FEMS MIcriobiol Rev, vol. 38, 2014. pp. 996-1047.
Remington. Remington: The science and practice of pharmacy. 20th Edition. Gennaro, Eds. Lippincott Williams & Wilkins, 2003.
Riquelme. Will 4D Pharma be UK's next Microbiome leader? Feb. 2, 2015, LABIOTECH.eu [online].
Robinson, et al. Inside information—The unique features of visceral sensation. 2008. Mol Interv, 8(5): 242-253.
Rockwell, S.C. et al., Characteristics of a Serially Transplanted Mouse Mammary Tumor and Its Tissue-Culture-Adapted Derivative. (1972) J Natl Cancer Inst. 49:735-49.
Sagar, et al., Bifidobacterium breve and lactobacillus rhamnosus treatment is as effective as budesonide at reducing inflammation in a murine model for chronic asthma. Respiratory Research. 2014; 15(46):1-17.
Sakamoto, M. et al., Reclassification of Bacteroides distasonis, Bacteroides goldsteinii and Bacteroides merdae as *Parabacteroides distasonis* gen. nov., comb. nov., *Parabacteroides goldsteinii* comb. nov. and *Parabacteroides merdae* comb. nov. International journal of systematic and evolutionary microbiology. 2006; 56: 1599-1605.
Salix Pharmaceuticals, Inc. FDA Highlights of Prescribing Information—XIFAXAN (rifaximin tablet). Revised Nov. 2015.
Sambrook, J.F. et al., Molecular Cloning: A Laboratory Manual, 3rd ed. Cold spring harbor laboratory press. 2001.
Scanlan PD., et al., Culture-independent analyses of temporal variation of the dominant fecal microbiota and targeted bacterial subgroups in Crohn's disease. J Clin Microbiol. Nov. 2006;44(11):3980-8. Epub Sep. 20, 2006.
Scher et al., Expansion of intestinal Prevotella copri correlates with enhanced susceptibility to arthritis. 2013; eLIFE 2, e01202, 20 Pages.
Schieck, M. et al., Genetic variation in TH17 pathway genes, childhood asthma, and total serum IgE levels.(2014) J Allergy Clin Immunol. 133(3):888-91.
Schleifer, K.H. et al., Transfer of *Streptococcus faecalis* and *Streptococcus faecium* to the Genus *Enterococcus* nom. rev. as *Enterococ-*

(56) References Cited

OTHER PUBLICATIONS cus faecalis comb. nov. and *Enterococcus faecium* comb. nov. Int J Syst Evol Microbiol, Jan. 1984 34: 31-34, doi:10.1099/00207713-34-1-31.

Schmitz, S. et al., A prospective, randomized, blinded, placebo-controlled pilot study on the effect of *Enterococcus faecium* on clinical activity and intestinal gene expression in canine food-responsive chronic enteropathy. J Vet Intern Med. Mar.-Apr. 2015;29(2):533-43. doi: 10.1111/jvim.12563. Epub Mar. 16, 2015.

Schouten, et al., Cow milk allergy symptoms are reduced in mice fed dietary synbiotics during oral sensitization with whey. Nutritional Immunology. 2015; 139(7):1390-403.

Schwiertz, et al., Quantification of Different *Eubacterium* spp. in Human Fecal Samples with Species-Specific 16S rRNA-Targeted Oligonucleotide Probes. Applied and environmental biology, vol. 66, No. 1, Jan. 1, 2000; pp. 375-382.

Severijnen, et al., Chronic Arthritis Induced in Rats by Cell Wall Fragments of *Eubacterium* Species from the Human Intestinal Flora. Infection and Immunity, Feb. 1990; 58(2): p. 523-528.

Sgadari, C. et al., Interferon-inducible protein-10 identified as a mediator of tumor necrosis in vivo. (1996) PNAS. 93:13791-6.

Sgadari et al. Mig, the Monokine Induced by Interferon-g, Promotes Tumor Necrosis In Vivo. (1997) Blood. 89:2635-43.

Shabgah, A.G. et al., Interleukin-17 in human inflammatory diseases. Postepy Dermatol Alergol. Aug. 2014; 31(4): 256-261.

Simpson-Herren, L. et al., Kinetic parameters and growth curves for experimental tumor systems. Cancer Chemother Rep. Jun. 1970;54(3):143-74.

Sisson, G. et al., Randomised clinical trial: a liquid multi-strain probiotic vs. placebo in the irritable bowel syndrome—a 12 week double-blind study. Aliment Pharmacol Ther. 2014; 40: 51-62.

Sivieri, K. et al., Probiotic *Enterococcus faecium* CRL 183 inhibit chemically induced colon cancer in male wistar rats. Eur Food Res Technol. 2008; 228:231-237.

Smith, T.F. et al., Comparison of biosequences. (1981) Adv. Appl. Math. 2: 482-489.

Song et al., Impact of Schistosoma japonicum Infection on Collagen-Induced Arthritis in DBA/1 Mice: A Murine Model of Human Rheumatoid Arthritis. 2011; PLoS One 6, e23453, 10 pAGES.

Spor, A. et al., Unravelling the effects of the environment and host genotype on the gut microbiome. Nat Rev Microbiol. Apr. 2011;9(4):279-90. doi: 10.1038/nrmicro2540.

Srutkova, D. et al., Efficiency of PCR-based methods in discriminating *Bifidobacterium longum* ssp. *longum* and *Bifidobacterium longum* ssp. *infantis* strains of human origin.J Microbiol Methods. Oct. 2011;87(1):10-6. doi: 10.1016/j.mimet.2011.06.014. Epub Jul. 2, 2011.

Stanton et al. (1983) "*Roseburia cecicola* gen. nov., sp. nov., a Motile, Obligately Anaerobic Bacterium from a Mouse Cecum," Int. J. Syst. Bacterial. 33:618-627.

Stoll et al., Altered microbiota associated with abnormal humoral immune responses to commensal organisms in enthesitis-related arthritis, 2014; Arthritis Res Ther. 16:486.

Strickertsson, J.A. et al., *Enterococcus faecalis* Infection and Reactive Oxygen Species Down-Regulates the miR-17-92 Cluster in Gastric Adenocarcinoma Cell Culture. Genes 2014, 5(3), 726-738.

Strobel, H.J. Basic laboratory culture methods for anaerobic bacteria. Methods Mol Biol. 2009;581:247-61. doi: 10.1007/978-1-60761-214-8_16.

Strus et al. Distinct effects of Lactobacillus plantarum KL3OB and *Escherichia coli* 3A1 on the induction and development of acute and chronic inflammation. 2015. Cent Eur J Immunol.40(4):420-30.

Sun, D. et al., The role of Th17-associated cytokines in the pathogenesis of experimental autoimmune uveitis (EAU). (2015) Cytokine. 74(1):76-80.

Tanaka, K. and Watanabe, K., In Vitro tebipenem activity against anaerobic bacteria. Japanese Journal of Chemotherapy. Mar. 2009. vol. 57 S-1.

Tap et al. Towards the human intestinal microbiota phylogenetic core. 2009. Environ Microbiol, 11(10):2574-84.

Tesmer, LA. et al., Th17 cells in human disease. Immunol Rev. 2008;223:87-113.

Toomer, O. et al., Maternal and postnatal dietary probiotic supplementation enhances splenic regulatory T helper cell population and reduces peanut allergen-induced hypersensitivity responses in mice. Immunobiology. 209; 2014: 661-670.

Tsukinowa, et al., Fecal microbiota of a dugong (*Dugong dugong*) in captivity at Toba Aquarium. J. Gen. Appl. Microbiol., 54, 25-38 (2008).

Turnbaugh et al. A core gut microbiome in obese and lean twins. Jan. 22, 2009. Nature, 457(7228): 480-484.

Udayappan, et al., Oral treatment with Eubacterium hallii improves insulin sensitivity in db/db mice. NPJ Biofilms and microbiomes, vol. 2, Jul. 6, 2016; p. 16009.

Udayappan et al., PS4-5. Administration of Eubacterium hallii improves insulin sensitivity and degree of liversteatosis in male db/db mice. Nederlands tijdschrift voor diabetologie, vol. 11, No. 4., Nov. 23, 2013.pp. 145.

U.S. Appl. No. 15/631,952 Office Action dated Feb. 16, 2018.
U.S. Appl. No. 15/679,857 Office Action dated Feb. 14, 2018.
U.S. Appl. No. 15/803,723 Notice of Allowance dated Feb. 13, 2018.

Van De Veerdonk, et al., The Anti-CD20 antibody rituximab reduces the Th17 cell response. Arthritis & Rheumatism. Jun. 2011; 63(6):1507-1516.

Vetrovsky, T. and Baldrian, P., The variability of the 16S rRNA gene in bacterial genomes and its consequences for bacterial community analyses. Plos One. Feb. 2013; 8(2): e57923.

Wang et al. 16S rRNA gene-based analysis of fecal microbiota from preterm infants with and without necrotizing enterocolitis. 2009. ISME J. 3(8): 944-954.

Workman et al. Guidelines for the welfare and use of animals in cancer research (2010) Br. J. Cancer. 102:1555-77.

Wunderlich, P.F. et al., Double-blind report on the efficacy of lactic acid-producing *Enterococcus* SF68 in the prevention of antibiotic-associated diarrhoea and in the treatment of acute diarrhoea. The journal of international medical research. 1989; 17: 333-338.

Xie et al. Short communication: Modulation of the small intestinal microbial community composition over short-term or long-term administration with Lactobacillus plantarum ZDY2013. 2016. Journal Dairy Sci. 99:6913-6921.

Xu, et al., The endogenous hydrogen sulfide producing enzyme cystathionine-i synthase contributes to visceral hypersensitivity in a rat model of irritable bowel syndrome. Molecular Pain, Biomed central, London, GB. Aug. 6, 2009; 5(1):p. 44.

Yang, J. et al., Targeting Th17 cells in autoimmune diseases. Trends Pharmacol Sci. Oct. 2014;35(10):493-500. doi: 10.1016/j.tips.2014.07.006. Epub Aug. 14, 2014.

Ye, X. et al., The Role of IL-23/Th17 Pathway in Patients with Primary Immune Thrombocytopenia. (2015) PLoS One. 10(1):e0117704.

Yin, X. et al., Combined effect of five single nucleotide polymorphisms related to IL23/Th17 pathway in the risk of psoriasis. Immunogenetics. Mar. 2014;66(3):215-8. doi: 10.1007/s00251-013-0756-z. Epub Jan. 14, 2014.

Yq et al. Therapeutic Modulation of the Gut Microbiota in IBD—More Questions to Be Answered. (2016). J. Dig. Dis., Oct. 15, 1751-2980, 12422, Epub ahead of print.

Yutin, N. and Galperin, M.Y., A genomic update on clostridial phylogeny:Gram-negative spore formers and other misplaced clostridia. Environmental microbiology. 20136; 15(10): 2631-2641.

Zhang, B. et al., Oral administration of *enterococcus faecalis* FK-23 suppresses Th17 cell development and attenuates allergic airway responses in mice. International journal of molecular medicine. 2012; 30:248-254.

Zhang, B. et al., The Prevalence of Th17 Cells in Patients With Gastric Cancer. 2008. Biochem Biophys Res Commun 374 (3), 533-537.

Zhang, et al., The Activation of NF-κB in Infiltrated Mononuclear Cells Negatively Correlates with Treg Cell Frequency in Oral Lichen Planus. Inflammation. Aug. 2015;38(4):1683-9. doi: 10.1007/s10753-015-0145-x.

(56) References Cited

OTHER PUBLICATIONS

Zheng, B. et al., Bifidobacteriu breve attenuates murine dextran sodium sulfate-induced colitis and increases regulatory T cell responses. PLOS one. May 2014; 9(5).

Zhongyuan, T. et al., The inflammation regulation effects of *enterococcus faecium* HDRsEf1 on human enterocyte-like HT-29 cells. Animal cells and systems. Mar. 2016;20(2):70-76.

Zhou et al. Central and peripherial hypersensitivity in the irritable bowel syndrome. 2010. Pain. 148(3): 454-461.

Zhu, S. and Qian, Y., IL-17/IL-17 receptor system in autoimmune disease: mechanisms and therapeutic potential. Clinical Science (2012) 122, 487-511.

Zitomersky, N. et al., Characterization of Adherent Bacteroidales from Intestinal Biopsies of Children and Young Adults with Inflammatory Bowel Disease. PLOS one. 2013; 8(6).

Zitvogel, et al., Type I interferons in anticancer immunity. Nature Reviews. Jul. 2015:405-414.

4d Pharma PLC: "Clinical Update—RNS—London Stock Exchange", Jul. 19, 2016.

Anonymous: "4D pharma's Blautix for Irritable Bowel Syndrome shows positive impact—pharmaceutical daily news", Dec. 13, 2016.

Bernalier, A., et al., "Diversity of H2/C02-utilizing acetogenic Bacteria from Feces of Non-Methane-Producing Humans", Current Microbiology vol. 33 (Aug. 1996) pp. 94-99, Springer-Vertag New York Inc., USA.

Bernalier et al., "Acetogenesis from H02 and C0-2 By Methane and Non-Methane-Producing Human Colonic Bacterial Communities" Fems Microbiology Ecology. vol. 19, No. 3. 1996. pp. 193-202. XP000979130.

Co-pending U.S. Appl. No. 15/906,988, filed Feb. 27, 2018.

DMSZ: Opening of Ampoules and Rehydration of Dried Cultures; (http://web.archive.org/web/20000 52411541 O/www.dsmz.de/open. htm); updated of website on Mar. 2000.

GB1612190.7 International Search Report dated Apr. 12, 2017.

O'Sullivan et al., "Bacterial Supplementation in the Irritable Bowel Syndrome. A Randomised Double-Blind Placebo-Controlled Crossover Study", Digest Liver Dis. 2000. pp. 294-301.

PCT/EP2017/025038 International Search Report and Written Report dated Jun. 12, 2017.

PCT/GB2017/052077 International Search Report dated Oct. 16, 2017.

PCT/GB2017/052077 Written Opinion dated Oct. 16, 2017.

U.S. Appl. No. 15/359,144 Office Action dated Apr. 10, 2018.

U.S. Appl. No. 15/359,972 Office Action dated Apr. 4, 2018.

U.S. Appl. No. 15/673,270 Office Action dated Apr. 10, 2018.

Van Nevel et al., "Conrol of Rumen Methanogenesis." Environmental Monitoring and Assessment. vol. 42, 1996, pp. 73097, XP000979267.

Distrutti, et al., Hydrogen sulphide induces u opioid receptor-dependent analgesia in a rodent model of visceral pain. Molecular Pain, 2010; 6(36):1-16.

PCT/EP2017/025038 Written Opinion of the International Preliminary Examining Authority dated Jan. 25, 2018.

PCT/EP2017/025038 International Preliminary Report on Patentability dated Jun. 6, 2018, 8 Pages.

PCT/GB2017/052076 Written Opinion of the International Preliminary Examining Authority dated Jun. 21, 2018, 11 Pages.

PCT/GB2017/052077 Written Opinion of the International Preliminary Examining Authority dated Jun. 21, 2018, 10 Pages.

* cited by examiner

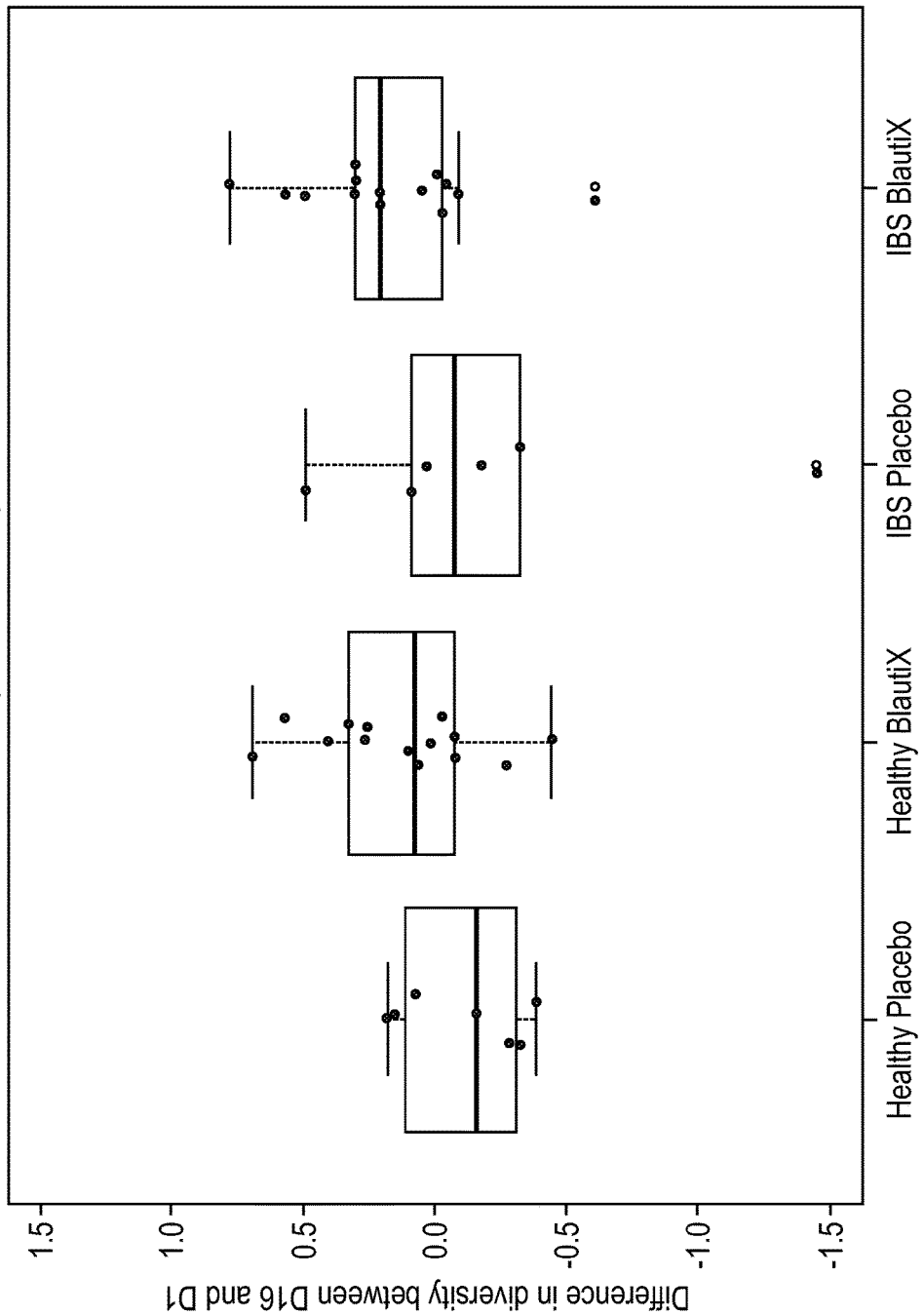

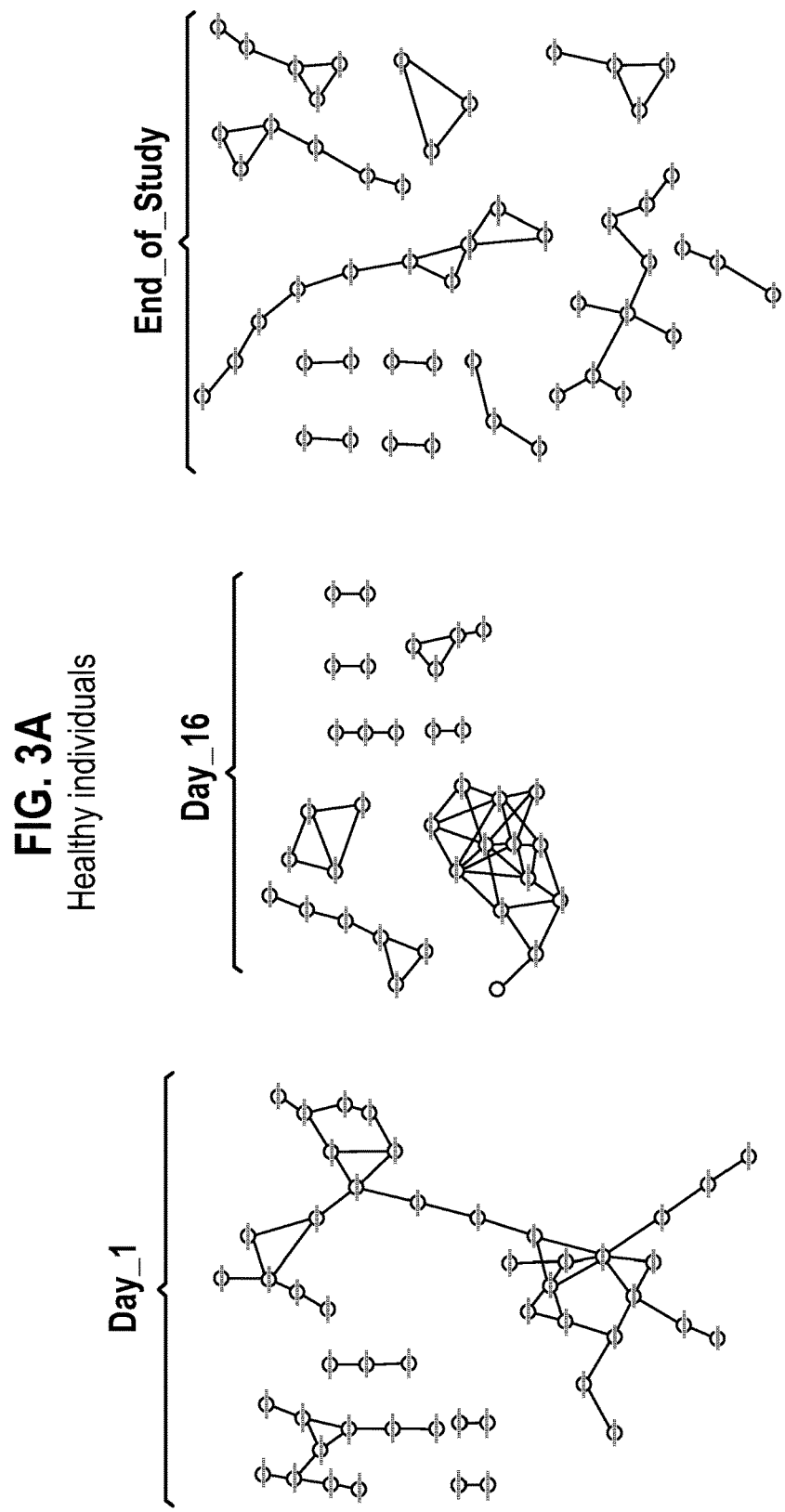

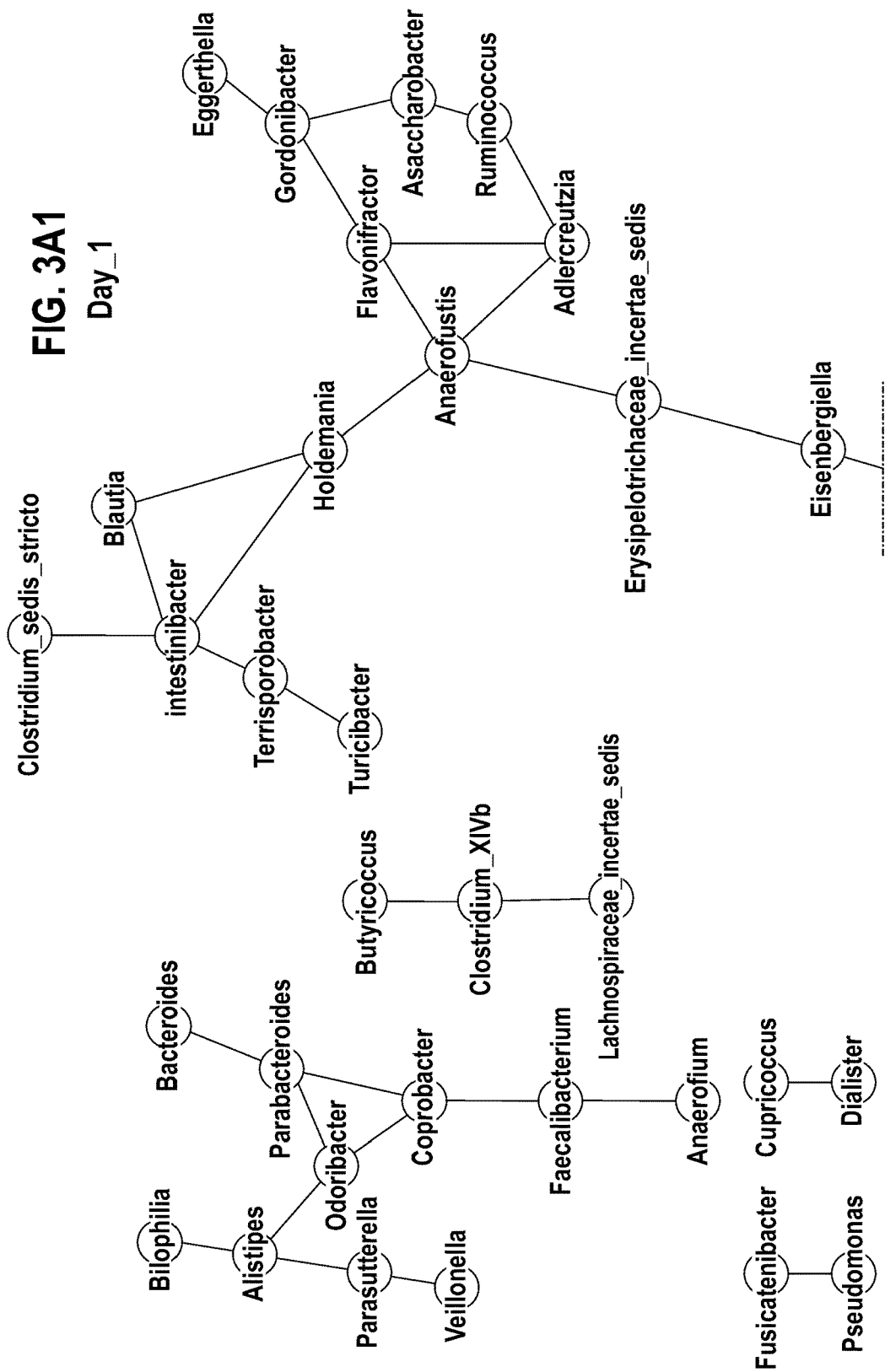
FIG. 3A1
Day_1

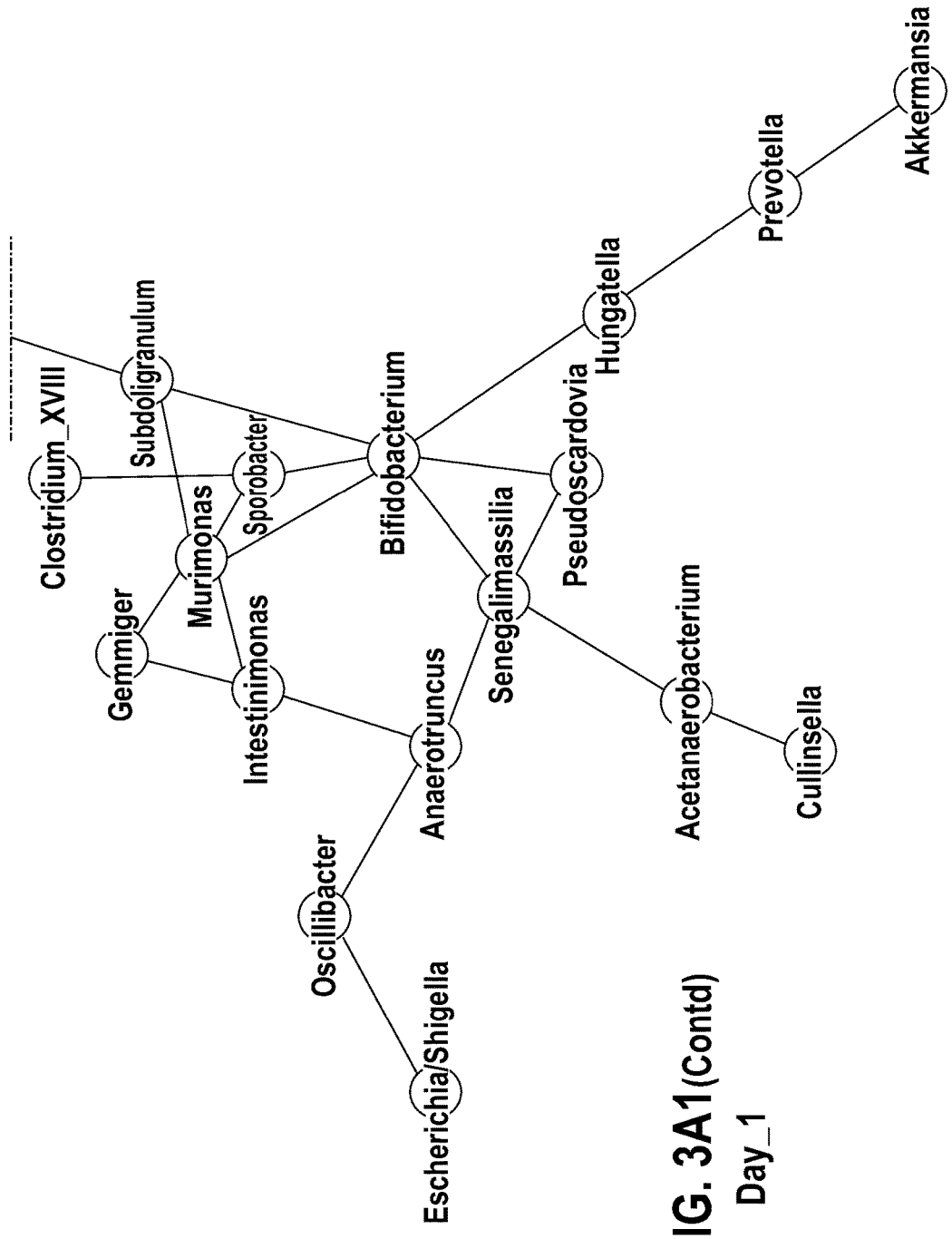
FIG. 3A1(Contd)
Day_1

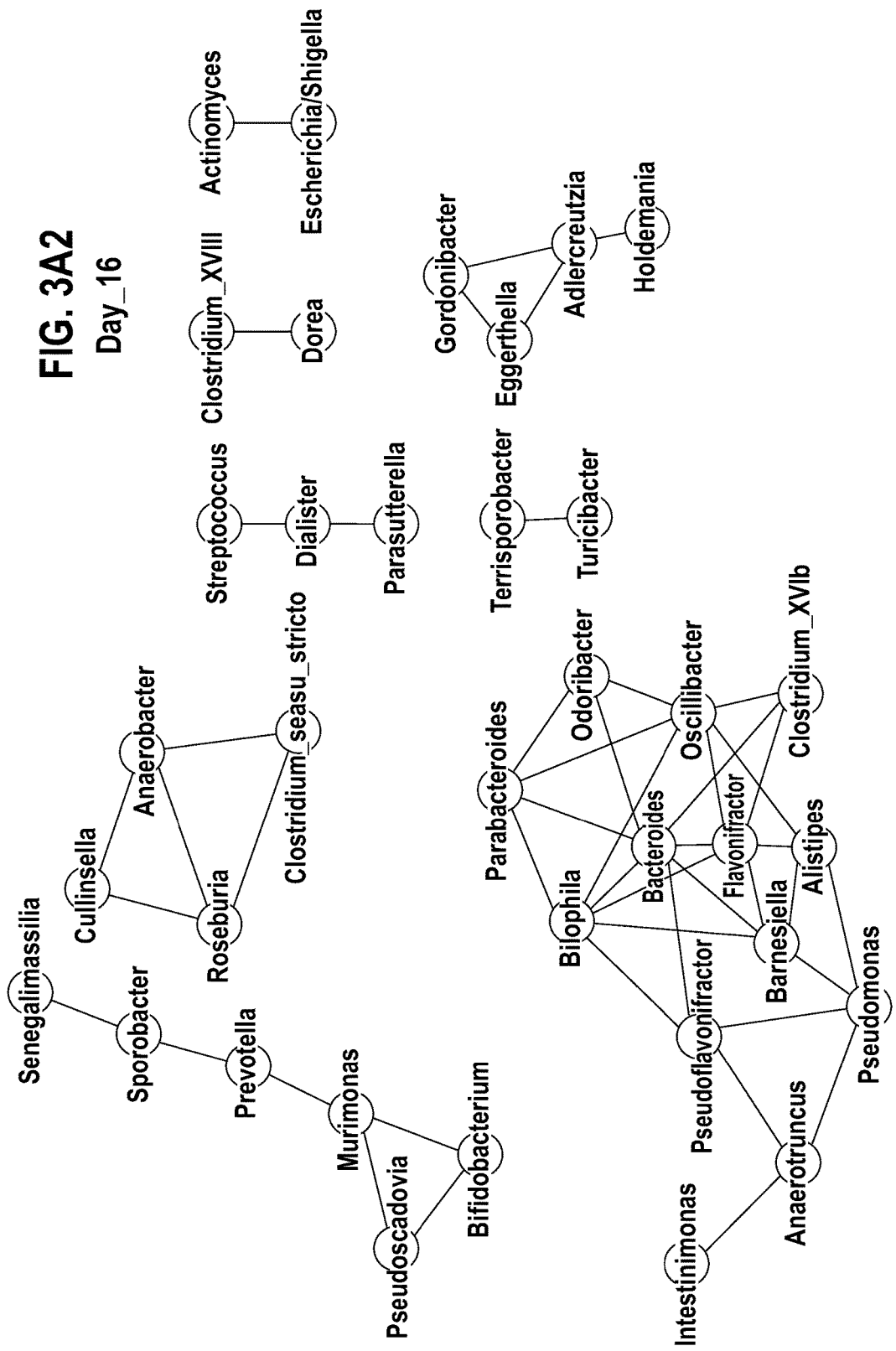
FIG. 3A2
Day_16

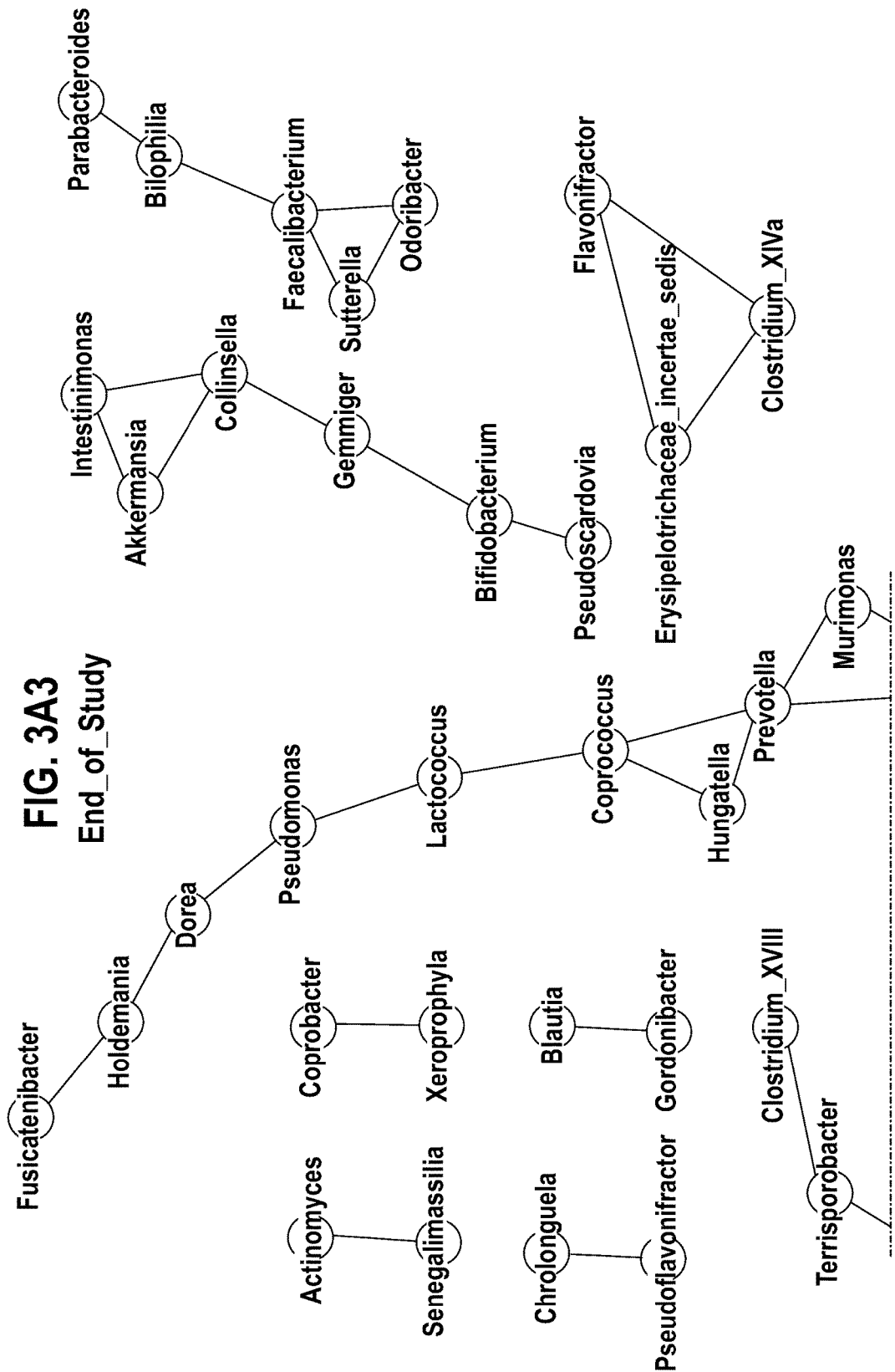
FIG. 3A3 End_of_Study

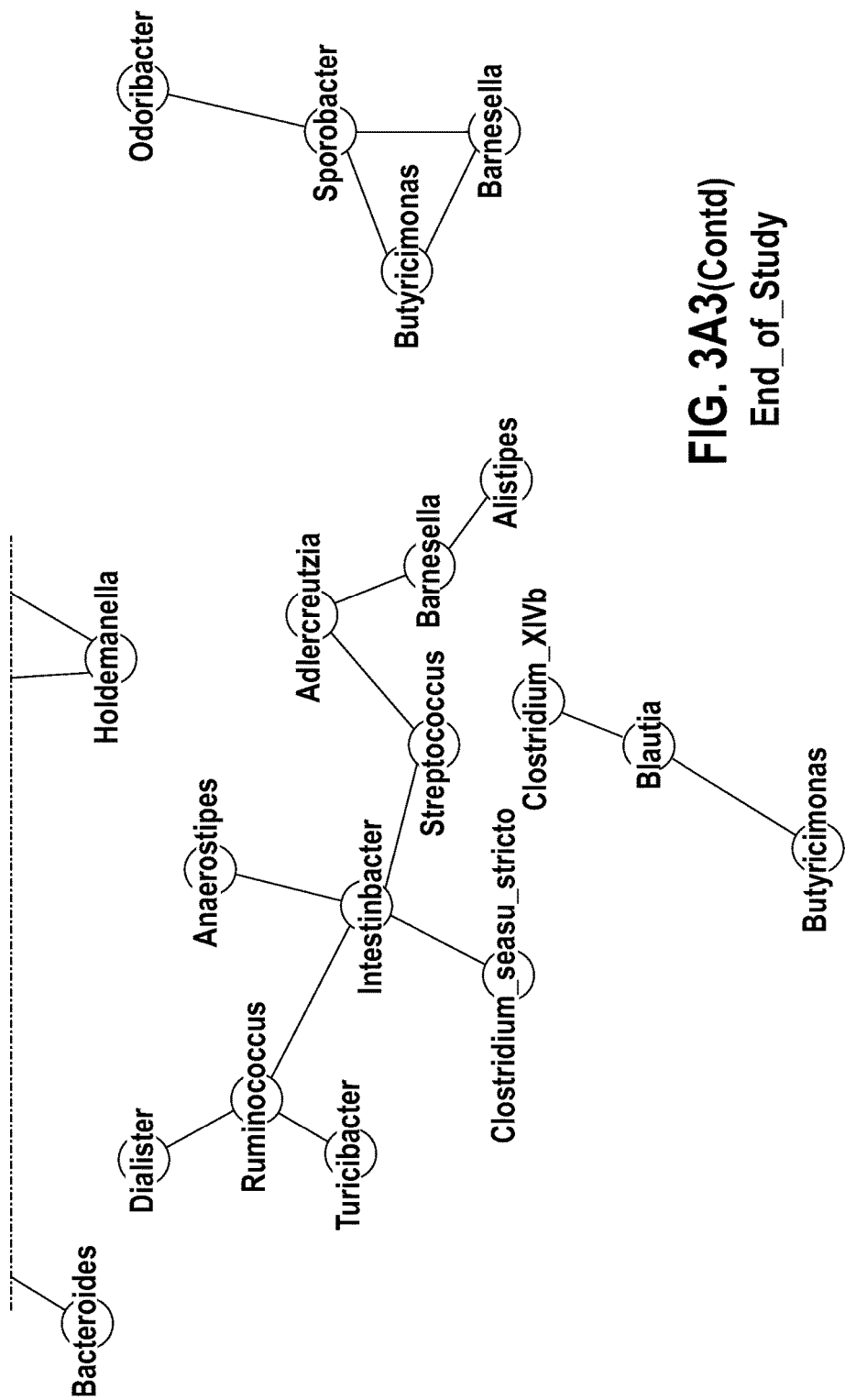
FIG. 3A3(Contd)
End_of_Study

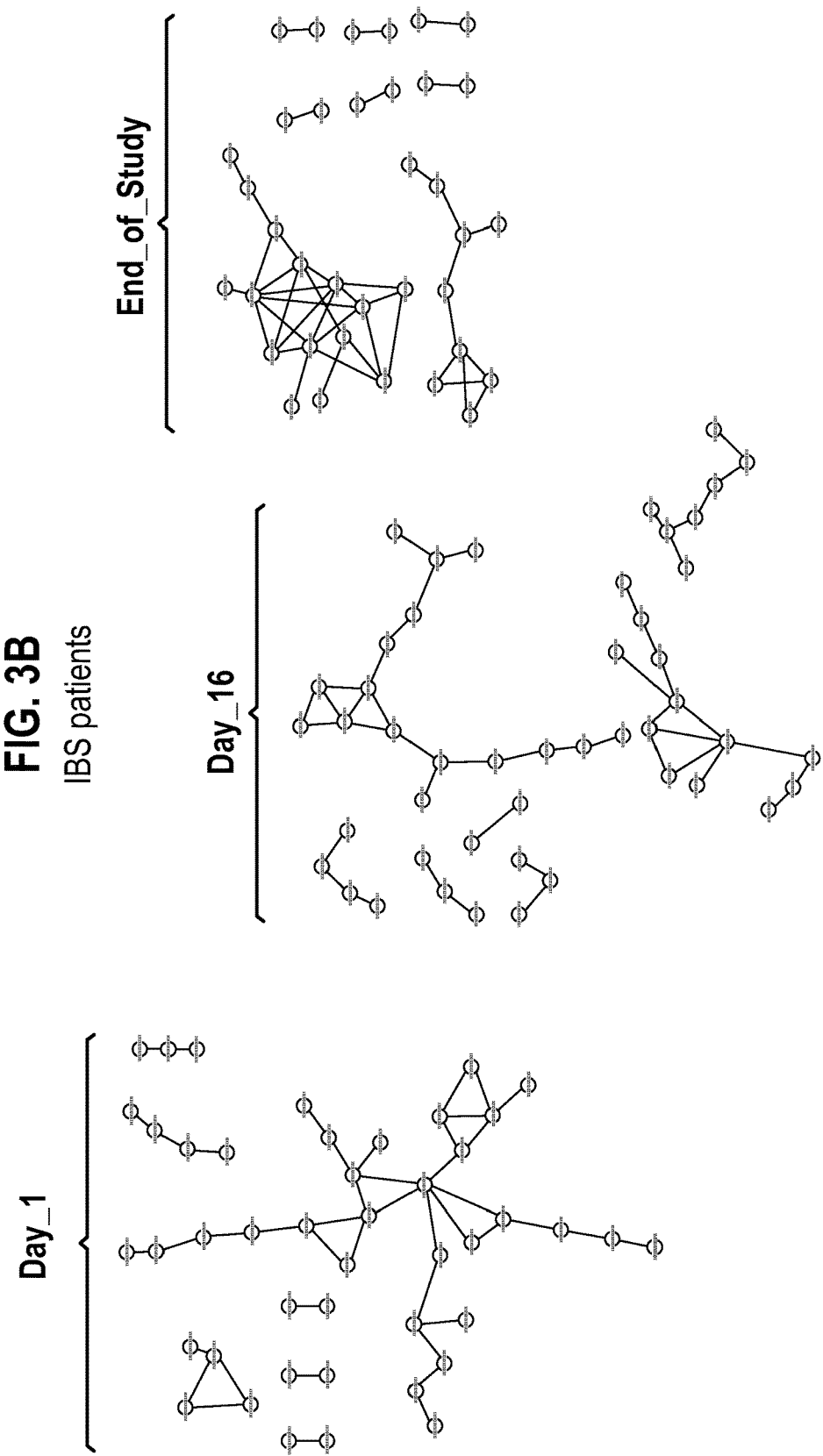

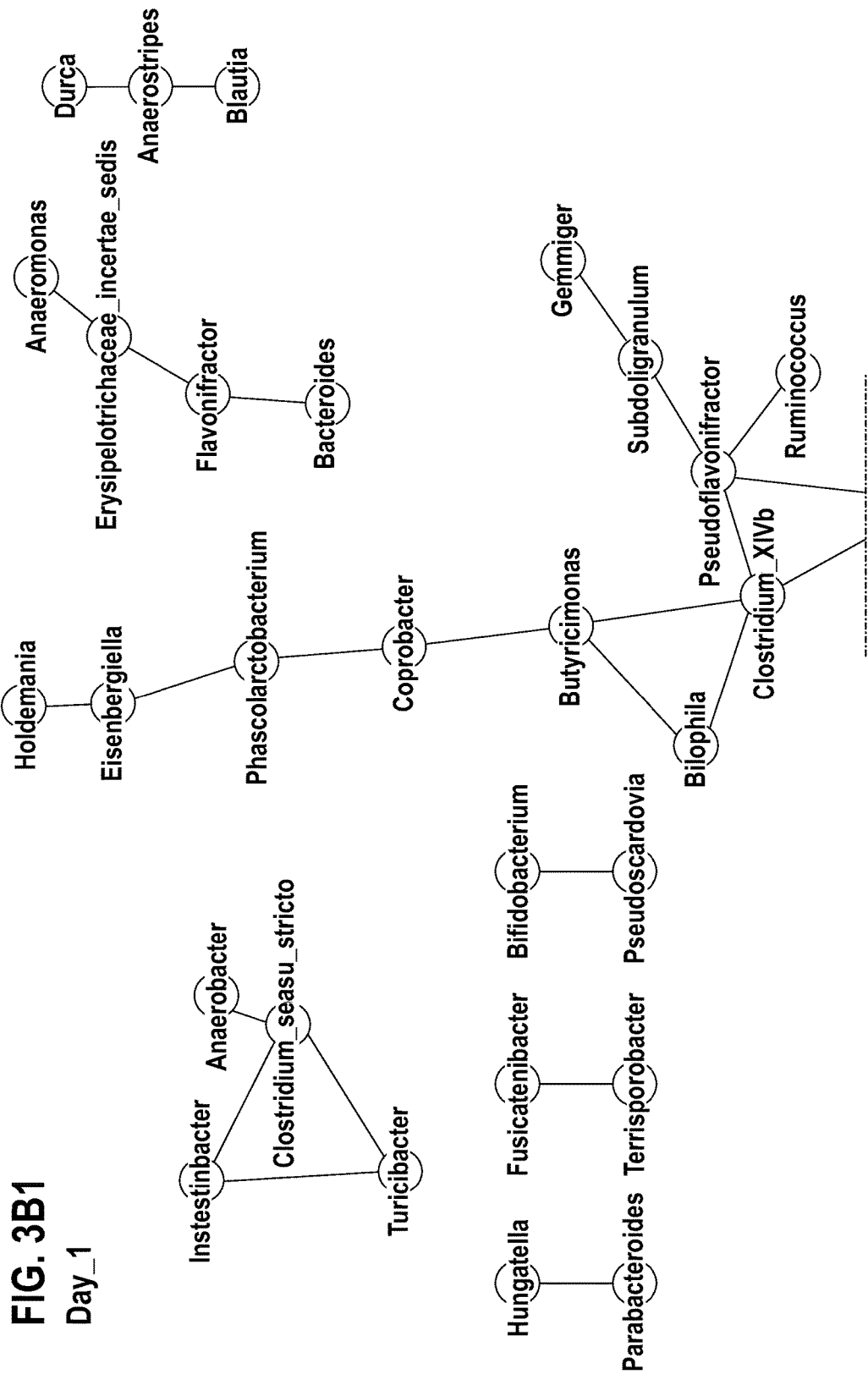
FIG. 3B1
Day_1

FIG. 3B1(Contd)
Day_1

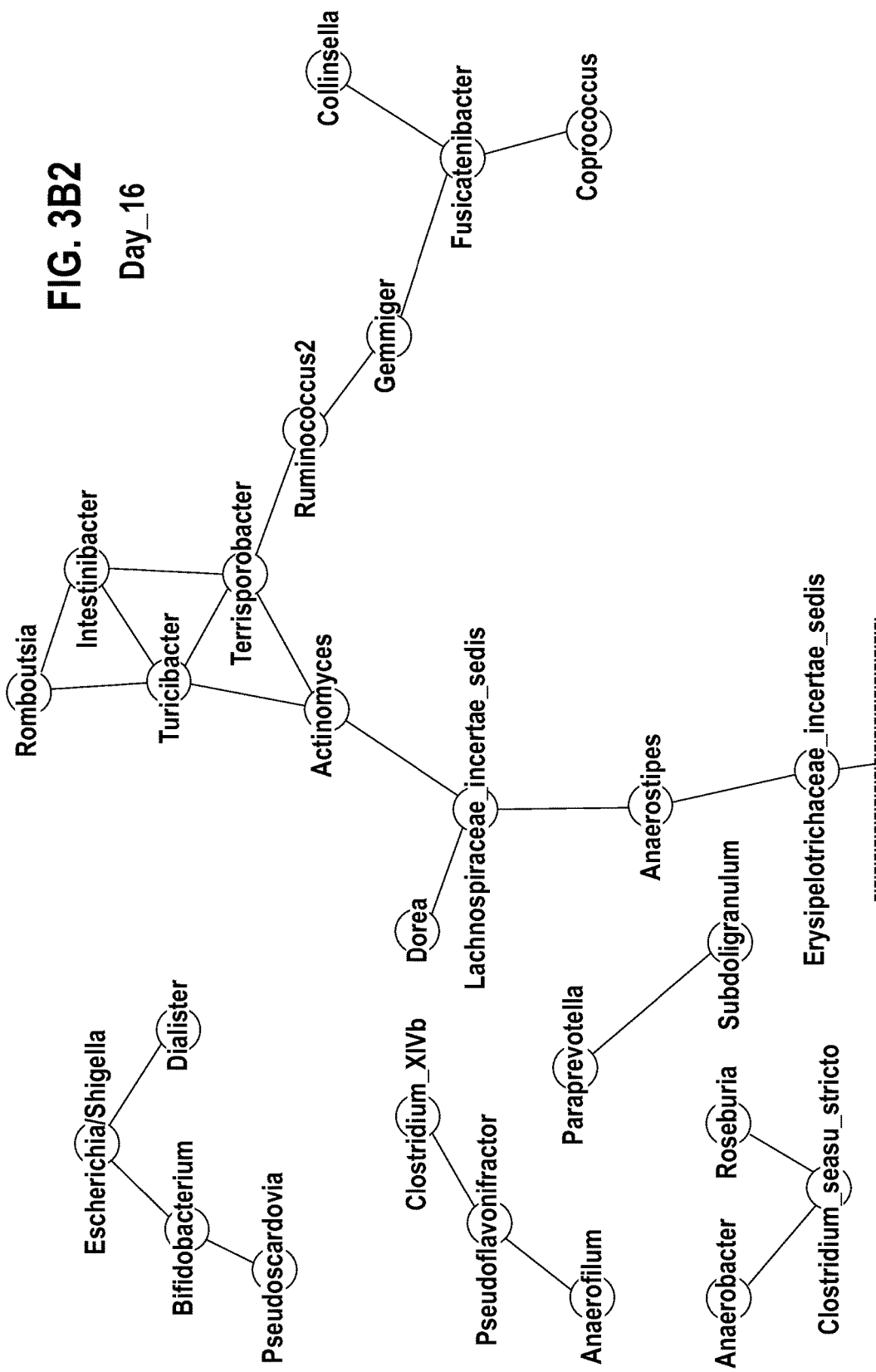
FIG. 3B2 Day_16

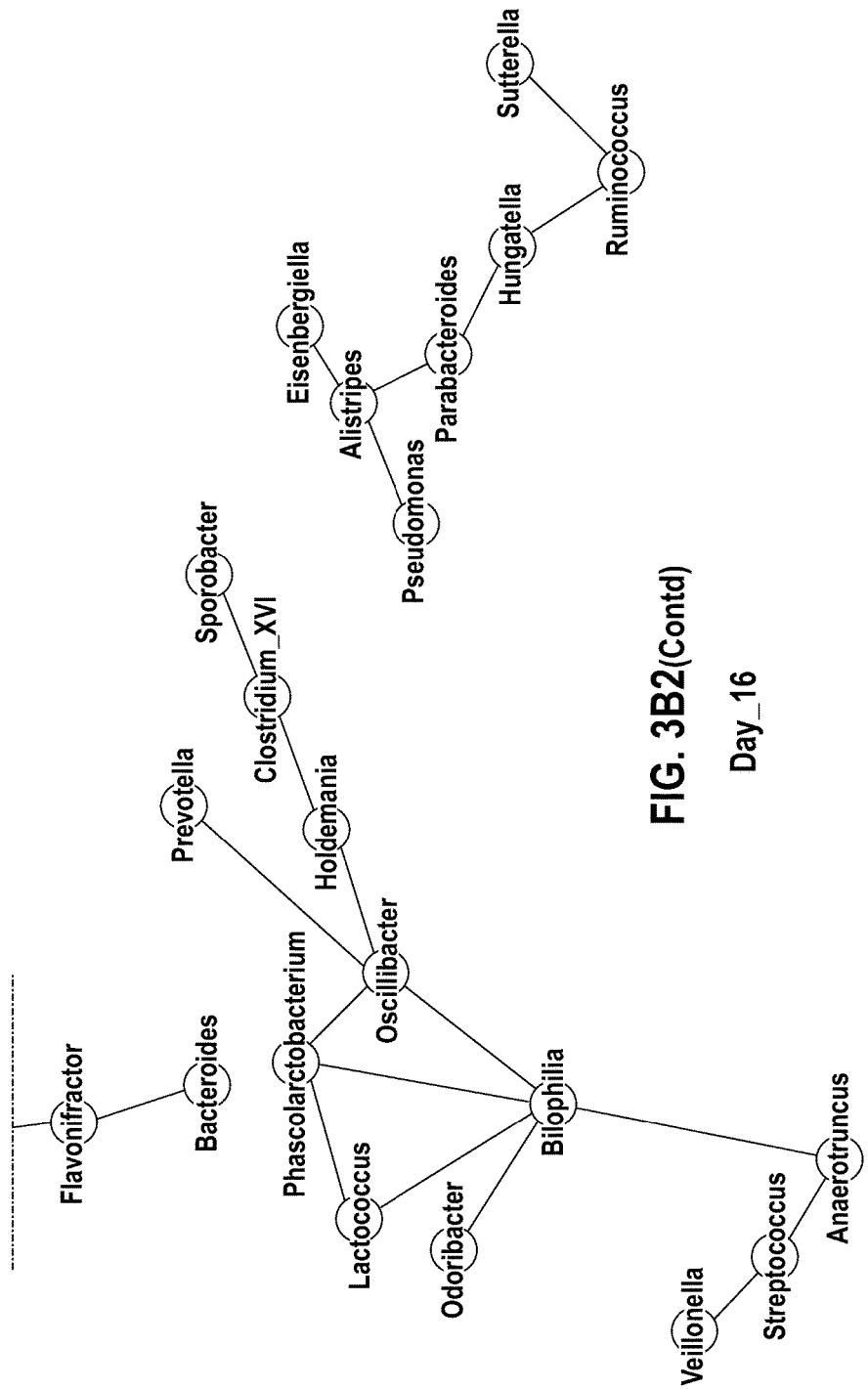
FIG. 3B2(Contd)
Day_16

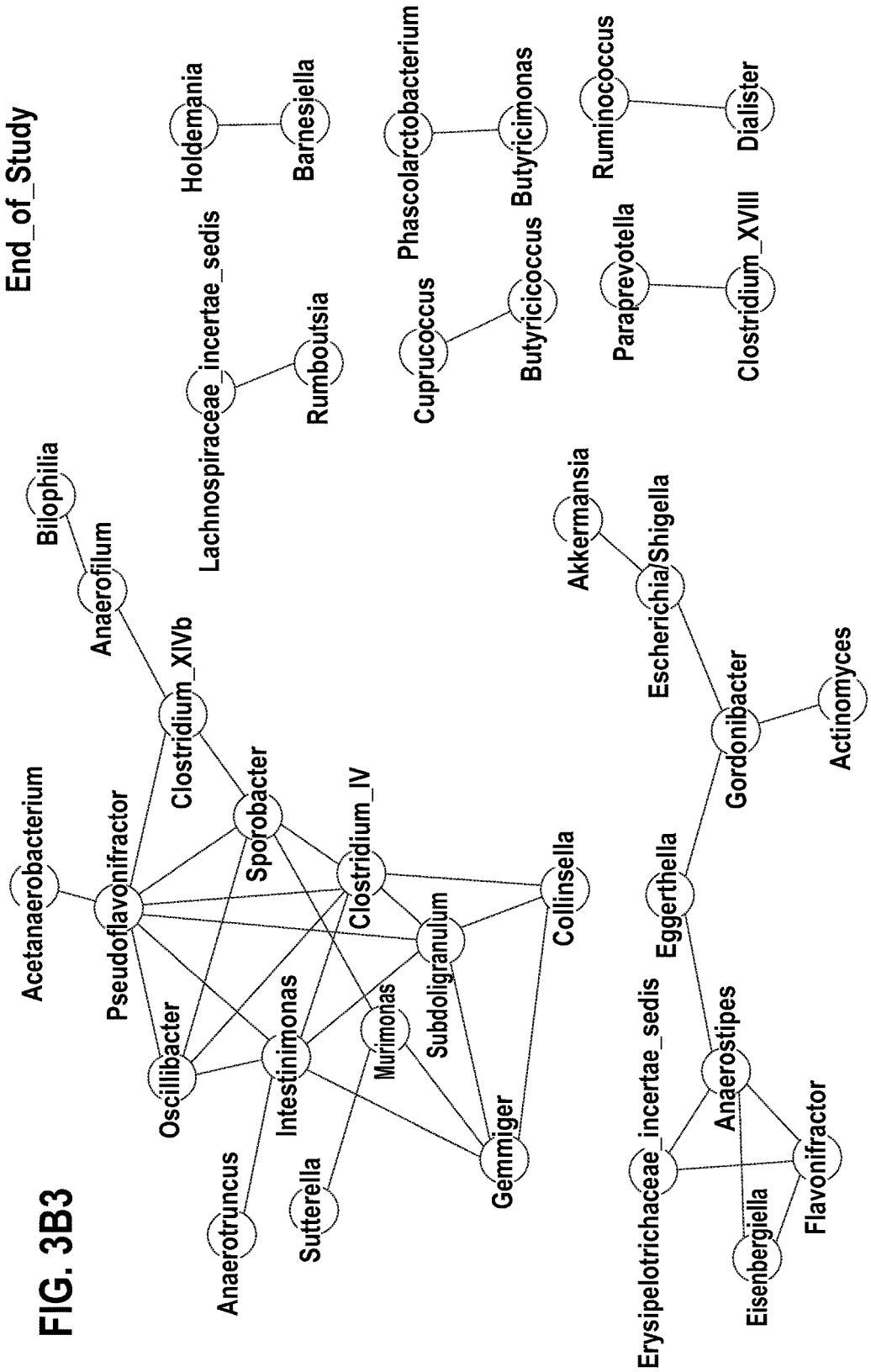
FIG. 3B3

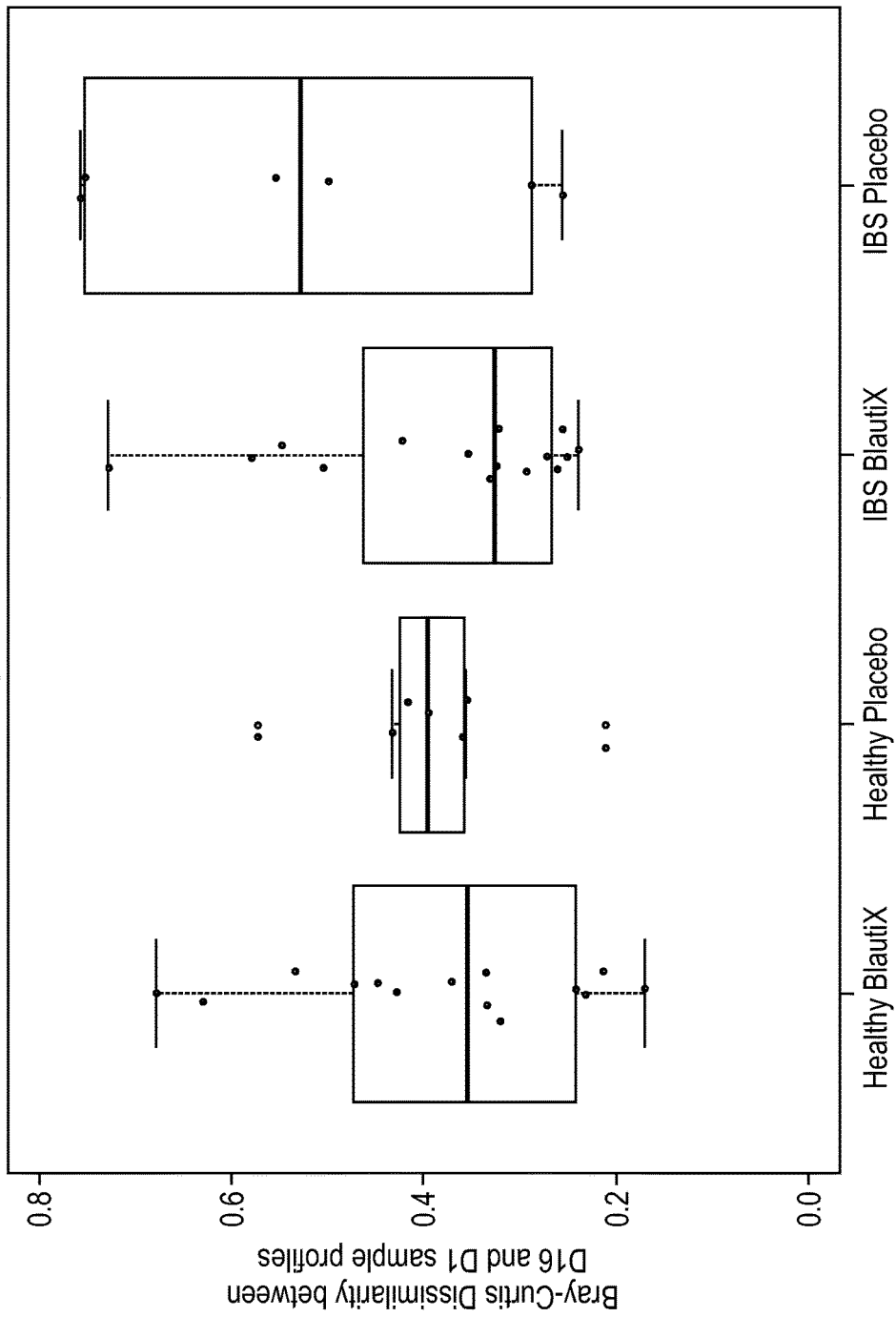

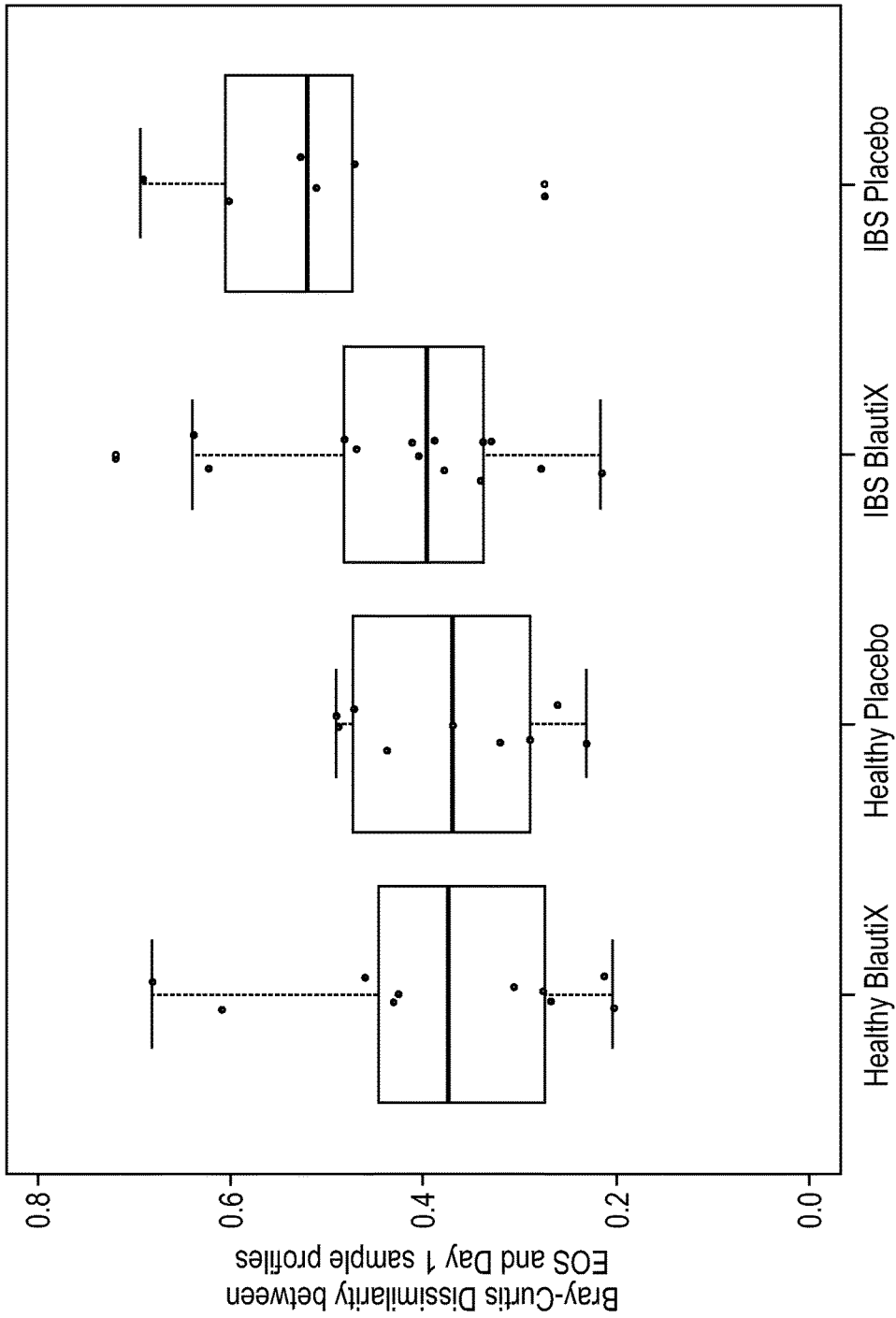

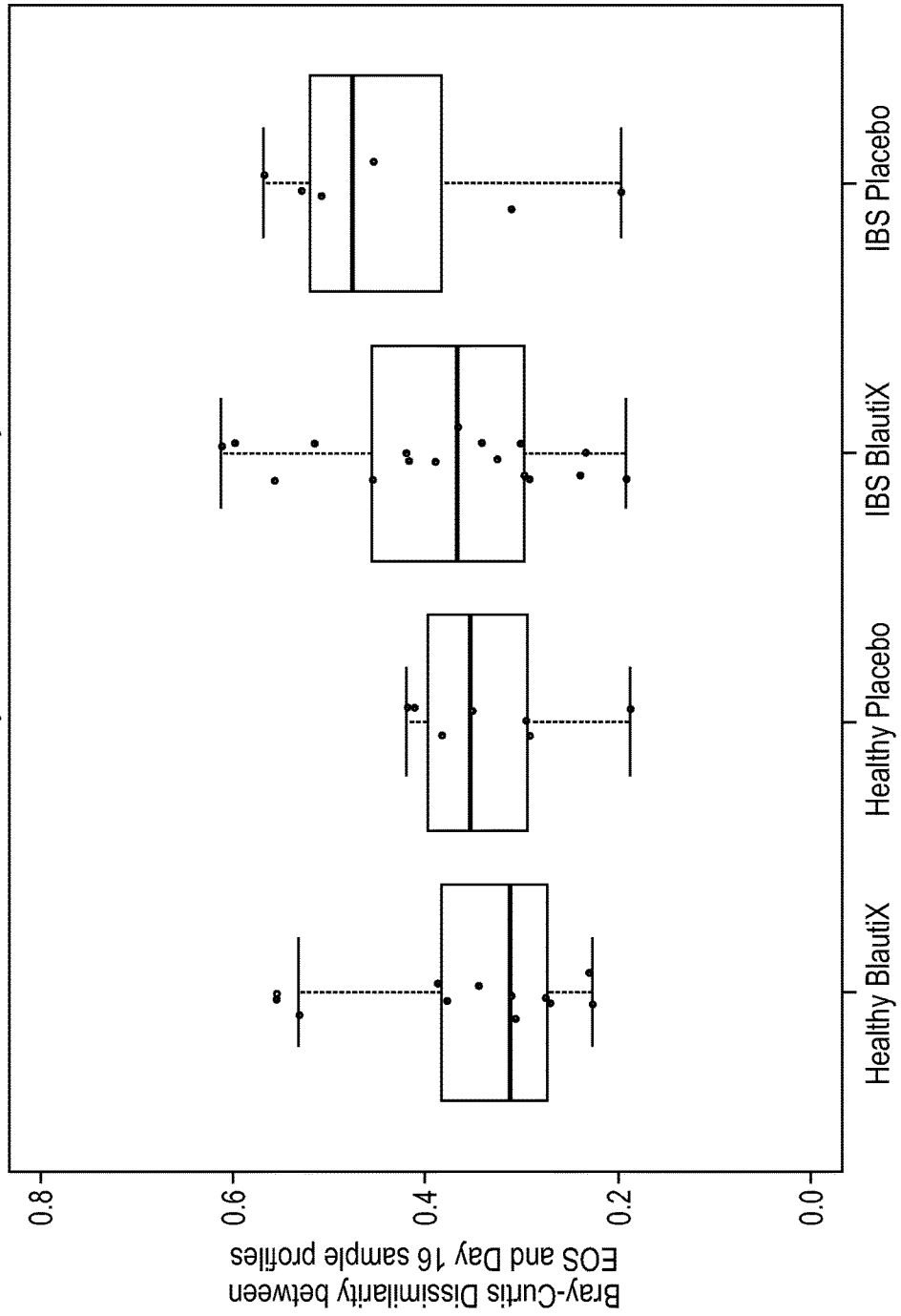

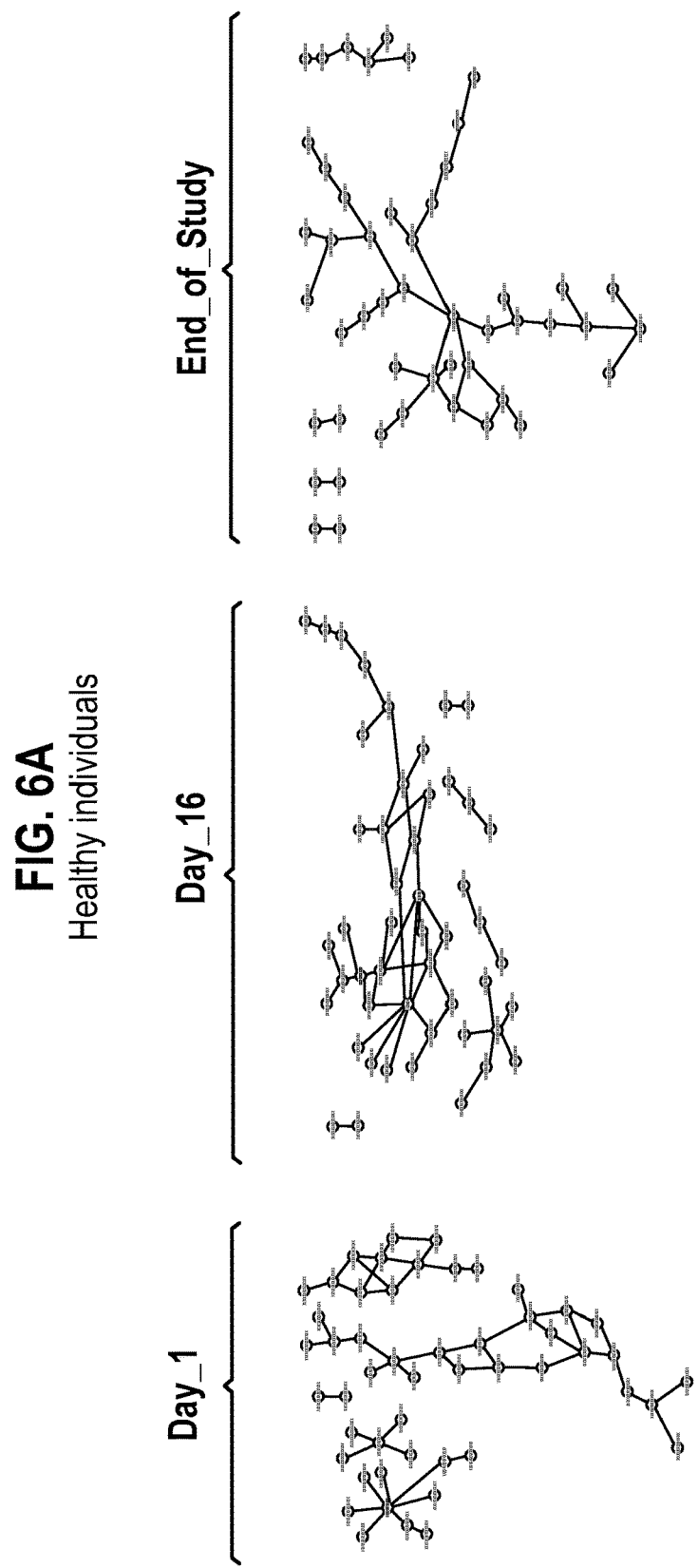

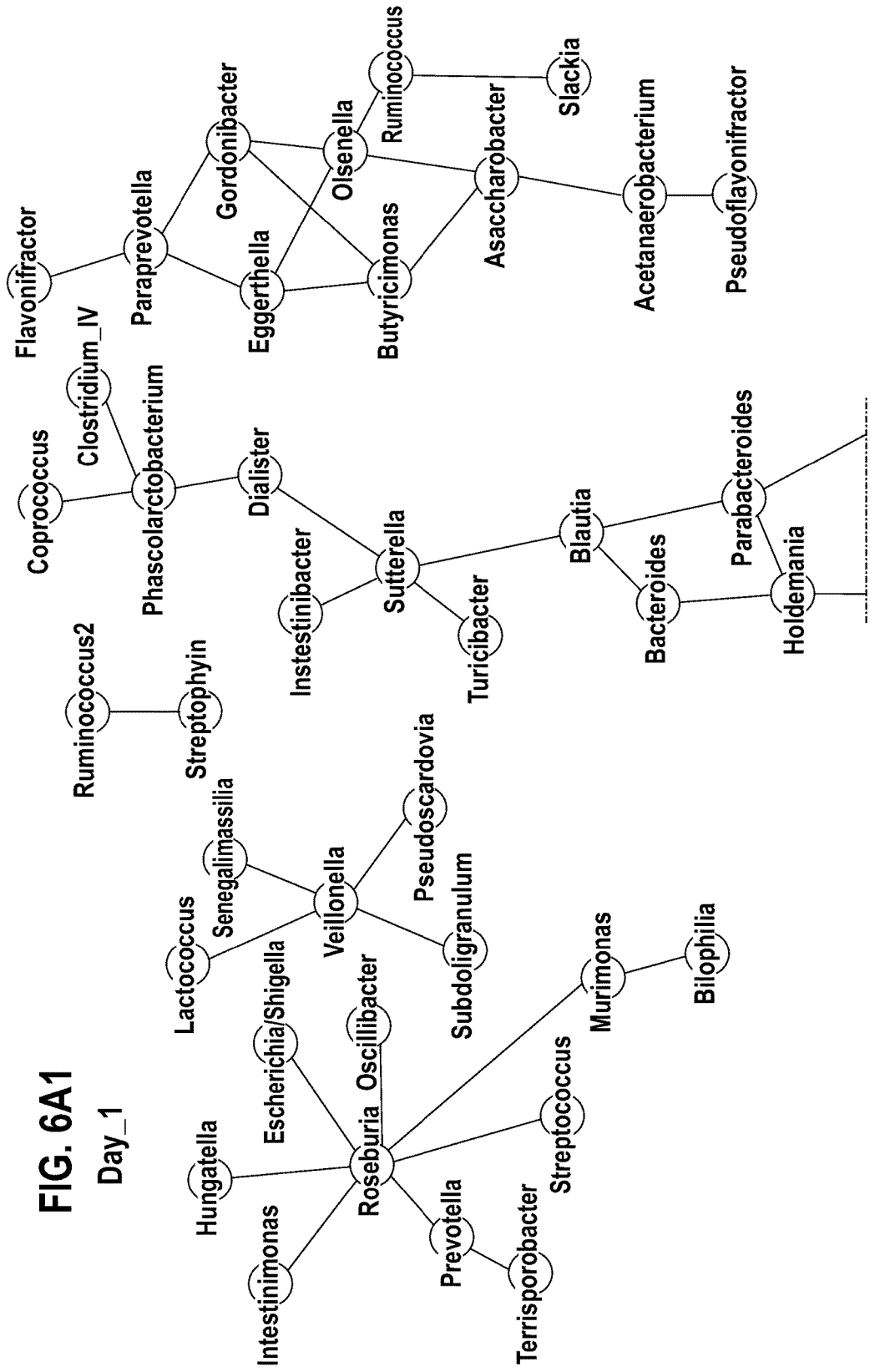
FIG. 6A1 Day_1

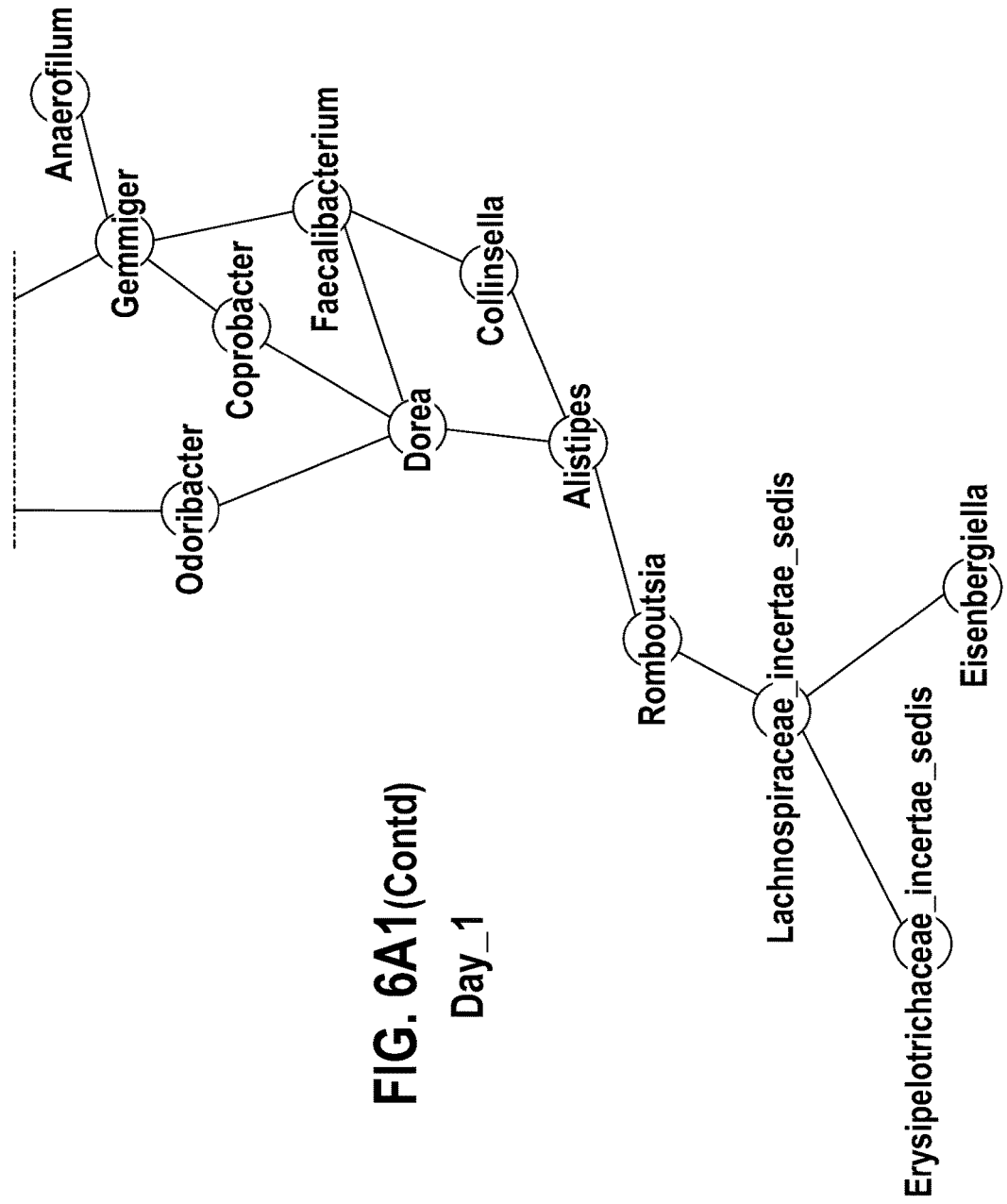
FIG. 6A1(Contd)
Day_1

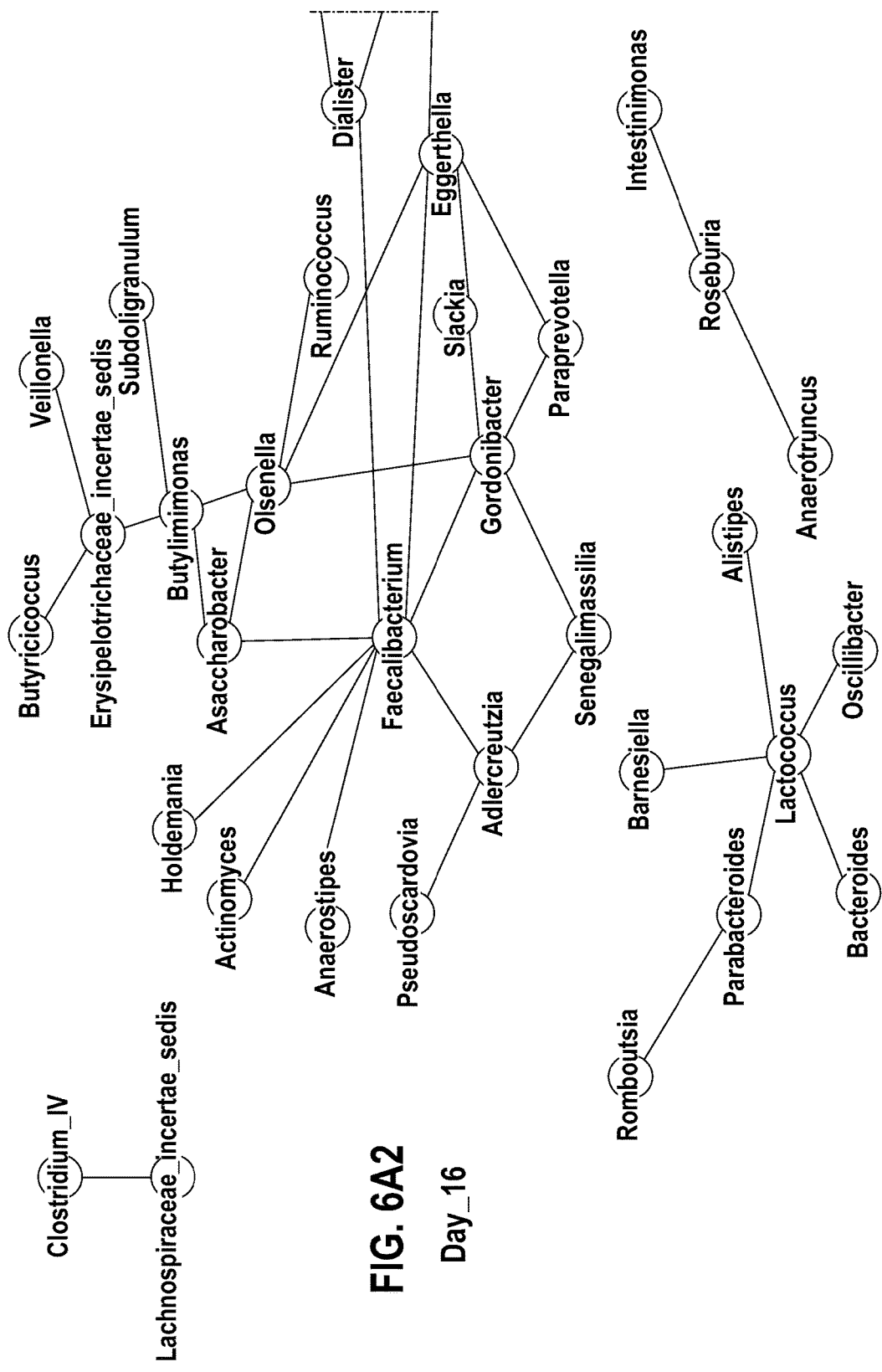
FIG. 6A2
Day_16

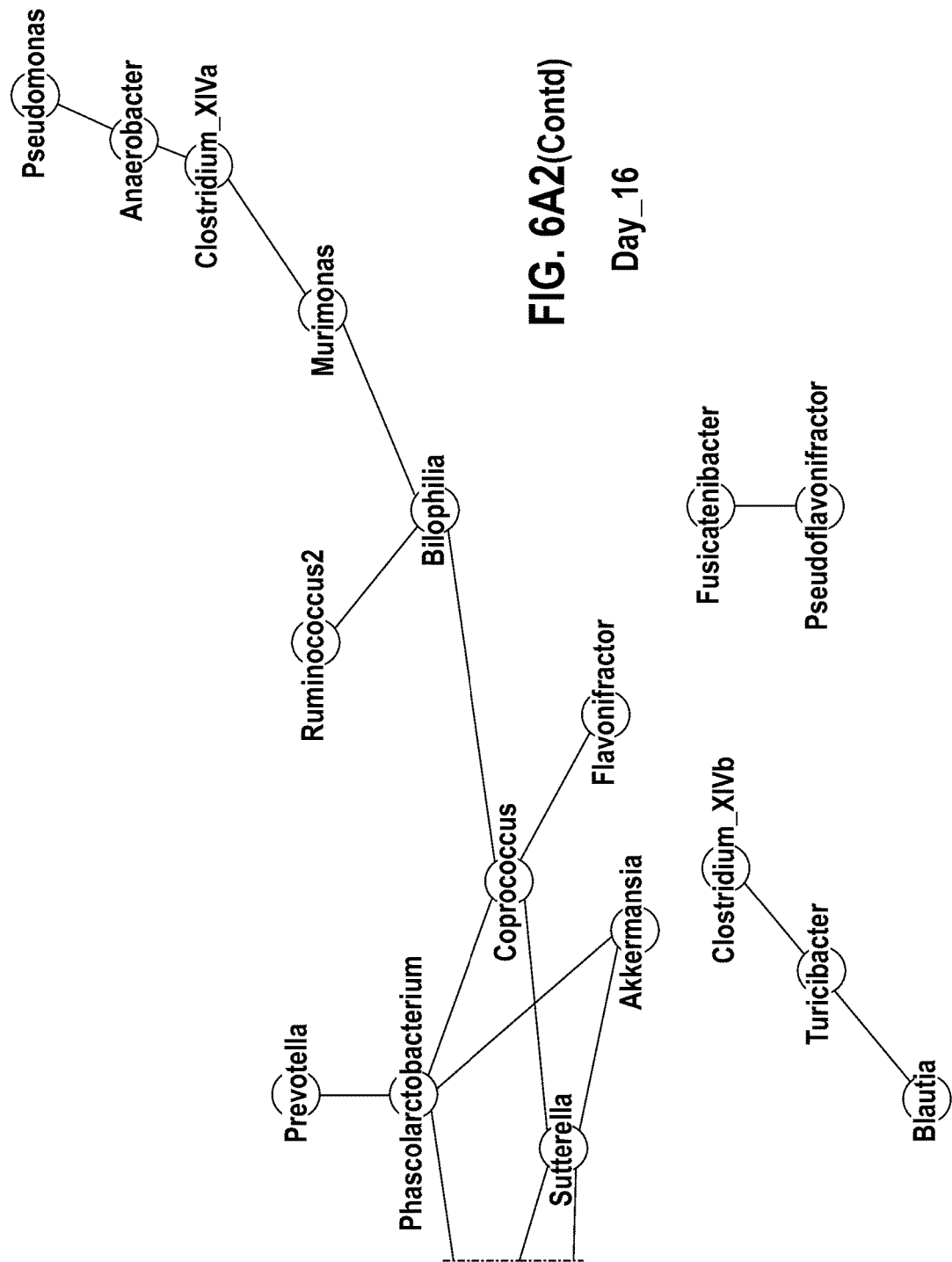
FIG. 6A2(Contd)
Day_16

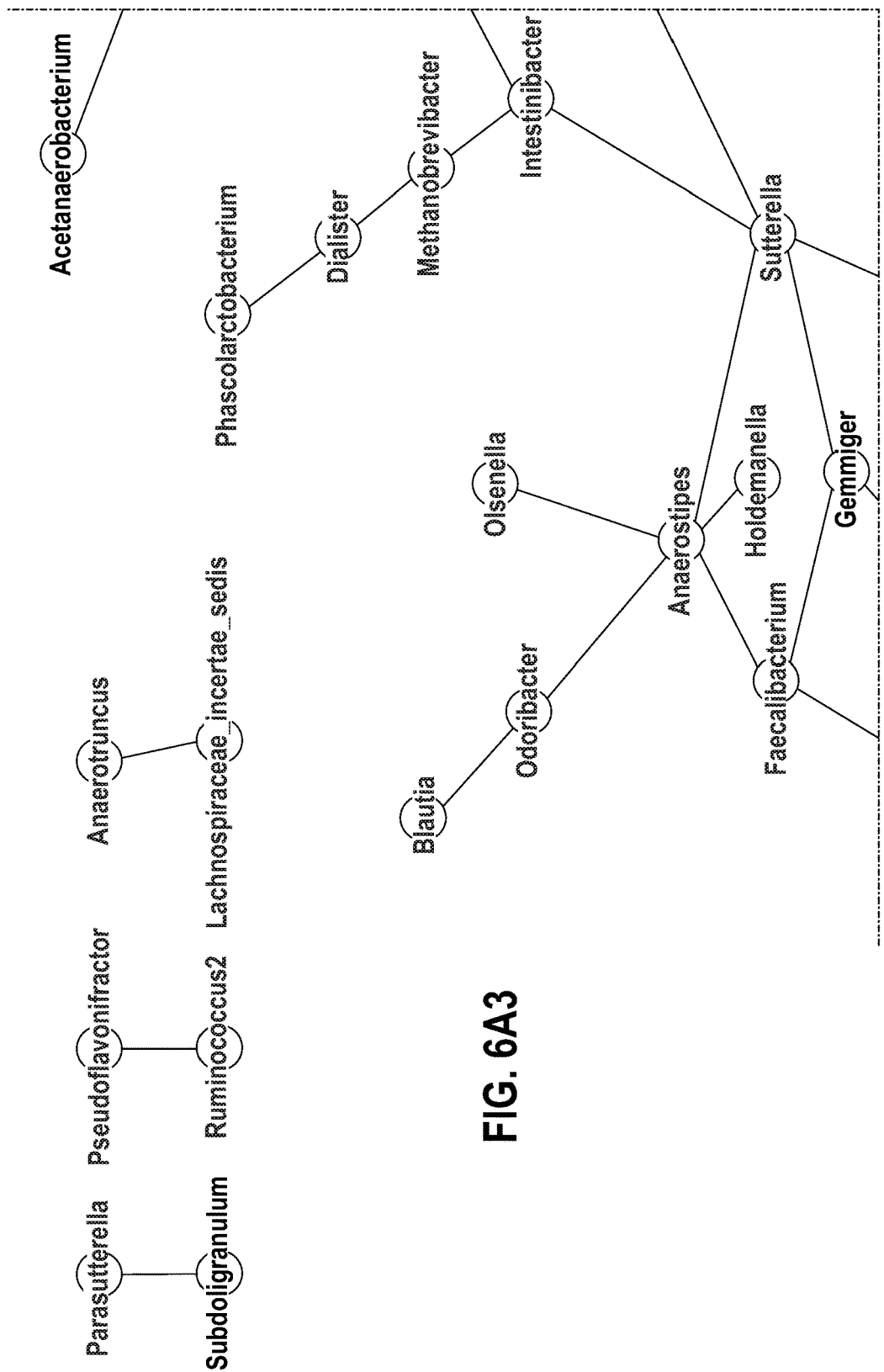
FIG. 6A3

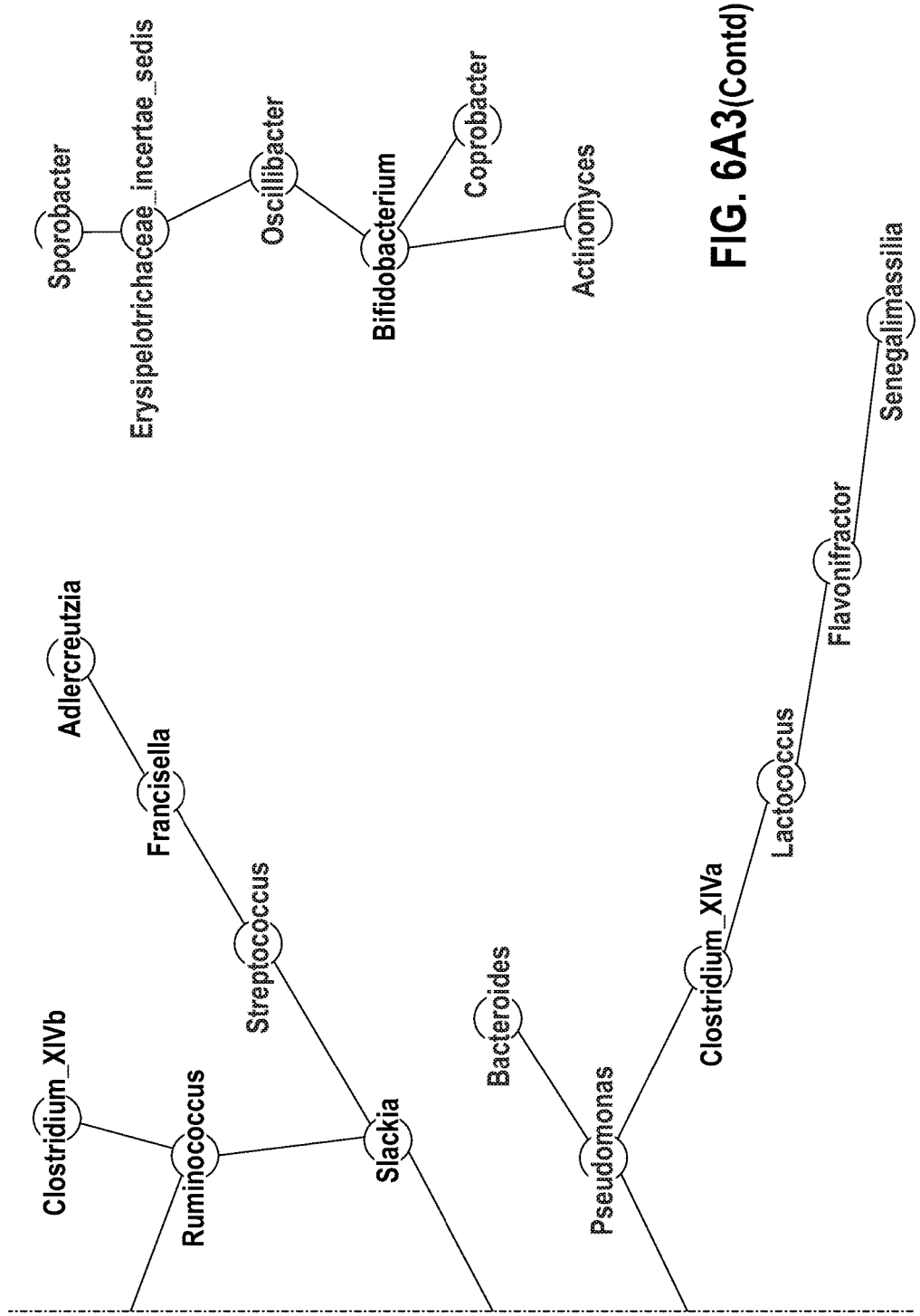
FIG. 6A3(Contd)

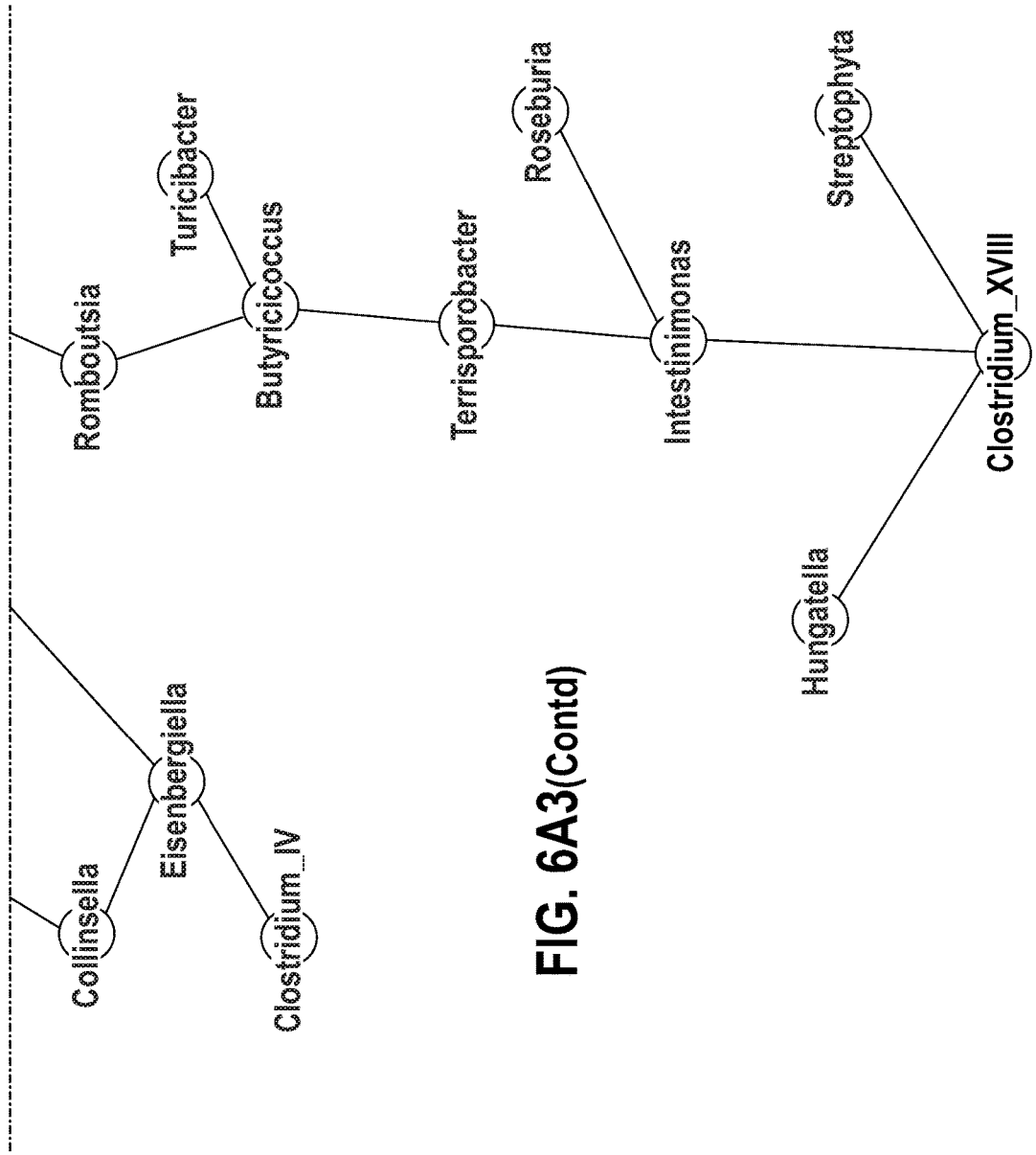
FIG. 6A3(Contd)

IBS individuals

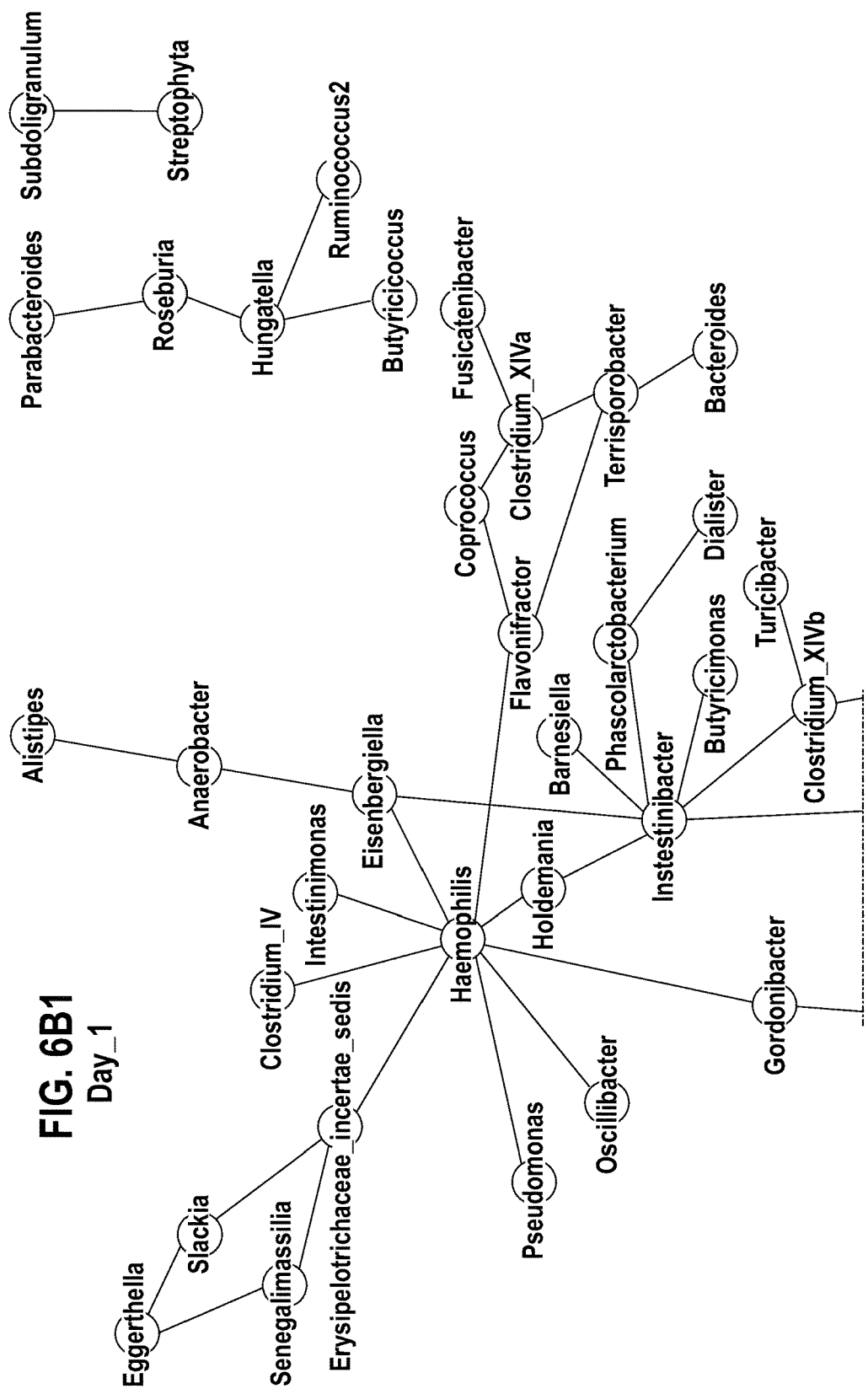
FIG. 6B1
Day_1

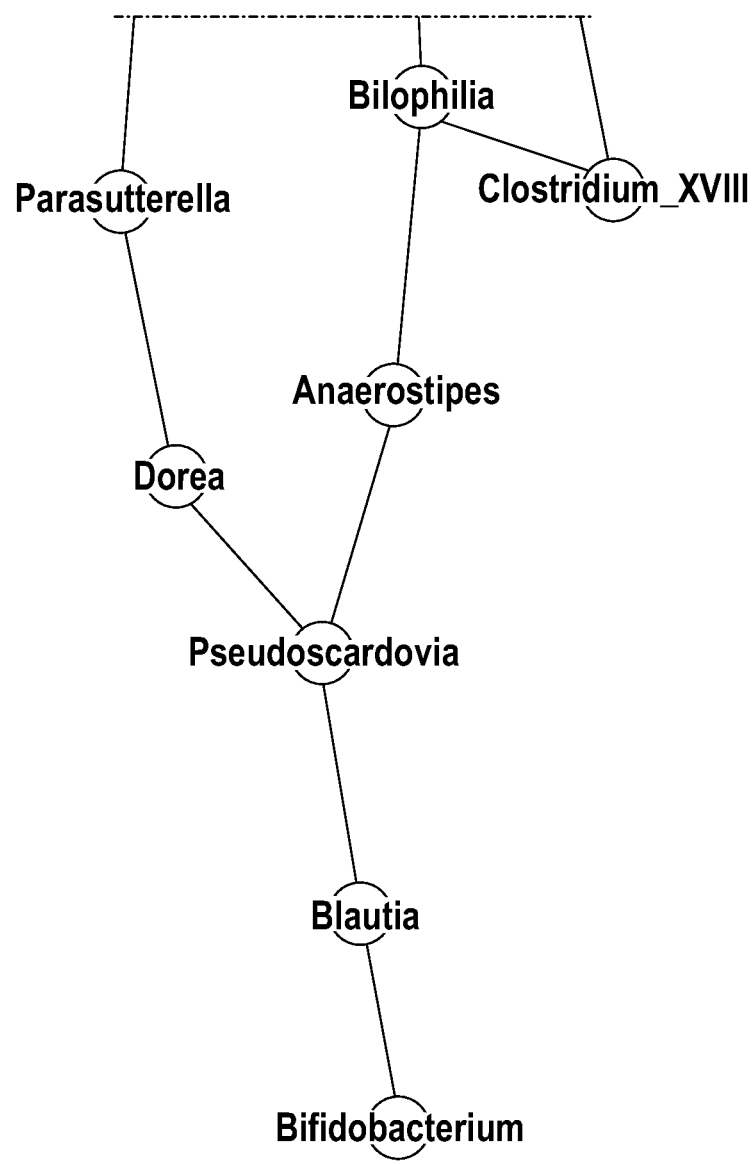
Day_1
FIG. 6B1(Contd)

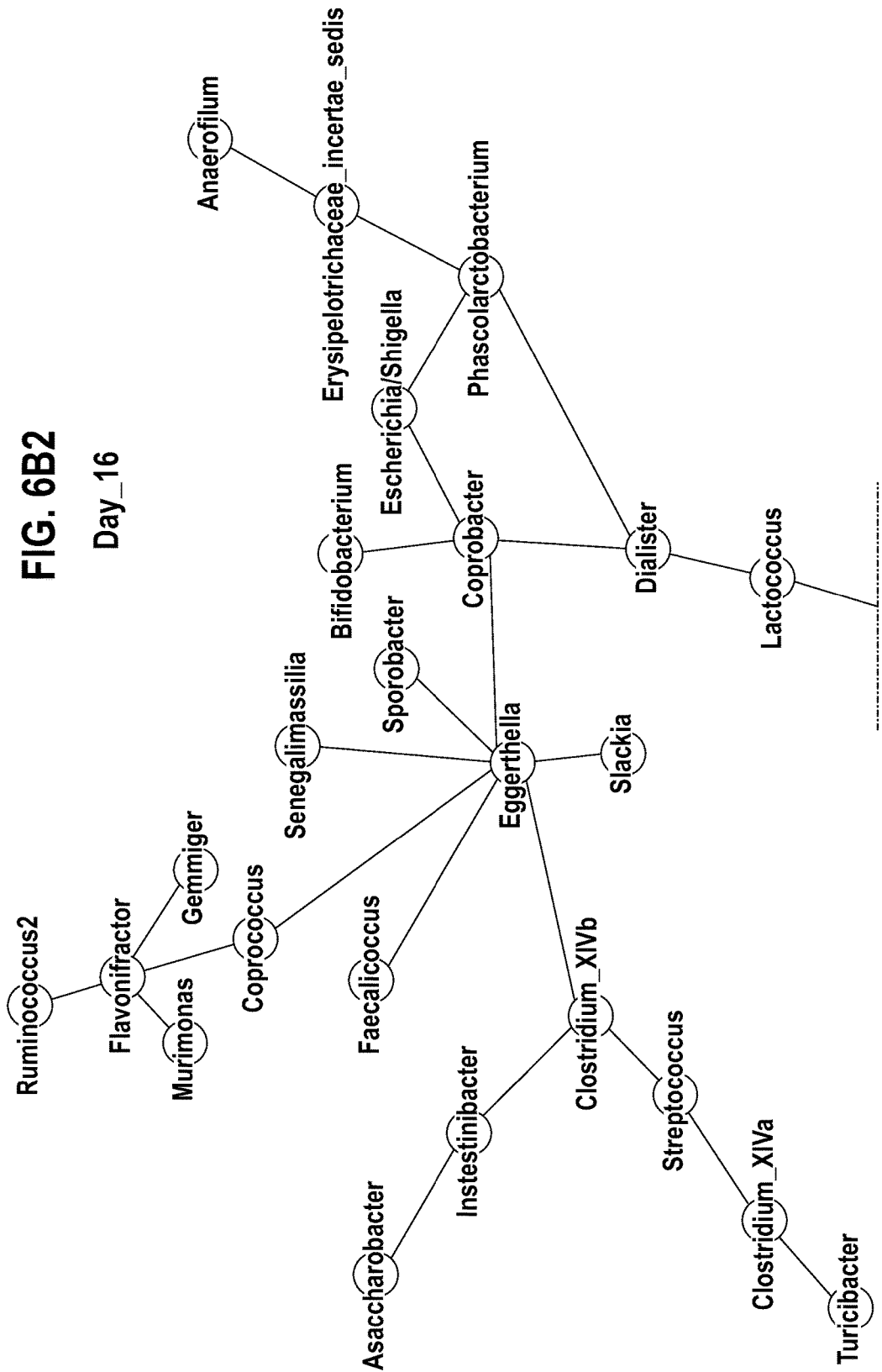
FIG. 6B2
Day_16

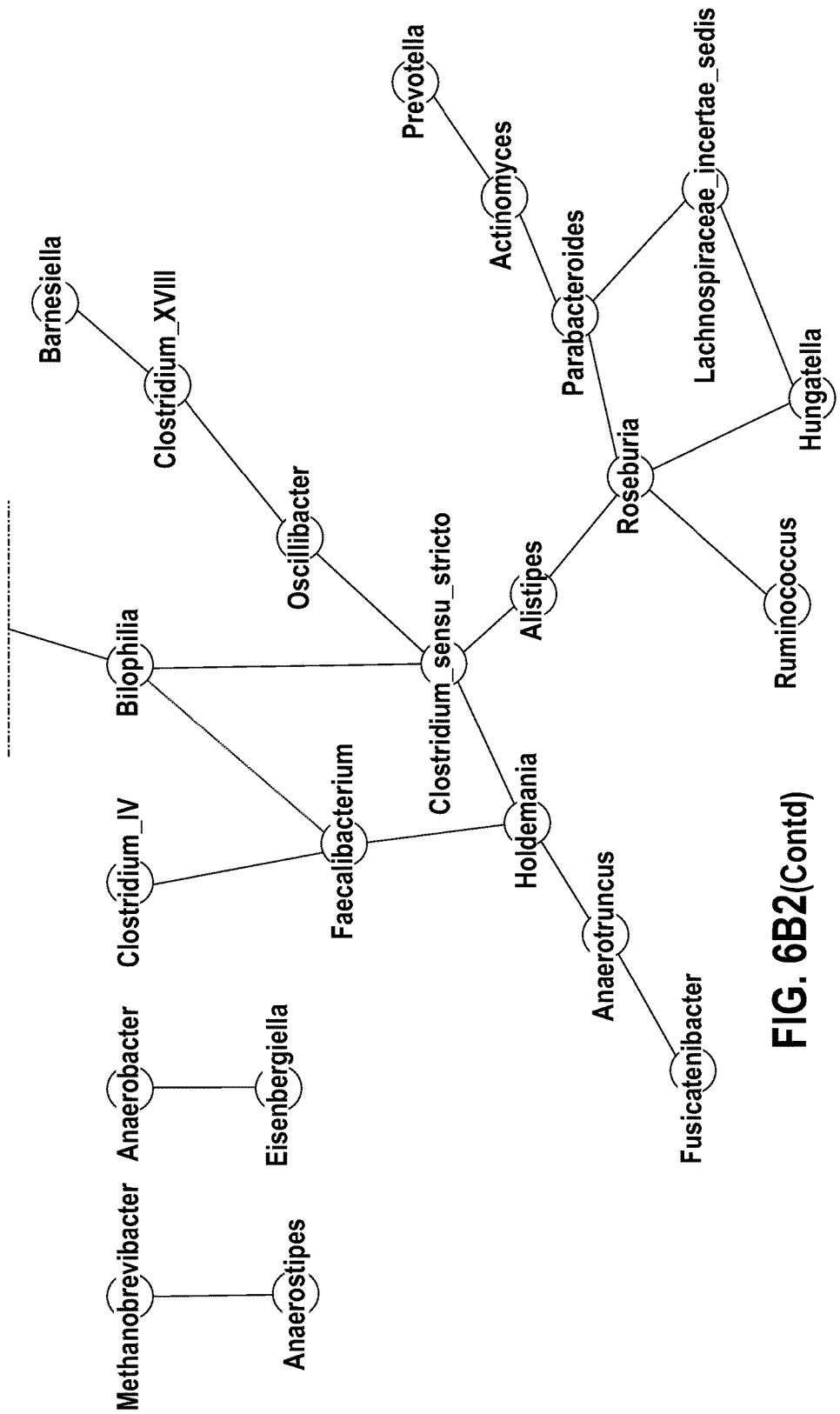
FIG. 6B2(Contd)
Day_16

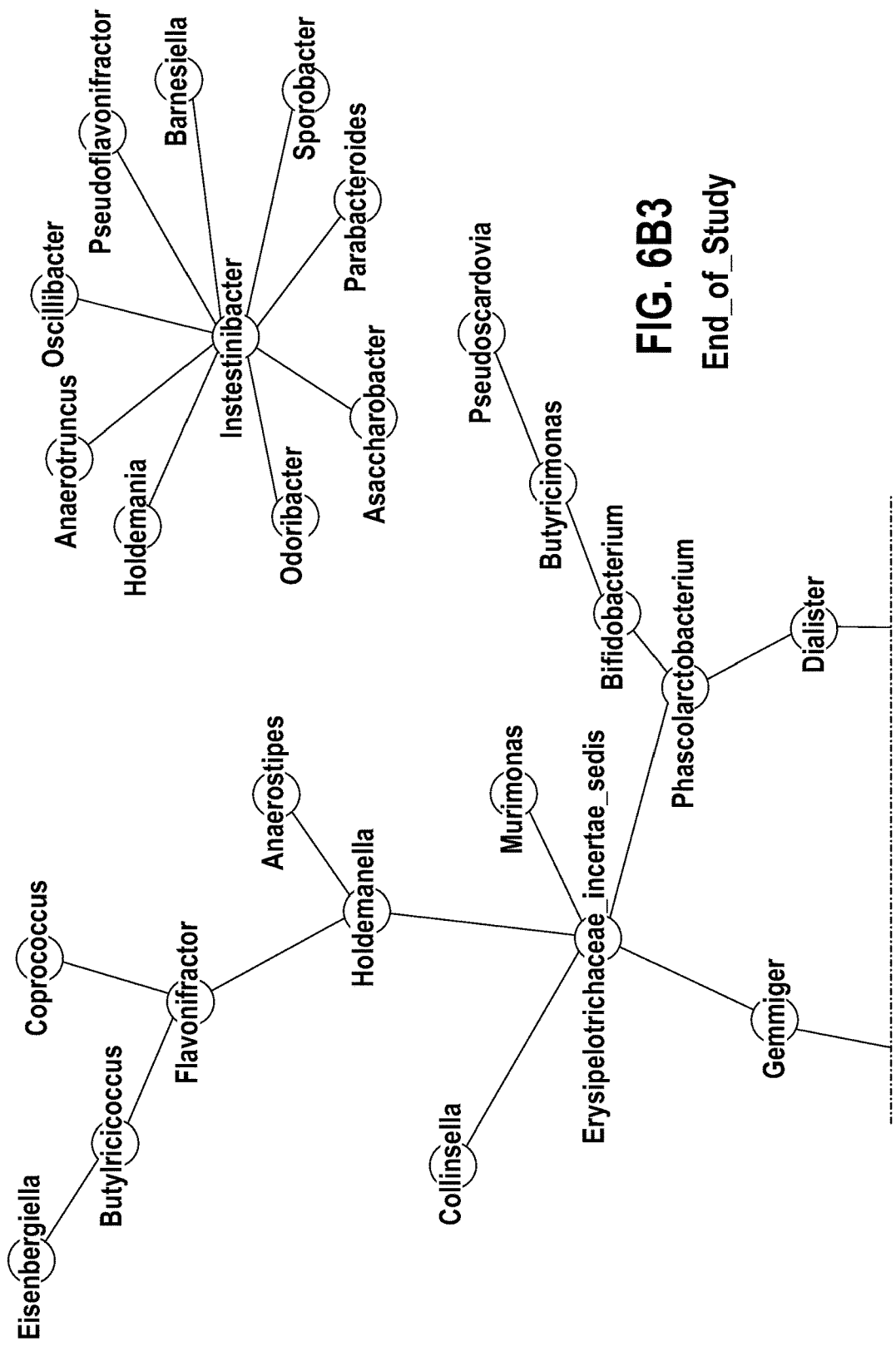
FIG. 6B3
End_of_Study

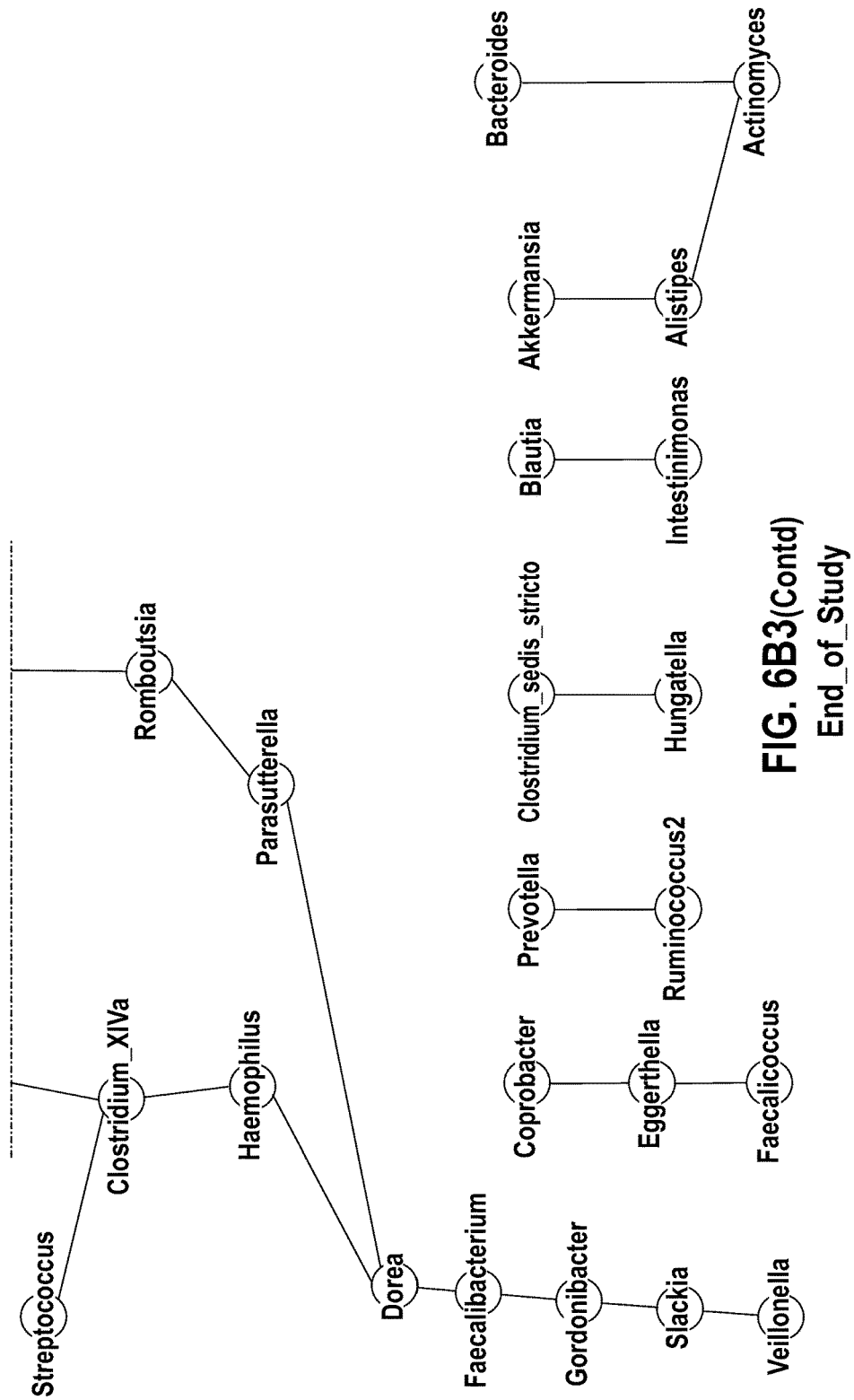
FIG. 6B3(Contd)
End_of_Study

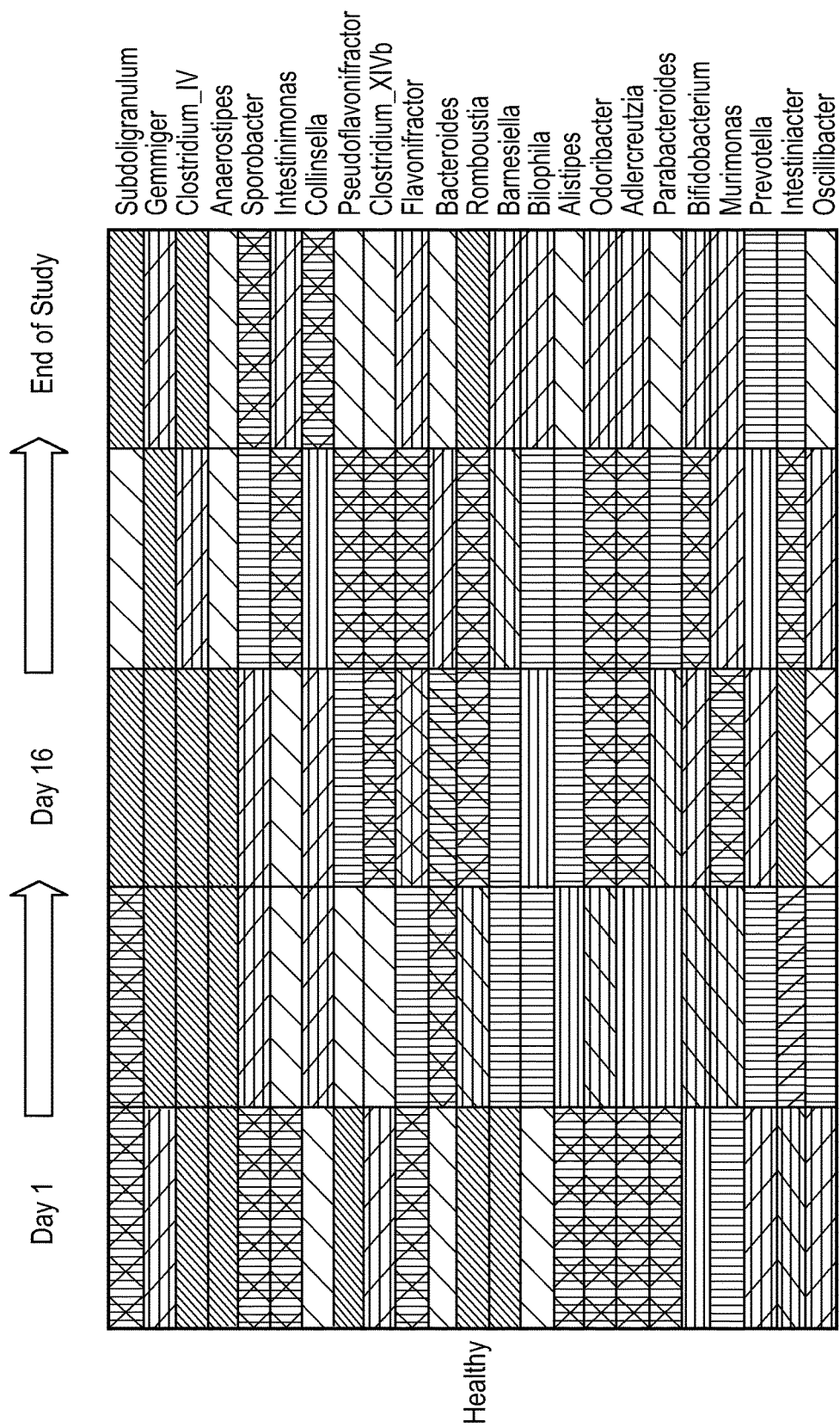
FIG. 7(Contd)

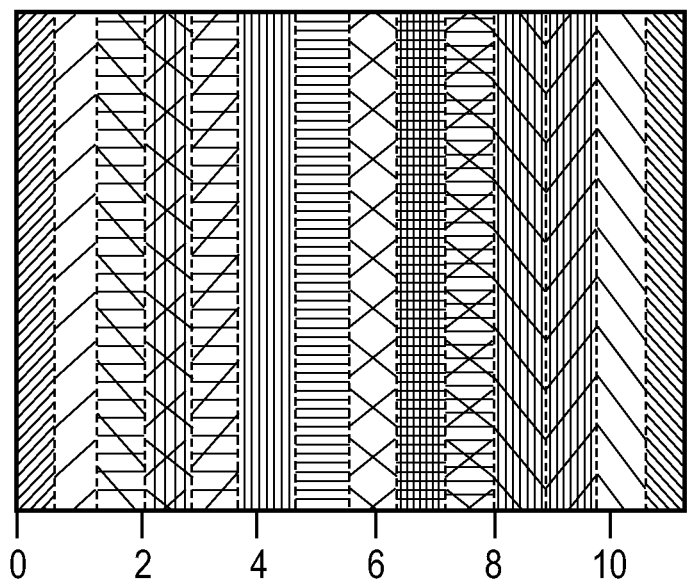
FIG. 7(Contd)

COMPOSITIONS COMPRISING BACTERIAL STRAINS

CROSS-REFERENCE

This application is a continuation of International Application No. PCT/GB2017/053722, filed Dec. 12, 2017, which claims the benefit of Great Britain Application No. 1621123.7, filed Dec. 12, 2016; all of which are hereby incorporated by reference in their entirety. Further, all publications, patents, and patent applications mentioned in this specification are herein incorporated by reference in their entirety to the same extent as if each individual publication, patent, or patent application was specifically and individually indicated to be incorporated by reference.

SEQUENCE LISTING

The instant application contains a Sequence Listing which has been submitted electronically in ASCII format and is hereby incorporated by reference in its entirety. Said ASCII copy, created on Dec. 7, 2017, is named p069516_sequence_listing.txt and is 12,288 bytes in size.

TECHNICAL FIELD

This invention is in the field of compositions comprising bacterial strains isolated from the mammalian digestive tract and the use of such compositions in the treatment of disease.

BACKGROUND TO THE INVENTION

The human intestine is thought to be sterile in utero, but it is exposed to a large variety of maternal and environmental microbes immediately after birth. Thereafter, a dynamic period of microbial colonization and succession occurs, which is influenced by factors such as delivery mode, environment, diet and host genotype, all of which impact upon the composition of the gut microbiota, particularly during early life. Subsequently, the microbiota stabilizes and becomes adult-like [1]. The human gut microbiota contains more than 1500 different phylotypes dominated in abundance levels by two major bacterial divisions (phyla), the Bacteroidetes and the Firmicutes [2]. The successful symbiotic relationships arising from bacterial colonization of the human gut have yielded a wide variety of metabolic, structural, protective and other beneficial functions. The enhanced metabolic activities of the colonized gut ensure that otherwise indigestible dietary components are degraded with release of by-products providing an important nutrient source for the host and additional health benefits. Similarly, the immunological importance of the gut microbiota is well-recognized and is exemplified in germfree animals which have an impaired immune system that is functionally reconstituted following the introduction of commensal bacteria [3-5].

Dramatic changes in microbiota composition have been documented in gastrointestinal disorders such as inflammatory bowel disease (IBD). For example, the levels of *Clostridium* cluster XIVa bacteria are reduced in IBD subjects whilst numbers of *E. coli* are increased, suggesting a shift in the balance of symbionts and pathobionts within the gut [6-9, 18].

In recognition of the potential positive effect that certain bacterial strains may have on the animal gut, various strains have been proposed for use in the treatment of various diseases (see, for example, [10-13]). A number of strains, including mostly *Lactobacillus* and *Bifidobacterium* strains, have been proposed for use in treating various bowel disorders (see [14] for a review and see [15]). Reference [16] proposes the use of strains of the genus *Blautia* for use in modulating the microbial balance of the digestive ecosystem. In the context of reference 16, modulation refers to promoting the activity of the acetogenic bacterial flora to the detriment of methanogenic and sulfur reducing bacteria. This document therefore teaches only an increase in acetogenic bacteria. There is no discussion relating to the diversity of species belonging to a number of taxa. Reference [17] discusses the use of *Blautia* for improving survival in patients affected by graft versus host disease (GVDH). It mentions that increased bacterial diversity is associated with reduced GVDH-related mortality and that increased amounts of bacteria of the *Blautia* genus were associated with reduced GVDH. However, there is no suggestion that the administration of *Blautia* to a patient effects an increase in microbiota diversity and/or induces stability of the microbiota in a subject.

The relationship between different bacterial strains and different diseases, and the precise effects of particular bacterial strains on the gut and at a systemic level and on any particular types of diseases, are poorly characterised and results to date are variable and pose more questions than provide answers [18].

A hallmark of many human diseases linked to microbiota alteration is loss of microbiota diversity. As distinct from so-called dysbiosis which is simply an altered microbiota composition compared to the typical aggregate microbiota in healthy subjects, loss of microbiota diversity may be quantified by a measurable reduction in number of the sequence-based bacterial classifications or Operational Taxonomic Units (OTUs) in a sample, typically determined by 16S rRNA amplicon sequencing methods. Loss of diversity is also measured by reductions in the Shannon Diversity Index, or the Chao index. Reduced microbiota diversity is reported in recent studies of obesity, inflammatory bowel disease (IBD), irritable bowel syndrome (IBS), type 2 diabetes and frailer older people [20]. Re-establishing the healthy microbiota can be difficult as the bacteria in the gut are resistant to colonisation. This poses a challenge when trying to treat the microbiota of unhealthy subjects by increasing the diversity of the microbiota [19]. The accompanying loss of microbial metabolic function is assumed to be a contributory factor to the symptoms of these pathophysiologies. In contrast to healthy adults in whom the microbiota is stable, the microbiota of unhealthy subjects such as those suffering IBD, IBS and frail elderly subjects is unstable [18, 20].

There is a requirement for the potential effects of gut bacteria to be characterised so that new therapies using gut bacteria can be developed.

SUMMARY OF THE INVENTION

The inventors have developed new therapies for treating and preventing diseases and disorders by increasing or maintaining the intestinal microbiota diversity in a subject. In particular, the inventors have identified that bacterial strains from the genus *Blautia* can be effective in increasing or maintaining the number and/or evenness of different types of bacteria in the distal gut of a subject. As described in the examples, oral administration of compositions comprising *Blautia hydrogenotrophica* increases the microbiota diversity in stool. This increase in diversity was seen in healthy and IBS subjects. However, IBS subjects receiving placebo had a statistically significant reduction in microbiome diversity during the course of the study. Additionally, the examples show that treatment with compositions comprising *Blautia hydrogenotrophica*, but not placebo, increased the stability of the microbiota in IBS subjects throughout the course of the study. The stability of the microbiota in subjects receiving the composition comprising *Blautia hydrogenotrophica* was comparable to that of healthy control subjects.

Therefore, in a first embodiment, the invention provides a composition comprising a bacterial strain of the genus *Blautia*, for use in a method of increasing or maintaining the microbiota diversity. Similarly, there is also provided a method of increasing or maintaining the microbiota diversity in a subject comprising use of a bacterial strain of the genus *Blautia*.

The term "increasing or maintaining the microbiota diversity" is used herein to mean increasing or maintaining the number of different types of bacteria and/or the evenness of the different types of bacteria in the microbiota of a subject. In some embodiments, the microbiota diversity is increased. In some embodiments, the number of different genera of bacteria in the microbiota is increased. In some embodiments, the number of different species of bacteria in the microbiota is increased. In some embodiments, the number of different strains of bacteria in the microbiota is increased. In some embodiments, the microbiota diversity is maintained. In some embodiments, the number of different genera of bacteria in the microbiota is maintained. In some embodiments, the number of different species of bacteria in the microbiota is maintained. In some embodiments, the number of different strains of bacteria in the microbiota is maintained. In some embodiments, the number of genera, species and strains in the microbiota is increased or maintained.

The increase in microbiotia diversity may be for non-acetogenic bacteria. It may also be for both acetogenic and non-acetogenic bacteria. Such bacteria are well known in the art. Briefly, acetogenic bacteria produce acetate as an end product of anaerobic respiration or fermentation.

In some embodiments, loss, increase or maintenance of microbiota diversity may be quantified by a measurable reduction, increase or maintenance, respectively, in the number of the sequence-based bacterial classifications or Operational Taxonomic Units (OTUs) in a sample, typically determined by 16S rRNA amplicon sequencing methods. In some embodiments, loss of diversity may be measured by reductions in the Shannon Diversity Index, or the Chao index. Conversely, in some embodiments, an increase of diversity may be measured by an increase in the Shannon Diversity Index, or the Chao index. Similarly, in some embodiments, maintenance of diversity may be measured by the same result in the Shannon Diversity Index, or the Chao index.

In some embodiments, the evenness of the different types of bacteria is increased. In some embodiments, the relative abundance of the different types of bacteria in the microbiota becomes more even following treatment or prevention with a composition of the invention.

The inventors have also developed new therapies for treating and preventing diseases and disorders by inducing stability of the intestinal microbiota. In particular, the inventors have identified that bacterial strains from the genus *Blautia* induce stability of the intestinal microbiota. By "induce stability" is meant that the microbiota diversity remains stable and also the relative numbers of the different Genus in the microbiota remains stable. This is important as a number of diseases and disorders, including IBS and IBD, are characterised by reduced stability of the microbiota. As described in the examples, oral administration of compositions comprising *Blautia hydrogenotrophica* induces stability of the microbiota in stool. Therefore, in a further embodiment, the invention provides a composition comprising a bacterial strain of the genus *Blautia*, for use in a method of inducing stability of the microbiota in a subject. Similarly, there is also provided a method of inducing stability of the microbiota in a subject comprising use of a bacterial strain of the genus *Blautia*.

In some embodiments, the relative numbers of the different bacterial species in the microbiota of a subject becomes more stable following treatment or prevention with a composition of the invention, for example in a subject diagnosed with a disease or disorder characterised by a reduction in the diversity of microbiota. In some embodiments, the relative numbers of the different bacterial Genus in the microbiota of a subject becomes more stable following treatment or prevention with a composition of the invention, for example in a subject diagnosed with a disease or disorder characterised by a reduction in the diversity of microbiota. The stability of a subject's microbiota can be assessed by comparing the microbiome from the subject at two different time points. If there is a difference in the microbiome, this can be indicative of disease or of a disorder being present. In some embodiments, the two different time points are at least three days apart (e.g. at least 1 week, 2 weeks, 1 month, 3 months, 6 months, 1 year, 2 years apart). In some embodiments, the two different time points are 3-7 days apart, 1-2 weeks apart, 2-4 weeks apart, 4-8 weeks apart, 8-24 weeks apart, 24-40 weeks apart, 40-52 weeks apart or more than 52 weeks apart. In some embodiments, more than two different time points are used, e.g. three, four, five or more than five time points. Suitable intervals are chosen between the various time points, for example, as set out above.

In preferred embodiments of all aspects of the invention, the bacterial strain is of *Blautia hydrogenotrophica* and is preferably the bacterium deposited under accession number DSM 10507/14294.

In some embodiments, the microbiota diversity and/or the stability of the microbiota refers to the microbiota diversity and/or the stability in stool in the subject. In some embodiments, the microbiota diversity and/or the stability of the microbiota refers to the microbiota diversity and/or the stability in a stool sample from the subject. In some embodiments, the microbiota diversity and/or the stability of the microbiota refers to the microbiota diversity and/or the stability in the distal gut of the subject. In some embodiments, the microbiota diversity and/or the stability of the microbiota refers to the microbiota diversity and/or the stability in the gastrointestinal tract of the subject. In some embodiments, the microbiota diversity and/or the stability of the microbiota refers to the microbiota diversity and/or the stability in the caecum. In some embodiments, the microbiota diversity and/or the stability of the microbiota refers to the microbiota diversity and/or the stability in the colon.

In some embodiments, the invention provides a composition comprising a bacterial strain of the genus *Blautia*, for use in a method of treating or preventing a disease or disorder associated with a level of microbiota diversity that is reduced relative to the microbiota diversity of a healthy subject. In some embodiments, the treatment or prevention using a composition of the invention results in the microbiota diversity increasing to the levels present in a healthy individual. In some embodiments, treatment or prevention using a composition of the invention results in the microbiota diversity increasing to levels greater than those present in some healthy individuals. In some embodiments, the healthy individual is of a similar/same age to the subject and/or is of a similar/same race to the subject. Similarly, the invention also provides a method of treatment or prevention of a disease or disorder associated with a level of microbiota diversity that is reduced relative to the microbiota diversity of a healthy subject wherein the method comprises administering a composition comprising a bacterial strain of the genus *Blautia*. Examples of diseases or disorders associated with a reduced level of microbiota diversity include but are not limited to: IBS, IBD [21], obesity [22], type 2 diabetes, infectious diseases, allergic diseases, autoimmune diseases and metabolic diseases/disorders. Treatment or prevention of these diseases and disorders is encompassed by the invention. In some embodiments, the disease or disorder is IBS.

In some embodiments, the subject is an infant or child with a reduced microbiota diversity compared to a healthy infant or child, respectively. It has been observed that some children who develop an allergic disease later in life have a reduced diversity of faecal microbiota as 1 week old infants [23]. Thus, in some embodiments, the infant is less than 1 week old, is less than 2 weeks old, is less than one month old, is less than two months old or is less than four months old. In some embodiments, the subject is an infant who has not been delivered via a vaginal birth. For example, in some embodiments, the subject is an infant who has been delivered by Caesarean section. Reduced microbiota diversity has also been reported in frail elderly subjects. In some embodiments, therefore, the subject is an elderly subject, for example, a frail elderly subject. In some embodiments, the subject is 65 or more years in age (e.g. 70 or more, 75 or more, 80 or more, 85 or more or 90 or more years in age) [20].

It has been estimated that a single human individual has approximately 101 different bacterial species and 195 different strains in its microbiota [24]. Accordingly, in some embodiments, the composition is for use in treating a subject having less than 101 different bacterial species (e.g. less than 100, 99, 98, 97, 96, 95, 94, 93, 92, 91, 90, 85, 80, 75 or 70 bacterial species) and/or less than 195 different strains (e.g. less than 194, 193, 192, 191, 190, 189, 188, 187, 186, 185, 183, 180, 175, 170, 165, 160, 150, 140 bacterial strains) in its microbiota. In some embodiments, the treatment or prevention results in the microbiota diversity increasing to more than 80 bacterial species (e.g. more than 85, 90, 91, 92, 93, 94, 95, 96, 97, 98, 99 or 100 bacterial species) or to 101 bacterial species. For example, in some embodiments, the treatment or prevention results in the microbiota diversity increasing to more than 90 bacterial species. For example, in some embodiments, the treatment or prevention results in the microbiota diversity increasing to more than 95 bacterial species. For example, in some embodiments, the treatment or prevention results in the microbiota diversity increasing to more than 97 bacterial species. For example, in some embodiments, the treatment or prevention results in the microbiota diversity increasing to more than 99 bacterial species. In some embodiments, the treatment or prevention results in the microbiota diversity increasing to more than 160 bacterial strains (e.g. more than 165, 170, 185, 186, 187, 188, 189, 190, 191, 192, 193 or 194 bacterial species) or to 195 bacterial strains. For example, in some embodiments, the treatment or prevention results in the microbiota diversity increasing to more than 175 bacterial strains. For example, in some embodiments, the treatment or prevention results in the microbiota diversity increasing to more than 185 bacterial strains. For example, in some embodiments, the treatment or prevention results in the microbiota diversity increasing to more than 190 bacterial strains.

In some embodiments, the treatment or prevention results in the microbiota diversity increasing by at least one bacterial genus (e.g. by at least two, three, four, five, six, seven, eight, nine or ten bacterial genera). In some embodiments, the treatment or prevention results in the microbiota diversity increasing by at least one bacterial species (e.g. by at least two, three, four, five, six, seven, eight, nine, ten, 12, 15, 17 or 20 bacterial species). In some embodiments, the treatment or prevention results in the microbiota diversity increasing by at least one bacterial strain (e.g. by at least two, three, four, five, six, seven, eight, nine, ten, 12, 15, 17, 20 or 25 bacterial strains).

In some embodiments, the invention provides a composition comprising a bacterial strain of the genus *Blautia*, for use in a method of treating or preventing a disease or disorder associated with reduced stability of the microbiota compared to the stability of the microbiota in a healthy subject (or compared to a population of healthy subjects). By "reduced stability of the microbiota" is meant that the microbiota diversity does not remain as stable and also the relative numbers of the different Genus in the microbiota do not remain as stable as the stability observed in a healthy subject or in a population of healthy subjects. In some embodiments, inducing stability of the microbiota results in the stability being induced to a similar level as is present in a healthy subject, or in a population of healthy subjects. In some embodiments, inducing stability of the microbiota results in the stability being induced to the same level as is present in a healthy subject, or in a population of healthy subjects. Similarly, the invention provides a method of treating or preventing a disease or disorder associated with reduced stability of the microbiota wherein the method comprises administering a composition comprising a bacteria strain of the genus *Blautia*. For example, the pathogenesis of some diseases or disorders is characterised by reduced stability of the microbiota. Examples of such diseases and disorders are IBS, IBD, diabetes (e.g. type 2 diabetes), allergic diseases, autoimmune diseases and metabolic diseases/disorders. Accordingly, in some embodiments, the invention provides a composition comprising a bacterial strain of the genus *Blautia*, for use in a method of treating or preventing a disease or disorder associated with reduced stability of the microbiota, wherein the treatment or prevention comprises inducing stability of the microbiota. In some embodiments, the disease or disorder is selected from IBS, IBD, diabetes (e.g. type 2 diabetes), allergic diseases, autoimmune diseases and metabolic diseases/disorders. In some embodiments, the disease or disorder is IBS or IBD. In some embodiments, the disease or disorder is IBS. Accordingly, in some embodiments, the invention provides a composition comprising a bacterial strain of the genus *Blautia*, for use in a method of treating or preventing IBS or IBD, wherein the treatment or prevention comprises inducing stability of the microbiota.

In some embodiments, the invention provides a method of treatment or prevention of a disease or disorder associated with a level of microbiota diversity that is reduced relative to the microbiota diversity of a healthy subject wherein the method comprises diagnosing a subject as having a reduced level of microbiota diversity and then if a reduced level of diversity is found to be present, administering a composition comprising a bacterial strain of the genus *Blautia* to the subject.

In some embodiments, the invention provides a method of treatment or prevention of a disease or disorder associated with reduced stability of microbiota relative to the stability of microbiota in a healthy subject wherein the method comprises diagnosing a subject as having reduced stability of microbiota and then if reduced stability is found to be present, administering a composition comprising a bacterial strain of the genus *Blautia* to the subject.

In preferred embodiments of the invention, the bacterial strain in the composition is of *Blautia hydrogenotrophica*. Closely related strains may also be used, such as bacterial strains that have a 16s rRNA sequence that is at least 97%, 98%, 99%, 99.5% or 99.9% identical to the 16s rRNA sequence of a bacterial strain of *Blautia hydrogenotrophica*. Preferably, the bacterial strain has a 16s rRNA sequence that is at least 97%, 98%, 99%, 99.5% or 99.9% identical to SEQ ID NO:5. Preferably, the bacterial strain has the 16s rRNA sequence of SEQ ID NO:5. Most preferably, the bacterial strain in the composition is the *Blautia hydrogenotrophica* strain deposited under accession number DSM 10507/14294.

In further embodiments of the invention, the bacterial strain in the composition is of *Blautia stercoris*. Closely related strains may also be used, such as bacterial strains that have a 16s rRNA sequence that is at least 97%, 98%, 99%, 99.5% or 99.9% identical to the 16s rRNA sequence of a bacterial strain of *Blautia stercoris*. Preferably, the bacterial strain has a 16s rRNA sequence that is at least 97%, 98%, 99%, 99.5% or 99.9% identical to SEQ ID NO:1 or 3. Preferably, the sequence identity is to SEQ ID NO:3. Preferably, the bacterial strain for use in the invention has the 16s rRNA sequence represented by SEQ ID NO:3.

In further embodiments of the invention, the bacterial strain in the composition is of *Blautia wexlerae*. Closely related strains may also be used, such as bacterial strains that have a 16s rRNA sequence that is at least 97%, 98%, 99%, 99.5% or 99.9% identical to the 16s rRNA sequence of a bacterial strain of *Blautia wexlerae*. Preferably, the bacterial strain has a 16s rRNA sequence that is at least 97%, 98%, 99%, 99.5% or 99.9% identical to SEQ ID NO:2 or 4. Preferably, the sequence identity is to SEQ ID NO:4. Preferably, the bacterial strain for use in the invention has the 16s rRNA sequence represented by SEQ ID NO:4.

In certain embodiments, the composition of the invention is for oral administration. Oral administration of the strains of the invention can be effective for increasing the microbiota diversity and/or inducing the stability of the microbiota. Also, oral administration is convenient for subjects and practitioners and allows delivery to and/or partial or total colonisation of the intestine.

In certain embodiments, the composition of the invention comprises one or more pharmaceutically acceptable excipients or carriers.

In certain embodiments, the composition of the invention comprises a bacterial strain that has been lyophilised. Lyophilisation is an effective and convenient technique for preparing stable compositions that allow delivery of bacteria, and is shown to provide effective compositions in the examples.

In certain embodiments, the invention provides a food product comprising the composition as described above.

In certain embodiments, the invention provides a vaccine composition comprising the composition as described above.

Additionally, the invention provides a method of increasing the microbiota diversity and/or inducing the stability of the microbiota and thereby treating or preventing diseases or disorders associated with a reduced microbiota diversity and/or with reduced stability of the microbiota, comprising administering a composition comprising a bacterial strain of the genus *Blautia*.

BRIEF DESCRIPTION OF DRAWINGS

FIG. 2: Comparison of microbiota diversity between Day 16 and Day 1 for healthy and IBS patients after treatment with BlautiX or placebo.

FIGS. 3A-3B: FIG. 3A) Interconnectivity of the microbiome in healthy patients at Day 1, Day 16 and end of study after BlautiX treatment, FIG. 3B) Interconnectivity of the microbiome in IBS patients at Day 1, Day 16 and end of study after BlautiX treatment. The interconnectivity results seen on Day 1, Day 16 and at the End of Study for healthy individuals that are presented in FIG. 3A are also shown in FIGS. 3A1, 3A2 and 3A3, respectively. The interconnectivity results seen on Day 1, Day 16 and at the End of Study for IBS patients that are presented in FIG. 3B are also shown in FIGS. 3B1, 3B2 and 3B3, respectively.

FIGS. 4A-4C: A comparison of the instability in microbiota profiles in healthy and IBS patients after treatment with BlautiX or placebos at FIG. 4A) Day 16 and Day 1, FIG. 4B) end of study and Day 1 and FIG. 4C) end of study and Day 16.

FIGS. 6A-6B: FIG. 6A) The mutual exclusion network in healthy patients at Day 1, Day 16 and end of study after BlautiX treatment, FIG. 6B) The mutual exclusion network in IBS patients at Day 1, Day 16 and end of study after BlautiX treatment. The mutual exclusion results seen on Day 1, Day 16 and at the End of Study for healthy individuals that are presented in FIG. 6A are also shown in FIGS. 6A1, 6A2 and 6A3, respectively. The mutual exclusion results seen on Day 1, Day 16 and at the End of Study for IBS patients that are presented in FIG. 6B are also shown in FIGS. 6B1, 6B2 and 6B3, respectively.

(FIG. 9A) Visualization of microbiota profiles of different groups at D-14 using PCoA based on Bray-Curtis dissimilarities. (FIG. 9B) Visualization of microbiota profiles of the groups at D14 using PCoA based on Bray-Curtis dissimilarities. (FIG. 9C) Significant difference (p-value=0.002) in the microbiota profiles for the Blautix group was seen across the timepoints.

DISCLOSURE OF THE INVENTION

Bacterial Strains

Figure 1:
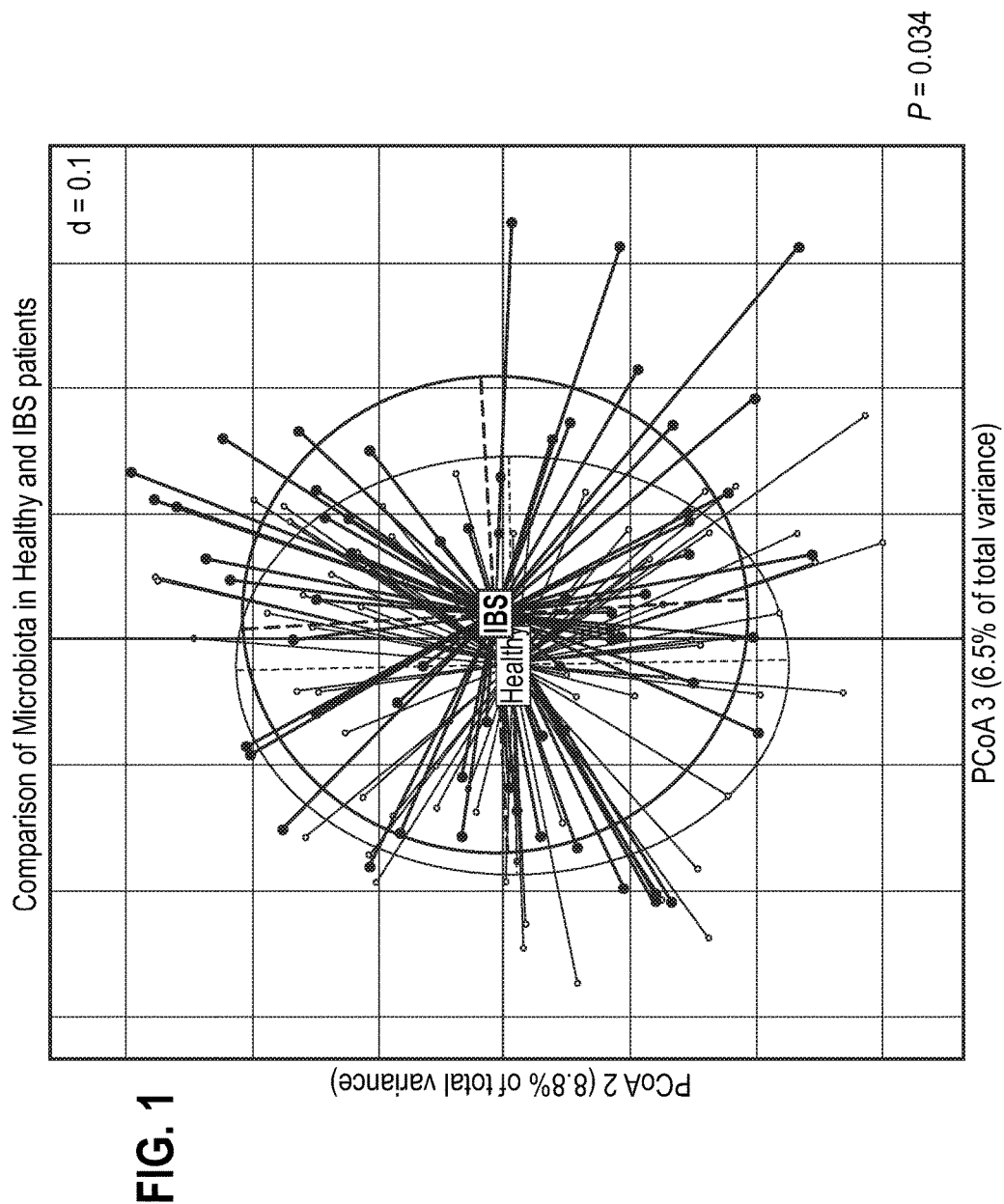
FIG. 1: Comparison of microbiota in healthy and IBS patients.

The compositions of the invention comprise a bacterial strain of the genus *Blautia*. The examples demonstrate that bacteria of this genus are useful for increasing the microbiota diversity and/or inducing the stability of the microbiota. The preferred bacterial strains are of the species *Blautia hydrogenotrophica*, *Blautia stercoris* and *Blautia* wexlerae. Most preferred is *Blautia hydrogenotrophica*, particularly the bacterium deposited under accession number DSM 10507/14294.

Examples of *Blautia* strains for use in the invention include *Blautia hydrogenotrophica*, *B. stercoris*, *B. faecis*, *B. coccoides*, *B. glucerasea*, *B. hansenii*, *B. luti*, *B. producta*, *B. schinkii* and *B. wexlerae*. The *Blautia* species are Gram-reaction-positive, non-motile bacteria that may be either coccoid or oval and all are obligate anaerobes that produce acetic acid as the major end product of glucose fermentation [25]. *Blautia* may be isolated from the human gut, although *B. producta* was isolated from a septicaemia sample.

*Blautia hydrogenotrophica* (previously known as *Ruminococcus hydrogenotrophicus*) has been isolated from the guts of mammals, is strictly anaerobic, and metabolises $H_2/CO_2$ to acetate, which may be important for human nutrition and health. The type strain of *Blautia hydrogenotrophica* is S5a33=DSM 10507=JCM 14656. The GenBank accession number for the 16S rRNA gene sequence of *Blautia hydrogenotrophica* strain S5a36 is X95624.1 (disclosed herein as SEQ ID NO:5). This exemplary *Blautia hydrogenotrophica* strain is described in [25] and [26]. The S5a33 strain and the S5a36 strain correspond to two subclones of an acetogenic strain isolated from a faecal sample of a healthy subject. They show identical morphology, physiology and metabolism and have identical 16S rRNA sequences. Thus, in some embodiments, the *Blautia hydrogenotrophica* for use in the invention has the 16S rRNA sequence of SEQ ID NO:5.

The *Blautia hydrogenotrophica* bacterium deposited under accession number DSM 10507 and also under accession number DSM 14294 was tested in the examples and is also referred to herein as strain BH. Strain BH was deposited with the Deutsche Sammlung von Mikroorganismen [German Microorganism Collection] (Mascheroder Weg 1b, 38124 Braunschweig, Germany) on 10 May 2001 as "*Ruminococcus hydrogenotrophicus*" under accession number DSM 10507 and also under accession number DSM 14294. The depositor was INRA Laboratoire de Microbiologie CR de Clermont-Ferrand/Theix 63122 Saint Genes Champanelle, France. Ownership of the bacterium deposited as DSM 10507 and DSM 14294 has passed via assignment to 4 D Pharma Plc. The DSM 14294 deposit was made under the terms of the Budapest Treaty. Maintenance of a viable culture is assured for 30 years from the date of deposit. All restrictions on the availability to the public of the microorganisms deposited as DSM 10507 and 14294 will be irrevocably removed upon the granting of a patent for this application.

The GenBank accession number for the 16S rRNA gene sequence of *Blautia stercoris* strain GAM6-1$^T$ is HM626177 (disclosed herein as SEQ ID NO:1). An exemplary *Blautia stercoris* strain is described in [27]. The type strain of *Blautia wexlerae* is WAL 14507=ATCC BAA-1564=DSM 19850 [25]. The GenBank accession number for the 16S rRNA gene sequence of *Blautia wexlerae* strain WAL 14507 T is EF036467 (disclosed herein as SEQ ID NO:2). This exemplary *Blautia wexlerae* strain is described in [25].

A preferred *Blautia stercoris* strain is the strain deposited under accession number NCIMB 42381, which is also referred to herein as strain 830. A 16S rRNA sequence for the 830 strain is provided in SEQ ID NO:3. Strain 830 was deposited with the international depositary authority NCIMB, Ltd. (Ferguson Building, Aberdeen, AB21 9YA, Scotland) by GT Biologics Ltd. (Life Sciences Innovation Building, Aberdeen, AB25 2ZS, Scotland) on 12 Mar. 2015 as "*Blautia stercoris* 830" and was assigned accession number NCIMB 42381. GT Biologics Ltd. subsequently changed its name to 4 D Pharma Research Limited. The NCIMB 42381 deposit was made under the terms of the Budapest Treaty. Maintenance of a viable culture is assured for 30 years from the date of deposit. All restrictions on the availability to the public of the deposited microorganism will be irrevocably removed upon the granting of a patent for this application.

A preferred *Blautia wexlerae* strain is the strain deposited under accession number NCIMB 42486, which is also referred to herein as strain MRX008. A 16S rRNA sequence for the MRX008 strain is provided in SEQ ID NO:4. Strain MRX008 was deposited with the international depositary authority NCIMB, Ltd. (Ferguson Building, Aberdeen, AB21 9YA, Scotland) by 4 D Pharma Research Ltd. (Life Sciences Innovation Building, Aberdeen, AB25 2ZS, Scotland) on 16 Nov. 2015 as "*Blautia* Ruminococcus" and was assigned accession number NCIMB 42486. The NCIMB 42486 deposit was made under the terms of the Budapest Treaty. Maintenance of a viable culture is assured for 30 years from the date of deposit. All restrictions on the availability to the public of the deposited microorganism will be irrevocably removed upon the granting of a patent for this application.

Bacterial strains closely related to the strain tested in the examples are also expected to be effective for increasing the microbiota diversity and/or inducing the stability of the microbiota. In certain embodiments, the bacterial strain for use in the invention has a 16s rRNA sequence that is at least 97%, 98%, 99%, 99.5% or 99.9% identical to the 16s rRNA sequence of a bacterial strain of *Blautia hydrogenotrophica*. Preferably, the bacterial strain for use in the invention has a 16s rRNA sequence that is at least 97%, 98%, 99%, 99.5% or 99.9% identical to SEQ ID NO:5. Preferably, the bacterial strain for use in the invention has a 16s rRNA sequence that has the sequence of SEQ ID NO:5.

In certain embodiments, the bacterial strain for use in the invention has a 16s rRNA sequence that is at least 97%, 98%, 99%, 99.5% or 99.9% identical to the 16s rRNA sequence of a bacterial strain of *Blautia stercoris*. Preferably, the bacterial strain for use in the invention has a 16s rRNA sequence that is at least 97%, 98%, 99%, 99.5% or 99.9% identical to SEQ ID NO:1 or SEQ ID NO:3. Preferably, the sequence identity is to SEQ ID NO:3. Preferably, the bacterial strain for use in the invention has the 16s rRNA sequence represented by SEQ ID NO:3. In certain embodiments, the bacterial strain for use in the invention has a 16s rRNA sequence that is at least 97%, 98%, 99%, 99.5% or 99.9% identical to the 16s rRNA sequence of a bacterial strain of *Blautia wexlerae*. Preferably, the bacterial strain for use in the invention has a 16s rRNA sequence that is at least 97%, 98%, 99%, 99.5% or 99.9% identical to SEQ ID NO:2 or SEQ ID NO:4. Preferably, the sequence identity is to SEQ ID NO:4. Preferably, the bacterial strain for use in the invention has the 16s rRNA sequence represented by SEQ ID NO:4.

Bacterial strains that are biotypes of the bacterium deposited under accession number DSM 10507/14294 or biotypes of the bacteria deposited under accession numbers NCIMB 42381 and NCIMB 42486 are also expected to be effective for increasing the microbiota diversity and/or inducing the stability of the microbiota. A biotype is a closely related strain that has the same or very similar physiological and biochemical characteristics.

Strains that are biotypes of a bacterium deposited under accession number DSM 10507/14294, NCIMB 42381 or NCIMB 42486 and that are suitable for use in the invention may be identified by sequencing other nucleotide sequences for a bacterium deposited under accession number DSM 10507/14294, NCIMB 42381 or NCIMB 42486. For example, substantially the whole genome may be sequenced and a biotype strain for use in the invention may have at least 97%, 98%, 99%, 99.5% or 99.9% sequence identity across at least 80% of its whole genome (e.g. across at least 85%, 90%, 95% or 99%, or across its whole genome). For example, in some embodiments, a biotype strain has at least 98% sequence identity across at least 98% of its genome or at least 99% sequence identity across 99% of its genome. Other suitable sequences for use in identifying biotype strains may include hsp60 or repetitive sequences such as BOX, ERIC, (GTG)$_5$, or REP or [28]. Biotype strains may have sequences with at least 97%, 98%, 99%, 99.5% or 99.9% sequence identity to the corresponding sequence of a bacterium deposited under accession number DSM 10507/14294, NCIMB 42381 or NCIMB 42486. In some embodiments, a biotype strain has a sequence with at least 97%, 98%, 99%, 99.5% or 99.9% sequence identity to the corresponding sequence of the *Blautia hydrogenotrophica* strain deposited under accession number DSM 10507/14294 and comprises a 16S rRNA sequence that is at least 99% identical (e.g. at least 99.5% or at least 99.9% identical) to SEQ ID NO:5. In some embodiments, a biotype strain has a sequence with at least 97%, 98%, 99%, 99.5% or 99.9% sequence identity to the corresponding sequence of the *Blautia hydrogenotrophica* strain deposited under accession number DSM 10507/14294 and has the 16S rRNA sequence of SEQ ID NO:5.

Alternatively, strains that are biotypes of a bacterium deposited under accession number DSM 10507/14294, NCIMB 42381 or NCIMB 42486 and that are suitable for use in the invention may be identified by using the accession number DSM 10507/14294 deposit, the accession number NCIMB 42381 deposit, or the accession number NCIMB 42486 deposit, and restriction fragment analysis and/or PCR analysis, for example by using fluorescent amplified fragment length polymorphism (FAFLP) and repetitive DNA element (rep)-PCR fingerprinting, or protein profiling, or partial 16S or 23s rDNA sequencing. In preferred embodiments, such techniques may be used to identify other *Blautia hydrogenotrophica*, *Blautia stercoris* or *Blautia wexlerae* strains.

In certain embodiments, strains that are biotypes of a bacterium deposited under accession number DSM 10507/14294, NCIMB 42381 or NCIMB 42486 and that are suitable for use in the invention are strains that provide the same pattern as a bacterium deposited under accession number DSM 10507/14294, NCIMB 42381 or NCIMB 42486 when analysed by amplified ribosomal DNA restriction analysis (ARDRA), for example when using Sau3AI restriction enzyme (for exemplary methods and guidance see, for example, [29]). Alternatively, biotype strains are identified as strains that have the same carbohydrate fermentation patterns as a bacterium deposited under accession number DSM 10507/14294, NCIMB 42381 or NCIMB 42486.

Other *Blautia* strains that are useful in the compositions and methods of the invention, such as biotypes of a bacterium deposited under accession number DSM 10507/14294, NCIMB 42381 or NCIMB 42486, may be identified using any appropriate method or strategy, including the assays described in the examples. For instance, strains for use in the invention may be identified by culturing bacteria and administering to rats to test in the distension assay. In particular, bacterial strains that have similar growth patterns, metabolic type and/or surface antigens to a bacterium deposited under accession number DSM 10507/14294, NCIMB 42381 or NCIMB 42486 may be useful in the invention. A useful strain will have comparable microbiota modulatory activity to the DSM 10507/14294, NCIMB 42381 or NCIMB 42486 strain. In particular, a biotype strain will elicit comparable effects on the microbiota to the effects shown in the Examples, which may be identified by using the culturing and administration protocols described in the Examples.

A particularly preferred strain of the invention is the *Blautia hydrogenotrophica* strain deposited under accession number DSM 10507/14294. This is the exemplary BH strain tested in the examples and shown to be effective for increasing the microbiota diversity and/or inducing the stability of the microbiota. Therefore, the invention provides a cell, such as an isolated cell, of the *Blautia hydrogenotrophica* strain deposited under accession number DSM 10507/14294, or a derivative thereof, for use in therapy, in particular for the diseases and disorders described herein.

A derivative of the strain deposited under accession number DSM 10507/14294, NCIMB 42381 or NCIMB 42486 may be a daughter strain (progeny) or a strain cultured (subcloned) from the original. A derivative of a strain of the invention may be modified, for example at the genetic level, without ablating the biological activity. In particular, a derivative strain of the invention is therapeutically active. A derivative strain will have comparable microbiota modulatory activity to the original DSM 10507/14294, NCIMB 42381 or NCIMB 42486 strain. In particular, a derivative strain will elicit comparable effects on the microbiota to the effects shown in the Examples, which may be identified by using the culturing and administration protocols described in the Examples. A derivative of the DSM 10507/14294 strain will generally be a biotype of the DSM 10507/14294 strain. A derivative of the NCIMB 42381 strain will generally be a biotype of the NCIMB 42381 strain. A derivative of the NCIMB 42486 strain will generally be a biotype of the NCIMB 42486 strain.

References to cells of the *Blautia hydrogenotrophica* strain deposited under accession number DSM 10507/14294 encompass any cells that have the same safety and therapeutic efficacy characteristics as the strains deposited under accession number DSM 10507/14294, and such cells are encompassed by the invention. References to cells of the *Blautia stercoris* strain deposited under accession number NCIMB 42381 encompass any cells that have the same safety and therapeutic efficacy characteristics as the strains deposited under accession number NCIMB 42381, and such cells are encompassed by the invention. References to cells of the *Blautia wexlerae* strain deposited under accession number NCIMB 42486 encompass any cells that have the same safety and therapeutic efficacy characteristics as the strains deposited under accession number NCIMB 42486, and such cells are encompassed by the invention.

In preferred embodiments, the bacterial strains in the compositions of the invention are viable and capable of partially or totally colonising the intestine.

Therapeutic Uses

In certain embodiments, the compositions of the invention are for use in increasing the microbiota diversity and/or inducing the stability of the microbiota. Reduced diversity of the microbiota and/or reduced stability of the microbiota are associated with numerous pathological diseases and disorders, and the examples demonstrate that the compositions of the invention may be effective for increasing the microbiota diversity and/or inducing the stability of the microbiota. Accordingly, the disease or disorder to be treated or prevented using a composition of the invention is preferably a disease or disorder associated with a level of microbiota diversity that is reduced relative to the microbiota diversity of a healthy subject and/or a disease or disorder that is associated with reduced stability of the microbiota. Thus, in some embodiments, the disease or disorder may be associated with a level of microbiota diversity that is reduced relative to the microbiota diversity of a healthy subject and also be associated with reduced stability of the microbiota.

In certain embodiments, the compositions of the invention are for use in treating or preventing a disease or disorder selected from IBS, IBD, obesity, type 2 diabetes, one or more infectious diseases, one or more allergic diseases, one or more autoimmune diseases and one or more metabolic diseases/disorders. Treatment or prevention of other diseases and disorders is also envisaged. In certain embodiments, the compositions of the invention are for use in treating or preventing IBS or IBD. In certain embodiments, the compositions of the invention are for use in treating or preventing IBS. In certain embodiments, the compositions of the invention are for use in treating or preventing IBD. In certain embodiments, the compositions of the invention are for use in treating or preventing one or more allergic diseases. In certain embodiments, the compositions of the invention are for use in treating or preventing obesity. In certain embodiments, the compositions of the invention are for use in treating or preventing one or more infectious diseases. In certain embodiments, the compositions of the invention are for use in treating or preventing one or more autoimmune diseases. In certain embodiments, the compositions of the invention are for use in treating or preventing one or more metabolic diseases/disorders. Preferably, the treatment or prevention comprises increasing the microbiota diversity and/or inducing the stability of the microbiota in the subject.

In certain embodiments, the one or more infectious diseases is selected from a viral, bacterial or fungal disease. In certain embodiments, the one or more allergic diseases is asthma. In certain embodiments, the one or more metabolic diseases/disorders is selected from diabetes, e.g. type 2 diabetes, and obesity. In certain embodiments, the one or more autoimmune diseases is selected from multiple sclerosis and rheumatoid arthritis.

In certain embodiments, the compositions of the invention are for use in treating or preventing IBS, IBD, obesity, type 2 diabetes, one of more infectious diseases, one or more allergic diseases, one or more autoimmune diseases or one or more metabolic diseases/disorders by increasing the microbiota diversity in the microbiota. In certain embodiments, the compositions of the invention are for use in treating or preventing IBS or IBD by inducing the stability of the microbiota. In certain embodiments, the compositions of the invention are for use in treating or preventing IBS by inducing the stability of the microbiota In preferred embodiments, the invention provides a composition comprising a bacterial strain of the genus *Blautia*, for use in the treatment or prevention of IBD, IBS, obesity, type 2 diabetes, one or more infectious diseases, one or more allergic diseases, one or more autoimmune diseases or one or more metabolic diseases/disorders, wherein the treatment or prevention comprises increasing the microbiota diversity and/or inducing the stability of the microbiota in the subject.

In some embodiments, the invention provides a composition comprising a bacterial strain of the genus *Blautia* for use in treating or preventing a disease or disorder selected from IBS, IBD, obesity, type 2 diabetes, one or more infectious diseases, one or more allergic diseases, one or more autoimmune diseases and one or more metabolic diseases/disorders. In some embodiments, the invention provides a method of treating or preventing a disease or disorder selected from IBS, IBD, obesity, type 2 diabetes, one or more infectious diseases, one or more allergic diseases, one or more autoimmune diseases and one or more metabolic diseases/disorders, comprising administering a composition comprising a bacterial strain of the genus *Blautia*.

In preferred embodiments, the compositions of the invention comprise the bacterium deposited under accession number DSM 10507/14294 and are for use in increasing the microbiota diversity and/or inducing the stability of the microbiota in the subject in the treatment of IBD, IBS, obesity, type 2 diabetes, one or more infectious diseases, one or more allergic diseases, one or more autoimmune diseases or one or more metabolic diseases/disorders. In further preferred embodiments, the compositions of the invention comprise the bacterium deposited under accession number DSM 10507/14294 and are for use in treating or preventing IBD, IBS, obesity, type 2 diabetes, one or more infectious diseases, one or more allergic diseases, one or more autoimmune diseases or one or more metabolic diseases/disorders by increasing the microbiota diversity and/or inducing the stability of the microbiota.

In some embodiments, the pathogenesis of the disease or disorder affects the intestine. In some embodiments, the pathogenesis of the disease or disorder does not affect the intestine. In some embodiments, the pathogenesis of the disease or disorder is not localised at the intestine. In some embodiments, the treating or preventing occurs at a site other than at the intestine. In some embodiments, the treating or preventing occurs at the intestine and also at a site other than at the intestine. In certain embodiments, the disease or disorder is systemic.

In certain embodiments, the compositions are for use in subjects that exhibit, or are expected to exhibit, reduced levels of microbiota diversity, for example, when compared to a healthy subject, or a population of healthy subjects. For example, in some embodiments, the composition is for use in treating a subject having less than 101 different bacterial species (e.g. less than 100, 99, 98, 97, 96, 95, 93, 90, 85, 80, 75 or 70 bacterial species) and/or less than 195 different strains (e.g. less than 193, 190, 187, 185, 183, 180, 175, 170, 165, 160, 150, 140 bacterial strains) in its microbiota. For example, in some embodiments, the composition is for use in treating a subject that has at least one bacterial genus (e.g. at least 2, 3, 4, 5, 6, 7, 8, 9 or 10 bacterial genera) fewer in its intestinal microbiota compared to a healthy subject or compared to a population of healthy subjects. In some embodiments, the treatment or prevention comprises a step of diagnosing a subject as having a reduced level of microbiota diversity and then if a reduced level of diversity is found to be present, the subject is then treated with a composition according to the invention.

In certain embodiments, the compositions are for use in subjects that exhibit, or are expected to exhibit, reduced stability of the microbiota. In some embodiments, the compositions are for use in subjects that exhibit, or are expected to exhibit, reduced stability in its microbiota, for example, when compared to a healthy subject, or a population of healthy subjects. In some embodiments, the treatment or prevention comprises a step of diagnosing a subject as having a reduced stability in its microbiota and then if reduced stability is found to be present, the subject is then treated with a composition according to the invention.

In certain embodiments, the subject is an infant. In certain embodiments, the subject is a child. In certain embodiments, the subject is an adult.

In certain embodiments, the subject is a healthy subject. For example, in some embodiments in which the composition is used for preventing a disease or disorder, the subject is a healthy subject, optionally one identified as being at risk of developing a disease or disorder characterised by a reduction in microbiota diversity.

In certain embodiments, the subject has previously received, is receiving, or will be receiving antibiotic treatment. Accordingly, in some embodiments, the treatment or prevention comprises administering the composition of the invention after, together with, or before antibiotic treatment. The composition of the invention and the one or more antibiotics may be for separate, simultaneous or sequential administration.

In some embodiments, the composition of the invention is for use in a method of increasing the microbiota diversity and/or inducing the stability of the microbiota in a subject having an increased level of hydrogen in their breath relative to a healthy subject. In some embodiments, the composition of the invention is for use in reducing the hydrogen level in the breath of a subject exhibiting or who is expected to exhibit a reduced level of diversity of its microbiota and/or reduced stability of the microbiota. The subject is preferably a subject diagnosed as having IBS, IBD, obesity, type 2 diabetes, one or more infectious diseases, one or more allergic diseases, one or more autoimmune diseases and/or one or more metabolic diseases/disorders. Treatment with a composition of the invention reduces the level of hydrogen detected in hydrogen breath tests. Accordingly, the hydrogen levels are preferably assessed using a hydrogen breath test. The hydrogen breath test is well known in the art and so the skilled person will know how to conduct such a test. In some embodiments, the subject is administered lactulose as the substrate for the test.

The hydrogen breath test is also a useful tool for monitoring the effectiveness or likely effectiveness of increasing the microbiota diversity and/or inducing the stability of the microbiota and of treatment or prevention using a composition of the invention. For example, a reduction in the level of hydrogen detected in a subject's breath following treatment with a composition of the invention may indicate that the treatment is having an increasing, stabilising, therapeutic or preventative effect. Accordingly, in some embodiments the methods and uses of the invention further comprise monitoring the hydrogen level in a subject's breath during and/or following treatment with a composition of the invention and thereby assessing the effectiveness or likely effectiveness of increasing, stabilising, treatment or prevention. For example, hydrogen levels may be monitored at one or more (e.g. 1, 2, 3, 4 or more than 4) times, for example, including before treatment, at the start of treatment, during treatment, at the end of treatment and/or following treatment, as desired. In some embodiments, the level of hydrogen in the subject's breath at the end and/or following the dosing period (during which the composition is administered to the subject) is compared to the level at the start and/or before the dosing period and a reduction in the level indicates the effectiveness or likely effectiveness of the increasing, stabilising, treatment or prevention. For example, in embodiments in which the dosing period is 16 days, it may be desirable to take measurements at day 1 and day 16, or for example at day 1, day 2, day 15 and day 16. In some embodiments, multiple measurements are taken and the mean of those measurements obtained (for example, the mean of day 1 and day 2 and the mean of day 15 and day 16). In some embodiments, a reduction in at least 40 ppm in the hydrogen level Cmax indicates that the increasing, stabilising, treatment or prevention is effective or likely to be effective. In some embodiments, the hydrogen level in the subject's breath is measured only once, for example, at the end of or following treatment, and the finding that the level is at or close to a predetermined level is indicative that the increasing stabilising, treatment or prevention is likely to have been effective. The hydrogen breath test is a standard assay and so predetermined levels are known in the art.

Treatment or prevention may refer to, for example, an alleviation of the severity of symptoms or a reduction in the frequency of exacerbations or the range of triggers that are a problem for the subject.

Bacteria in the microbiota may be detected in faeces from a subject, using standard techniques, such as the qPCR techniques used in the examples.

Modes of Administration

Preferably, the compositions of the invention are to be administered to the gastrointestinal tract in order to enable delivery to and/or partial or total colonisation of the intestine with the bacterial strain of the invention. Generally, the compositions of the invention are administered orally, but they may be administered rectally, intranasally, or via buccal or sublingual routes.

In certain embodiments, the compositions of the invention may be administered as a foam, as a spray or a gel.

In certain embodiments, the compositions of the invention may be administered as a suppository, such as a rectal suppository, for example in the form of a *theobroma* oil (cocoa butter), synthetic hard fat (e.g. suppocire, witepsol), glycero-gelatin, polyethylene glycol, or soap glycerin composition.

In certain embodiments, the composition of the invention is administered to the gastrointestinal tract via a tube, such as a nasogastric tube, orogastric tube, gastric tube, jejunostomy tube (J tube), percutaneous endoscopic gastrostomy (PEG), or a port, such as a chest wall port that provides access to the stomach, jejunum and other suitable access ports.

The compositions of the invention may be administered once, or they may be administered sequentially as part of a treatment regimen. In certain embodiments, the compositions of the invention are to be administered daily. The examples demonstrate that daily administration provides successful delivery and clinical benefits.

In certain embodiments, the compositions of the invention are administered regularly, such as daily, every two days, or weekly, for an extended period of time, such as for at least one week, two weeks, one month, two months, six months, or one year. The examples demonstrate that *B. hydrogenotrophica* administration may not result in permanent colonisation of the intestines, so regular administration for extended periods of time may provide greater therapeutic and/or prophylactic benefits.

In certain embodiments of the invention, treatment according to the invention is accompanied by assessment of the subject's gut microbiota. Treatment may be repeated if delivery of and/or partial or total colonisation with the strain of the invention is not achieved such that efficacy is not observed, or treatment may be ceased if delivery and/or partial or total colonisation is successful and efficacy is observed.

In certain embodiments, the composition of the invention may be administered to a pregnant animal, for example a mammal such as a human in order to prevent reduced levels of diversity in the microbiota and/or reduced stability of the microbiota developing in her child in utero and/or after it is born.

The compositions of the invention may be administered to a subject that has been diagnosed with reduced microbiota diversity relative to a healthy subject and/or reduced stability of the microbiota or a disease or disorder associated with reduced microbiota diversity relative to a healthy subject and/or reduced stability of the microbiota, or that has been identified as being at risk of reduced microbiota diversity relative to a healthy subject and/or reduced stability of the microbiota. The compositions may also be administered as a prophylactic measure to prevent the development of reduced microbiota diversity relative to a healthy subject and/or reduced stability of the microbiota in a healthy subject.

The compositions of the invention may be administered to a subject that has been identified as having an abnormal gut microbiota. For example, the subject may have reduced or absent colonisation by *Blautia*, and in particular *Blautia hydrogenotrophica*, *Blautia stercoris* or *Blautia wexlerae*.

The compositions of the invention may be administered as a food product, such as a nutritional supplement.

Generally, the compositions of the invention are for the treatment of humans, although they may be used to treat animals including monogastric mammals such as poultry, pigs, cats, dogs, horses or rabbits. The compositions of the invention may be useful for enhancing the growth and performance of animals. If administered to animals, oral gavage may be used.

Compositions

Generally, the composition of the invention comprises bacteria. In preferred embodiments of the invention, the composition is formulated in freeze-dried form. For example, the composition of the invention may comprise granules or gelatin capsules, for example hard gelatin capsules, comprising a bacterial strain of the invention.

Preferably, the composition of the invention comprises lyophilised bacteria. Lyophilisation of bacteria is a well-established procedure and relevant guidance is available in, for example, references [30-32]. The examples demonstrate that lyophilisate compositions are particularly effective.

Alternatively, the composition of the invention may comprise a live, active bacterial culture.

In some embodiments, the bacterial strain in the composition of the invention has not been inactivated, for example, has not been heat-inactivated. In some embodiments, the bacterial strain in the composition of the invention has not been killed, for example, has not been heat-killed. In some embodiments, the bacterial strain in the composition of the invention has not been attenuated, for example, has not been heat-attenuated. For example, in some embodiments, the bacterial strain in the composition of the invention has not been killed, inactivated and/or attenuated. For example, in some embodiments, the bacterial strain in the composition of the invention is live. For example, in some embodiments, the bacterial strain in the composition of the invention is viable. For example, in some embodiments, the bacterial strain in the composition of the invention is capable of partially or totally colonising the intestine. For example, in some embodiments, the bacterial strain in the composition of the invention is viable and capable of partially or totally colonising the intestine.

In some embodiments, the composition comprises a mixture of live bacterial strains and bacterial strains that have been killed.

In preferred embodiments, the composition of the invention is encapsulated to enable delivery of the bacterial strain to the intestine. Encapsulation protects the composition from degradation until delivery at the target location through, for example, rupturing with chemical or physical stimuli such as pressure, enzymatic activity, or physical disintegration, which may be triggered by changes in pH. Any appropriate encapsulation method may be used. Exemplary encapsulation techniques include entrapment within a porous matrix, attachment or adsorption on solid carrier surfaces, self-aggregation by flocculation or with cross-linking agents, and mechanical containment behind a microporous membrane or a microcapsule. Guidance on encapsulation that may be useful for preparing compositions of the invention is available in, for example, references [33] and [34].

The composition may be administered orally and may be in the form of a tablet, capsule or powder. Encapsulated products are preferred because *Blautia* are anaerobes. Other ingredients (such as vitamin C, for example), may be included as oxygen scavengers and prebiotic substrates to improve the delivery and/or partial or total colonisation and survival in vivo. Alternatively, the probiotic composition of the invention may be administered orally as a food or nutritional product, such as milk or whey based fermented dairy product, or as a pharmaceutical product.

The composition may be formulated as a probiotic.

A composition of the invention includes a therapeutically effective amount of a bacterial strain of the invention. A therapeutically effective amount of a bacterial strain is sufficient to exert a beneficial effect upon a subject. A therapeutically effective amount of a bacterial strain may be sufficient to result in delivery to and/or partial or total colonisation of the subject's intestine.

A suitable daily dose of the bacteria, for example for an adult human, may be from about $1\times10^3$ to about $1\times10^{11}$ colony forming units (CFU); for example, from about $1\times10^7$ to about $1\times10^{10}$ CFU; in another example from about $1\times10^7$ to about $1\times10^{11}$ CFU; in another example from about $1\times10^8$ to about $1\times10^{10}$ CFU; in another example from about $1\times10^8$ to about $1\times10^{11}$ CFU; in another example from about $1\times10^6$ to about $1\times10^{10}$ CFU.

In certain embodiments, the dose of the bacteria is at least $10^9$ cells per day, such as at least $10^{10}$, at least $10^{11}$, or at least $10^{12}$ cells per day.

In certain embodiments, the composition contains the bacterial strain in an amount of from about $1\times10^6$ to about $1\times10^{11}$ CFU/g, respect to the weight of the composition; for example, from about $1\times10^8$ to about $1\times10^{10}$ CFU/g. The dose may be, for example, 1 g, 3 g, 5 g, and 10 g.

Typically, a probiotic, such as the composition of the invention, is optionally combined with at least one suitable prebiotic compound. A prebiotic compound is usually a non-digestible carbohydrate such as an oligo- or polysaccharide, or a sugar alcohol, which is not degraded or absorbed in the upper digestive tract. Known prebiotics include commercial products such as inulin and transgalacto-oligosaccharides.

In certain embodiments, the probiotic composition of the present invention includes a prebiotic compound in an amount of from about 1 to about 30% by weight, respect to the total weight composition, (e.g. from 5 to 20% by weight). Carbohydrates may be selected from the group consisting of: fructo-oligosaccharides (or FOS), short-chain fructo-oligosaccharides, inulin, isomalt-oligosaccharides, pectins, xylo-oligosaccharides (or XOS), chitosan-oligosaccharides (or COS), beta-glucans, arable gum modified and resistant starches, polydextrose, D-tagatose, acacia fibers, carob, oats, and citrus fibers. In one aspect, the prebiotics are the short-chain fructo-oligosaccharides (for simplicity shown herein below as FOSs-c.c); said FOSs-c.c. are not digestible carbohydrates, generally obtained by the conversion of the beet sugar and including a saccharose molecule to which three glucose molecules are bonded.

The compositions of the invention may comprise pharmaceutically acceptable excipients or carriers. Examples of such suitable excipients may be found in the reference [35]. Acceptable carriers or diluents for therapeutic use are well known in the pharmaceutical art and are described, for example, in reference [36]. Examples of suitable carriers include lactose, starch, glucose, methyl cellulose, magnesium stearate, mannitol, sorbitol and the like. Examples of suitable diluents include ethanol, glycerol and water. The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s). Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like. Preservatives, stabilizers, dyes and even flavouring agents may be provided in the pharmaceutical composition. Examples of preservatives include sodium benzoate, sorbic acid, cysteine and esters of p-hydroxybenzoic acid. Antioxidants and suspending agents may be also used. A further example of a suitable carrier is saccharose. A further example of a preservative is cysteine.

The compositions of the invention may be formulated as a food product. For example, a food product may provide nutritional benefit in addition to the therapeutic effect of the invention, such as in a nutritional supplement. Similarly, a food product may be formulated to enhance the taste of the composition of the invention or to make the composition more attractive to consume by being more similar to a common food item, rather than to a pharmaceutical composition. In certain embodiments, the composition of the invention is formulated as a milk-based product. The term "milk-based product" means any liquid or semi-solid milk- or whey-based product having a varying fat content. The milk-based product can be, e.g., cow's milk, goat's milk, sheep's milk, skimmed milk, whole milk, milk recombined from powdered milk and whey without any processing, or a processed product, such as yoghurt, curdled milk, curd, sour milk, sour whole milk, butter milk and other sour milk products. Another important group includes milk beverages, such as whey beverages, fermented milks, condensed milks, infant or baby milks; flavoured milks, ice cream; milk-containing food such as sweets.

In certain embodiments, the compositions of the invention contain a single bacterial strain or species and do not contain any other bacterial strains or species. Such compositions may comprise only de minimis or biologically irrelevant amounts of other bacterial strains or species. Such compositions may be a culture or lyophilisate that is substantially free from other species of organism.

In certain embodiments, the compositions of the invention comprise one or more bacterial strains of the genus *Blautia*, for example, a *Blautia hydrogenotrophica*, and do not contain any other bacterial genus, or which comprise only de minimis or biologically irrelevant amounts of bacteria from another genus. In certain embodiments, the compositions of the invention comprise a single species of *Blautia*, for example, a *Blautia hydrogenotrophica*, and do not contain any other bacterial species, or which comprise only de minimis or biologically irrelevant amounts of bacteria from another species. In certain embodiments, the compositions of the invention comprise a single strain of *Blautia*, for example, of *Blautia hydrogenotrophica*, and do not contain any other bacterial strains or species, or which comprise only de minimis or biologically irrelevant amounts of bacteria from another strain or species.

In some embodiments, the compositions of the invention comprise more than one bacterial strain or species. For example, in some embodiments, the compositions of the invention comprise more than one strain from within the same species (e.g. more than 1, 2, 3, 4, 5, 6, 7, 8, 9, 10, 15, 20, 25, 30, 35, 40 or 45 strains), and, optionally, do not contain bacteria from any other species. In some embodiments, the compositions of the invention comprise less than 50 strains from within the same species (e.g. less than 45, 40, 35, 30, 25, 20, 15, 12, 10, 9, 8, 7, 6, 5, 4 or 3 strains), and, optionally, do not contain bacteria from any other species. In some embodiments, the compositions of the invention comprise 1-40, 1-30, 1-20, 1-19, 1-18, 1-15, 1-10, 1-9, 1-8, 1-7, 1-6, 1-5, 1-4, 1-3, 1-2, 2-50, 2-40, 2-30, 2-20, 2-15, 2-10, 2-5, 6-30, 6-15, 16-25, or 31-50 strains from within the same species and, optionally, do not contain bacteria from any other species. In some embodiments, the compositions of the invention comprise more than one species from within the same genus (e.g. more than 1, 2, 3, 4, 5, 6, 7, 8, 9, 10, 12, 15, 17, 20, 23, 25, 30, 35 or 40 species), and, optionally, do not contain bacteria from any other genus. In some embodiments, the compositions of the invention comprise less than 50 species from within the same genus (e.g. less than 50, 45, 40, 35, 30, 25, 20, 15, 12, 10, 8, 7, 6, 5, 4 or 3 species), and, optionally, do not contain bacteria from any other genus. In some embodiments, the compositions of the invention comprise 1-50, 1-40, 1-30, 1-20, 1-15, 1-10, 1-9, 1-8, 1-7, 1-6, 1-5, 1-4, 1-3, 1-2, 2-50, 2-40, 2-30, 2-20, 2-15, 2-10, 2-5, 6-30, 6-15, 16-25, or 31-50 species from within the same genus and, optionally, do not contain bacteria from any other genus. The invention comprises any combination of the foregoing.

In some embodiments, the composition comprises a microbial consortium. For example, in some embodiments, the composition comprises the *Blautia* bacterial strain, for example, a *Blautia hydrogenotrophica* bacterial strain as part of a microbial consortium. For example, in some embodiments, the *Blautia* bacterial strain is present in combination with one or more (e.g. at least 2, 3, 4, 5, 10, 15 or 20) other bacterial strains from other genera with which it can live symbiotically in vivo in the intestine. For example, in some embodiments, the composition comprises a bacterial strain of *Blautia hydrogenotrophica* in combination with a bacterial strain from a different genus. In some embodiments, the microbial consortium comprises two or more bacterial strains obtained from a faeces sample of a single organism, e.g. a human. In some embodiments, the microbial consortium is not found together in nature. For example, in some embodiments, the microbial consortium comprises bacterial strains obtained from faeces samples of at least two different organisms. In some embodiments, the two different organisms are from the same species, e.g. two different humans. In some embodiments, the two different organisms are an infant human and an adult human. In some embodiments, the two different organisms are a human and a non-human mammal.

In some embodiments, the composition of the invention additionally comprises a bacterial strain that has the same safety and therapeutic efficacy characteristics as the *Blautia hydrogenotrophica* strain deposited under accession number DSM 10507/14294, but which is not the *Blautia hydrogenotrophica* strain deposited under accession number DSM 10507/14294, or which is not a *Blautia hydrogenotrophica* or which is not a *Blautia*.

In some embodiments in which the composition of the invention comprises more than one bacterial strain, species or genus, the individual bacterial strains, species or genera may be for separate, simultaneous or sequential administration. For example, the composition may comprise all of the more than one bacterial strain, species or genera, or the bacterial strains, species or genera may be stored separately and be administered separately, simultaneously or sequentially. In some embodiments, the more than one bacterial strains, species or genera are stored separately but are mixed together prior to use.

In some embodiments, the bacterial strain for use in the invention is obtained from human adult faeces. In some embodiments in which the composition of the invention comprises more than one bacterial strain, all of the bacterial strains are obtained from human adult faeces or if other bacterial strains are present they are present only in de minimis amounts. In some embodiments, the bacteria may have been cultured subsequent to being obtained from the human adult faeces and being used in a composition of the invention.

In some embodiments, the one or more *Blautia* bacterial strains is/are the only therapeutically active agent(s) in a composition of the invention. In some embodiments, the bacterial strain(s) in the composition is/are the only therapeutically active agent(s) in a composition of the invention.

The compositions for use in accordance with the invention may or may not require marketing approval.

In certain embodiments, the invention provides the above pharmaceutical composition, wherein said bacterial strain is lyophilised. In certain embodiments, the invention provides the above pharmaceutical composition, wherein said bacterial strain is spray dried. In certain embodiments, the invention provides the above pharmaceutical composition, wherein the bacterial strain is lyophilised or spray dried and wherein it is live. In certain embodiments, the invention provides the above pharmaceutical composition, wherein the bacterial strain is lyophilised or spray dried and wherein it is viable. In certain embodiments, the invention provides the above pharmaceutical composition, wherein the bacterial strain is lyophilised or spray dried and wherein it is capable of partially or totally colonising the intestine. In certain embodiments, the invention provides the above pharmaceutical composition, wherein the bacterial strain is lyophilised or spray dried and wherein it is viable and capable of partially or totally colonising the intestine.

In some cases, the lyophilised or spray dried bacterial strain is reconstituted prior to administration. In some cases, the reconstitution is by use of a diluent described herein.

The compositions of the invention can comprise pharmaceutically acceptable excipients, diluents or carriers.

In certain embodiments, the invention provides a pharmaceutical composition comprising: a bacterial strain as used in the invention; and a pharmaceutically acceptable excipient, carrier or diluent; wherein the bacterial strain is in an amount sufficient to increase the microbiota diversity in a subject and/or induce stability of the microbiota and/or treat a disorder associated with reduced microbiota diversity and/or reduced stability of the microbiota when administered to a subject in need thereof, microbiota diversity, for example, a disease or disorder such as IBS, IBD, obesity, type 2 diabetes, one or more infectious diseases, one or more allergic diseases, one or more autoimmune diseases or one or more metabolic diseases/disorders.

In certain embodiments, the invention provides the above pharmaceutical composition, wherein the amount of the bacterial strain is from about $1\times10^3$ to about $1\times10^1$ colony forming units per gram with respect to a weight of the composition.

In certain embodiments, the invention provides the above pharmaceutical composition, wherein the composition is administered at a dose of 1 g, 3 g, 5 g or 10 g.

In certain embodiments, the invention provides the above pharmaceutical composition, wherein the composition is administered by a method selected from the group consisting of oral, rectal, subcutaneous, nasal, buccal, and sublingual.

In certain embodiments, the invention provides the above pharmaceutical composition, comprising a carrier selected from the group consisting of lactose, starch, glucose, methyl cellulose, magnesium stearate, mannitol and sorbitol.

In certain embodiments, the invention provides the above pharmaceutical composition, comprising a diluent selected from the group consisting of ethanol, glycerol and water.

In certain embodiments, the invention provides the above pharmaceutical composition, comprising an excipient selected from the group consisting of starch, gelatin, glucose, anhydrous lactose, free-flow lactose, beta-lactose, corn sweetener, acacia, tragacanth, sodium alginate, carboxymethyl cellulose, polyethylene glycol, sodium oleate, sodium stearate, magnesium stearate, sodium benzoate, sodium acetate and sodium chloride.

In certain embodiments, the invention provides the above pharmaceutical composition, further comprising at least one of a preservative, an antioxidant and a stabilizer.

In certain embodiments, the invention provides the above pharmaceutical composition, comprising a preservative selected from the group consisting of sodium benzoate, sorbic acid and esters of p-hydroxybenzoic acid.

In certain embodiments, the invention provides the above pharmaceutical composition, wherein said bacterial strain is lyophilised.

In certain embodiments, the invention provides the above pharmaceutical composition, wherein when the composition is stored in a sealed container at about 4° C. or about 25° C. and the container is placed in an atmosphere having 50% relative humidity, at least 80% of the bacterial strain as measured in colony forming units, remains after a period of at least about: 1 month, 3 months, 6 months, 1 year, 1.5 years, 2 years, 2.5 years or 3 years.

In some embodiments, the composition of the invention is provided in a sealed container comprising a composition as described herein. In some embodiments, the sealed container is a sachet or bottle. In some embodiments, the composition of the invention is provided in a syringe comprising a composition as described herein.

The composition of the present invention may, in some embodiments, be provided as a pharmaceutical formulation. For example, the composition may be provided as a tablet or capsule. In some embodiments, the capsule is a gelatine capsule ("gel-cap").

In some embodiments, the compositions of the invention are administered orally. Oral administration may involve swallowing, so that the compound enters the gastrointestinal tract, and/or buccal, lingual, or sublingual administration by which the compound enters the blood stream directly from the mouth.

Pharmaceutical formulations suitable for oral administration include solid plugs, solid microparticulates, semi-solid and liquid (including multiple phases or dispersed systems) such as tablets; soft or hard capsules containing multi- or nano-particulates, liquids (e.g. aqueous solutions), emulsions or powders; lozenges (including liquid-filled); chews; gels; fast dispersing dosage forms; films; ovules; sprays; and buccal/mucoadhesive patches.

In some embodiments the pharmaceutical formulation is an enteric formulation, i.e. a gastro-resistant formulation (for example, resistant to gastric pH) that is suitable for delivery of the composition of the invention to the intestine by oral administration. Enteric formulations may be particularly useful when the bacteria or another component of the composition is acid-sensitive, e.g. prone to degradation under gastric conditions.

In some embodiments, the enteric formulation comprises an enteric coating. In some embodiments, the formulation is an enteric-coated dosage form. For example, the formulation may be an enteric-coated tablet or an enteric-coated capsule, or the like. The enteric coating may be a conventional enteric coating, for example, a conventional coating for a tablet, capsule, or the like for oral delivery. The formulation may comprise a film coating, for example, a thin film layer of an enteric polymer, e.g. an acid-insoluble polymer.

In some embodiments, the enteric formulation is intrinsically enteric, for example, gastro-resistant without the need for an enteric coating. Thus, in some embodiments, the formulation is an enteric formulation that does not comprise an enteric coating. In some embodiments, the formulation is a capsule made from a thermogelling material. In some embodiments, the thermogelling material is a cellulosic material, such as methylcellulose, hydroxymethylcellulose or hydroxypropylmethylcellulose (HPMC). In some embodiments, the capsule comprises a shell that does not contain any film forming polymer. In some embodiments, the capsule comprises a shell and the shell comprises hydroxypropylmethylcellulose and does not comprise any film forming polymer (e.g. see [37]). In some embodiments, the formulation is an intrinsically enteric capsule (for example, Vcaps® from Capsugel).

In some embodiments, the formulation is a soft capsule. Soft capsules are capsules which may, owing to additions of softeners, such as, for example, glycerol, sorbitol, maltitol and polyethylene glycols, present in the capsule shell, have a certain elasticity and softness. Soft capsules can be produced, for example, on the basis of gelatine or starch. Gelatine-based soft capsules are commercially available from various suppliers. Depending on the method of administration, such as, for example, orally or rectally, soft capsules can have various shapes, they can be, for example, round, oval, oblong or torpedo-shaped. Soft capsules can be produced by conventional processes, such as, for example, by the Scherer process, the Accogel process or the droplet or blowing process.

Culturing Methods

The bacterial strains for use in the present invention can be cultured using standard microbiology techniques as detailed in, for example, references [38-40].

The solid or liquid medium used for culture may be YCFA agar or YCFA medium. YCFA medium may include (per 100 ml, approximate values): Casitone (1.0 g), yeast extract (0.25 g), $NaHCO_3$ (0.4 g), cysteine (0.1 g), $K_2HPO_4$ (0.045 g), $KH_2PO_4$ (0.045 g), NaCl (0.09 g), $(NH_4)_2SO_4$ (0.09 g), $MgSO_4 \cdot 7H_2O$ (0.009 g), $CaCl_2$ (0.009 g), resazurin (0.1 mg), hemin (1 mg), biotin (1 µg), cobalamin (1 µg), p-aminobenzoic acid (3 µg), folic acid (5 µg), and pyridoxamine (15 µg).

Bacterial Strains for Use in Vaccine Compositions

The inventors have identified that the bacterial strains of the invention are useful for treating or preventing diseases or disorders associated with a level of microbiota diversity that is reduced relative to the microbiota diversity of a healthy subject (or relative to the microbiota diversity of a population of healthy subjects) and/or diseases or disorders that are associated with reduced stability of the microbiota compared to a healthy subject (or compared to a population of healthy subjects). This is likely to be a result of the effect that the bacterial strains of the invention have on the host immune system. Therefore, the compositions of the invention may also be useful for preventing such diseases or disorders when administered as vaccine compositions. In certain such embodiments, the bacterial strains of the invention are viable. In certain such embodiments, the bacterial strains of the invention are capable of partially or totally colonising the intestine. In certain such embodiments, the bacterial strains of the invention are viable and capable of partially or totally colonising the intestine. In other certain such embodiments, the bacterial strains of the invention may be killed, inactivated or attenuated. In certain such embodiments, the compositions may comprise a vaccine adjuvant. In certain embodiments, the compositions are for administration via injection, such as via subcutaneous injection.

General

The practice of the present invention will employ, unless otherwise indicated, conventional methods of chemistry, biochemistry, molecular biology, immunology and pharmacology, within the skill of the art. Such techniques are explained fully in the literature. See, e.g., references [41] and [42-48], etc.

The term "comprising" encompasses "including" as well as "consisting" e.g. a composition "comprising" X may consist exclusively of X or may include something additional e.g. X+Y.

The term "about" in relation to a numerical value x is optional and means, for example, x+10%.

The word "substantially" does not exclude "completely" e.g. a composition which is "substantially free" from Y may be completely free from Y. Where necessary, the word "substantially" may be omitted from the definition of the invention.

References to a percentage sequence identity between two nucleotide sequences means that, when aligned, that percentage of nucleotides are the same in comparing the two sequences. This alignment and the percent homology or sequence identity can be determined using software programs known in the art, for example those described in section 7.7.18 of ref. [49]. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref. [50].

Unless specifically stated, a process or method comprising numerous steps may comprise additional steps at the beginning or end of the method, or may comprise additional intervening steps. Also, steps may be combined, omitted or performed in an alternative order, if appropriate.

Various embodiments of the invention are described herein. It will be appreciated that the features specified in each embodiment may be combined with other specified features, to provide further embodiments. In particular, embodiments highlighted herein as being suitable, typical or preferred may be combined with each other (except when they are mutually exclusive).

MODES FOR CARRYING OUT THE INVENTION

EXAMPLE 1—Changes in Patient Microbiota after *Blautia hydrogenotrophica* Treatment Summary The effect of *Blautia hydrogenotrophica* on the diversity and stability of patient microbiota was tested in healthy and IBS patients.

Methodology

Study Design

A Phase I clinical trial was conducted in which *Blautia hydrogenotrophica* ("Blautix", strain deposited under accession number DSM 10507 and also under accession number DSM 14294) was administered to human patients having IBS or healthy human patients. Patients were administered Blautix during a dosing period (days 1-16) with the washout period being day 19-23. Faecal samples were collected from IBS & healthy subjects, placebo or Blautix treated, at: baseline, day 1 (D1) prior to treatment; end of treatment day 16 (D-16); and at end of study (EOS), which was 2-4 weeks (wash-out) post-treatment.

16S Amplicon Sequencing

A Qiagen DNeasy Blood & Tissue Kit was used following the manufacturer's instructions, to extract microbial DNA from 0.2 g of frozen faecal samples from IBS & Healthy subjects, placebo or Blautix treated, at: baseline, day 1 (D1) prior to treatment; end of treatment day 16 (D-16); and at end of study (EOS), which was 2-4 weeks (wash-out) post-treatment.

Preparation and sequencing of the 16S rRNA gene amplicons was carried out using the 16S Sequencing Library Preparation Nextera protocol developed by Illumina (San Diego, Calif., USA). 50 ng of each of the DNA faecal extracts was amplified using PCR and primers targeting the V3/V4 variable region of the 16S rRNA gene. The products were purified and forward and reverse barcodes were attached by a second round of adapter PCR. The resulting PCR products were purified, quantified and equimolar amounts of each amplicon were then pooled before being sent for sequencing to the commercial Supplier GATC Gmbh., on either the MiSeq (2×250 bp chemistry) or HiSeq (2×300 bp chemistry) platforms.

Data Analysis (Post-Sequencing)

The raw sequence data was merge trimmed using flash methodology. This filters out low quality reads. The USEARCH pipeline methodology (version 8.1.1861_i86_linux64) was used to identify singletons and hide them from the OTU (Operational Taxonomic Unit) generating step. The UPARSE algorithm was used to cluster the sequences into OTUs. Chimeric sequences generated in the amplification step were removed using the UCHIME chimera removal algorithm with the Chimeraslayer reference database (downloaded: 9 Sep. 2016). The USEARCH global alignment algorithm was then used to map all reads, including singletons onto the remaining OTU sequences. In-house scripts were used to then group the sequences into OTUs as classified by the USEARCH global alignment algorithm. Individual sequences were grouped into OTUs to give microbiome compositional information (abundance and diversity).

High-Level Data Analysis

The Bray-Curtis dissimilarity matrix was generated for each sample pairing using the Vegan library in R 3.3.1. Dataset was visualised using Principal Coordinate analysis with the Bray-Curtis dissimilarity matrix.

An in-house heatplot R function was used to generate a heatmap visualisation with hierarchical clustering based on the Bray-Curtis dissimilarity and ward linkage.

Shannon and Simpson diversity indexes were generated using the phyloseq library in R.

DESeq2 methodology was used to identify taxonomic variables that were significant for chosen comparisons.

Permutational MANOVA was performed on the dissimilarity matrix using the *Adonis* function in R.

Results

Samples from all time points were pooled for both groups (71 IBS patients and 67 healthy controls including both the Blautix treated and placebo groups). Analysis was performed using a distance measure generated on the full microbiome dataset. FIG. 1 reports that the microbiota of IBS subjects is significantly different from that of healthy subjects.

Diversity analysis was carried out using Observed number of predicted Taxa (OTUs), Shannon diversity index and Simpson Diversity index. Both treatment groups showed an increase in diversity at Day 16 timepoint which was significant for the observed OTUs and showed a trend for the Simpson (Raw P-value: <0.1) (FIG. 2). This increase in diversity was not observed with patients treated with the placebo. A significant decrease in microbiota diversity was observed in the untreated IBS placebo group between End of study and Day 1.

FIGS. 3A-3B report that Blautix treatment increased the microbiota network connectivity of certain health-associated taxa. In healthy patients a substantial increase in inter-microbe connections was observed from Day 1 to Day 16 (after Blautix treatment), which suggests an increase in cooperation and microbiota structure (FIG. 3A). Connectivity is correlated with diversity and stability. After the wash period the network structure reverted to a network similar to that observed on Day 1. Blautix treatment was, therefore, able to increase interconnectivity in healthy patients but the effect was lost post wash out. In IBS patients the network remained similar in terms of connectivity between Day 1 and Day 16, but an increase in connectivity was observed by the end of the study suggesting an increased microbiota structure post washout period in Blautix-treated IBS patients (FIG. 3B). The effect of Blautix on microbiome connectivity was, therefore, delayed in IBS patients compared to healthy patients.

Instability/change in the microbiota profiles were represented by Bray Curtis distances between timepoints of the same subject. Bray-Curtis shows dissimilarity between species abundance profiles limited between 0-1 (0=same; 1=do not share any species). Treatment of IBS patients with Blautix reduced the magnitude of microbiota changes during the treatment (FIG. 4A) and after the treatment (FIGS. 4B-4C). This shows that Blautix increased the stability of the microbiota in IBS patients and that the change continues after the intervention. This increased stability was not observed when IBS patients were administered the placebo (FIGS. 4 A-C).

Figure 5:
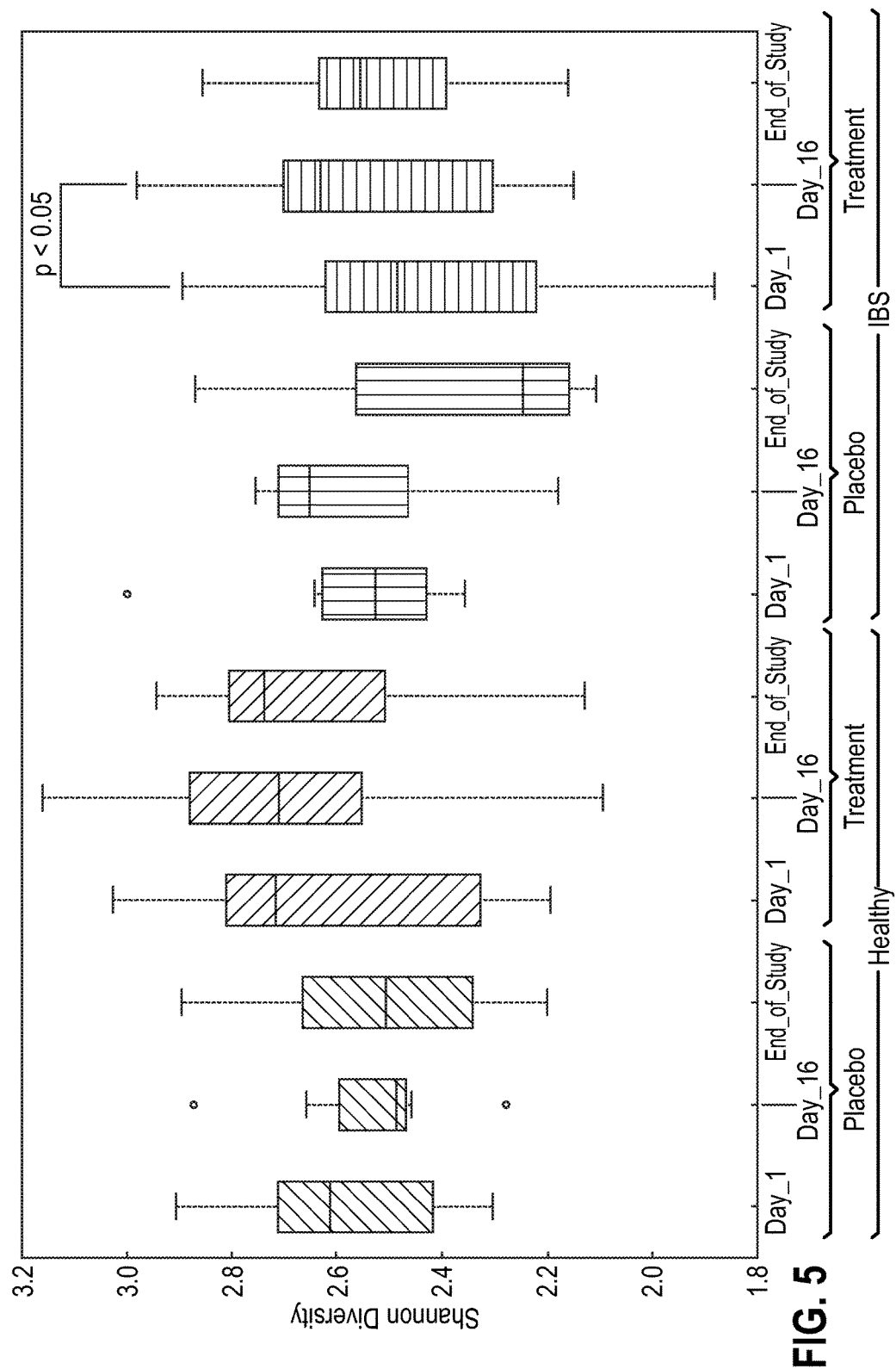
FIG. 5: Comparison of microbiota diversity at different time points for healthy and IBS patients after BlautiX treatment.

FIG. 5 reports that there was a significant increase in microbiota diversity at the genus level for IBS patients treated with Blautix at Day 16 compared to Day 1. The diversity analysis was carried out using the Shannon diversity index applied to the Genus level (Raw p-value:0.04, Day 1 versus Day 16).

Figure 6B:
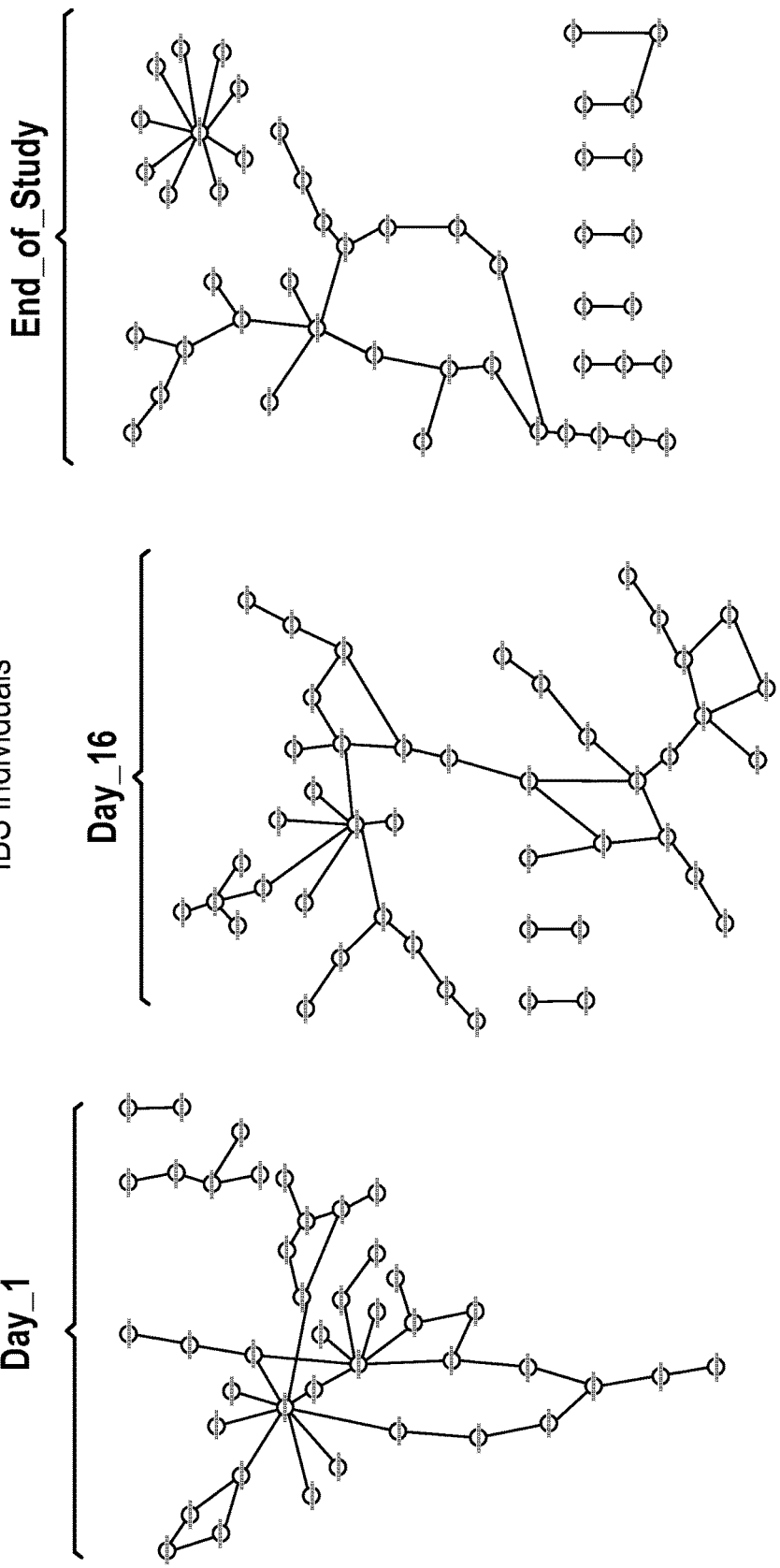

FIG. 6A and FIG. 6B show the changes in the mutual exclusion networks in healthy and IBS patients after Blautix treatment. In healthy individuals the mutual exclusion network becomes more dense and interconnected at Day 16, which is suggestive of increased competition and inhibition. This effect was lost, however, by the end of the study as the network structure reverted back to the initial time point during the washout period (FIG. 6A). In IBS patients the effect of Blautix on mutual exclusion connectivity was to increase the network diameter over the treatment period and the washout period. This was opposite to the effect seen in the healthy individuals where the network become denser. During the washout phase for the IBS patients, multiple independent interactions were observed that were not seen previously. Multiple independent interactions represent pairs of taxa that are interacting in a manner that is independent of the rest of the network, i.e. they do not have any interactions to the rest of the network.

Figure 7:
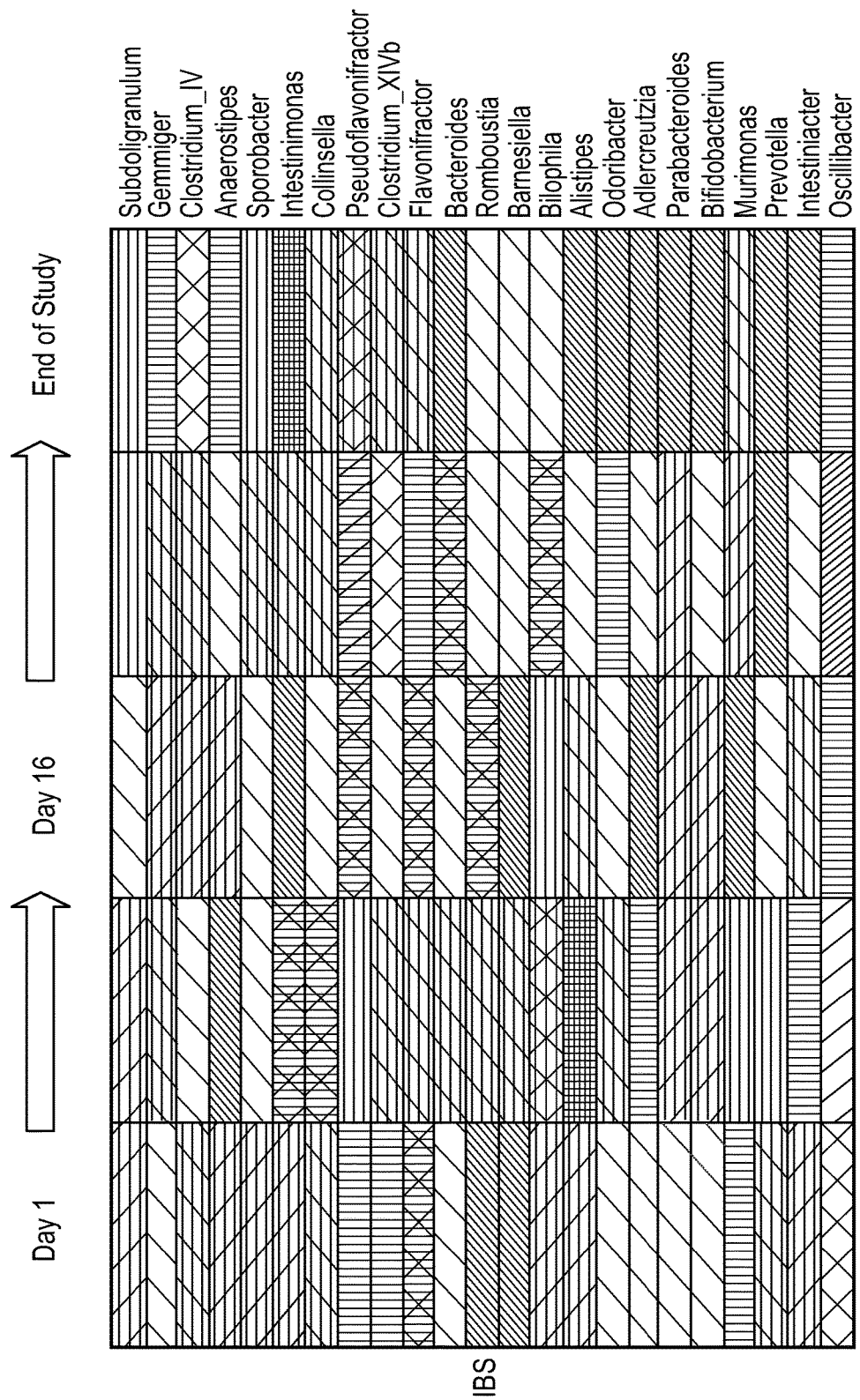
FIG. 7: Hierarchical clustering of microbiota.

Visualisation of microbiota shows that after Blautix treatment there was an increased network connectivity for certain health-associated taxa (FIG. 7). The health associated taxa include *Clostridium* cluster IV, *Bifidobacterium* and *Prevotella*. Oscillibacter is also potentially a health associated genera. These health-associated taxa are implicated in the response to treatment.

EXAMPLE 2—Protective Effect in Models of Neurodevelopmental Disorders

The BTBR Mouse Model

The BTBR mouse model uses inbred, genetically modified mice that display a robust autistic-like phenotype. Deficits in social behaviours, increased repetitive behaviours and increased anxiety-related behaviours have been reported in this strain [51]. Due to this robust behavioural phenotype, the BTBR mouse is an ideal animal model to assess the efficacy of novel therapeutic agents for the treatment of autistic-related behaviours. Alleviation of such symptoms by a live biotherapeutic can also be indicative of efficacy of the biotherapeutic in the treatment of other psychiatric or neurological diseases.

Mice

Male BTBR mice were bred in house. The animals were housed in a temperature- and humidity-controlled room on a 12 hr dark cycle (lights on from 7:00-19:00 hr). All experiments were conducted in accordance with the European Directive 2010/63/EEC, the requirements of S.I. No 543 of 2012, and approved by the Animal Experimentation Ethics Committee of University College Cork.

Strain

*Blautia hydrogenotrophica* bacterium deposited under accession number DSM 10507 and also under accession number DSM 14294.

Biotherapeutic was provided in glycerol stock. Live biotherapeutics were grown in the facility in anaerobic conditions.

Live Biotherapeutic Administration

Dosing with *Blautia hydrogenotrophica* commenced when the mice were 8 weeks old. These mice were treated once daily for 3 weeks via oral gavage.

Administration Schedule

The vehicle for oral administration is PBS. Daily oral administration occurs via oral gavage.

Fecal Collection

Fresh fecal samples were collected from individual mice before and after administration of *Blautia hydrogenotrophica*. At least 20 mg of fresh faeces were placed in a microcentrifuge tube, placed immediately on ice and then stored at −80□.

Results

Figure 8:
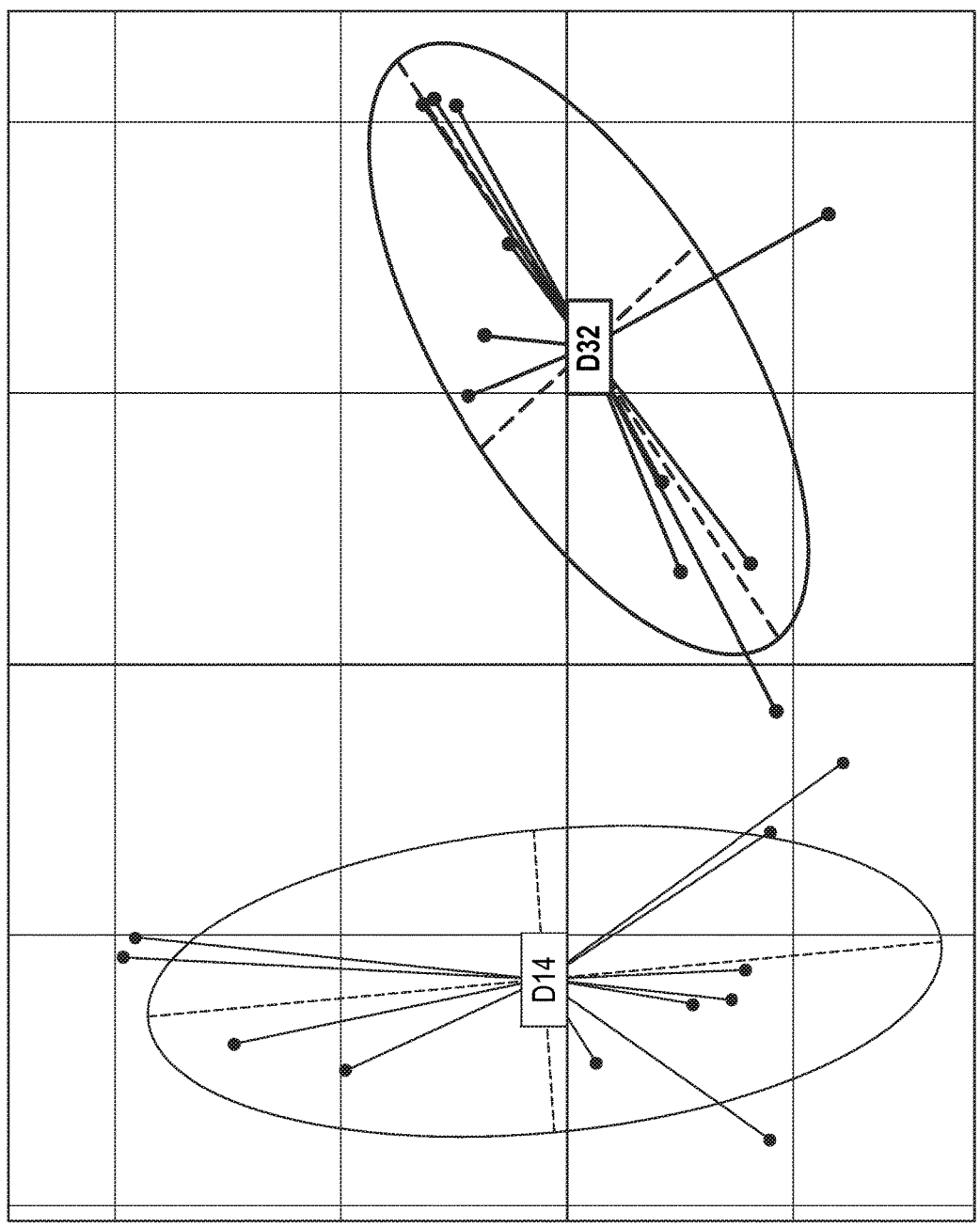
FIG. 8: Comparison of microbiota profiles before (D14) and after (D32) Blautix treatment based on Bray-Curtis dissimilarities.

The effect of Blautix treatment on microbiota between timepoints (D14, D32) is shown in FIG. 8. Significant temporal variation in the microbiota profiles was observed (p-value=0.001) between the before treatment (D14) and after treatment (D32) study timepoints.

Differential analysis using DESeq2 yielded 25 significant (adjusted p-value<0.05) differentially abundant taxa for the Blautix treatment between the D14 and D32 Autism study timepoints. The taxa are listed in Table 1 below.

TABLE 1

Significant differentially abundant taxa between D14 and D32 time points in the autism study. A positive fold change is interpreted as increased at D32 when compared to D14.

| OTU_ID | Lowest Level | Classification | log2 fold change | st error | adjusted p-value |
|---|---|---|---|---|---|
| 2440650 | Genus | *Clostridium* XIVa | 19.706 | 3.008 | 6.9E−10 |
| 307526 | Species | *Bacteroides acidifaciens* | 11.275 | 0.912 | 5.0E−33 |
| 39008 | Species | *Bacteroides acidifaciens* | 10.501 | 1.345 | 1.0E−13 |
| 277773 | Species | *Alistipes finegoldii* | 9.954 | 0.906 | 2.8E−26 |
| 1105465 | Genus | *Barnesiella* | 9.255 | 0.923 | 2.8E−22 |
| 943687 | Family | Porphyromonadaceae | 9.200 | 0.850 | 1.1E−25 |
| 47662 | Species | *Barnesiella intestinihominis* | 8.844 | 0.988 | 7.0E−18 |
| 181003 | Genus | *Alistipes* | 8.370 | 2.069 | 4.2E−04 |
| 1282905 | Species | *Barnesiella intestinihominis* | 7.373 | 1.004 | 2.8E−12 |
| 1370810 | Species | *Barnesiella intestinihominis* | 6.633 | 1.986 | 0.006 |
| 1203483 | Species | *Bacteroides acidifaciens* | 6.599 | 1.584 | 2.7E−04 |
| 74179 | Species | *Alistipes massiliensis* | 6.318 | 1.899 | 0.006 |
| 1640334 | Species | *Barnesiella intestinihominis* | 6.258 | 2.066 | 0.013 |
| 76239 | Family | Lachnospiraceae | 6.202 | 1.229 | 4.6E−06 |
| 308030 | Species | *Barnesiella intestinihominis* | 6.196 | 1.451 | 1.8E−04 |
| 1156020 | Family | Erysipelotrichaceae | 5.827 | 1.607 | 0.002 |
| 712755 | Species | *Barnesiella intestinihominis* | 5.614 | 1.749 | 0.008 |
| 11297 | Family | Porphyromonadaceae | 5.450 | 1.021 | 1.0E−06 |
| 2218722 | Genus | *Clostridium* IV | 3.983 | 1.017 | 0.001 |
| 594012 | Species | *Clostridium lactatifermentans* | 2.900 | 0.952 | 0.013 |

TABLE 1-continued

Significant differentially abundant taxa between D14 and D32 time points in the autism study. A positive fold change is interpreted as increased at D32 when compared to D14.

| OTU_ID | Lowest Level | Classification | log2 fold change | st error | adjusted p-value |
|---|---|---|---|---|---|
| 453043 | Species | Eubacterium ventriosum | −3.675 | 1.260 | 0.018 |
| 451019 | Species | Barnesiella intestinihominis | −4.055 | 1.540 | 0.041 |
| 466087 | Species | Akkermansia muciniphila | −6.727 | 0.876 | 2.5E−13 |
| 2153421 | Genus | Blautia XIVa | −8.051 | 2.577 | 0.010 |
| 866478 | Species | Barnesiella intestinihominis | −8.961 | 0.846 | 9.3E−25 |

Summary

In a mouse model of autism in which animals were administered Blautix, a significant variation on their microbiome was observed, including a substantial net increase in bacterial diversity.

EXAMPLE 3—Effect in Models of Cerebral Ischemia

Summary

The protective effect of *Blautia hydrogenotrophica* was tested in mouse models of cerebral ischemia. To this end three groups of 5-17 mice were tested. Only normally behaving animals were included in the study. The first dosing day was Day −14. One group received freeze dried bacteria daily from the first dosing day until termination. The control groups received either vehicle or lyobuffer.

On Day 1, all mice were anesthetized. A midline incision was created in the ventral side of the neck to expose the right and left common carotid-arteries. A cerebral ischemia-reperfusion I/R model was then induced by bilateral common carotid artery occlusion (BCCAO) using vascular clips for 15 minutes. At the end of each occlusion, the clips were removed.

Strain

*Blautia hydrogenotrophica* bacterium deposited under accession number DSM 10507 and also under accession number DSM 14294.

Administration Schedule

| No. of Animals | Treatment | Dose Level (mg/kg) | Dose Volumes (ml/kg or ml/animal) |
|---|---|---|---|
| 12 | PBS (negative control) | n/a | 10 |
| 17 | Freeze-dried Powder | 7.8 mg in 100 μl | 100 μl per animal |
| 13 | Freeze-dried Bacteria | 15.6 mg in 100 μl (bacteria dose = 2 × 10$^8$) | 100 μl per animal |

Study Design

Days −14 to 14: Daily dose of PBS control (lyobuffer), freeze dried powder control (vehicle) or freeze dried bacteria (Blautix).

Day 1: Cerebral ischemia-reperfusion I/R model induced by surgery.

Day 14: Half of the mice in each group were terminated.

Day 14 to 28: Daily dose of PBS control (lyobuffer), freeze dried powder control (vehicle) or freeze dried bacteria (Blautix) for the remaining mice in each group.

Day 28: Termination of remaining mice.

Faecal pellets were collected at three time points: Day −14, Day 14 and Day 28. Each take was carried out in a sterile environment (fully aseptic=cleaned between animals), with every mouse being taken out of the cage and placed separately into a new sterile box for individual pellet harvesting. As many pellets as possible were collected in order to reach a minimum of 80 mg and preferably 100 mg of material per mouse.

Results

Figure 9A:
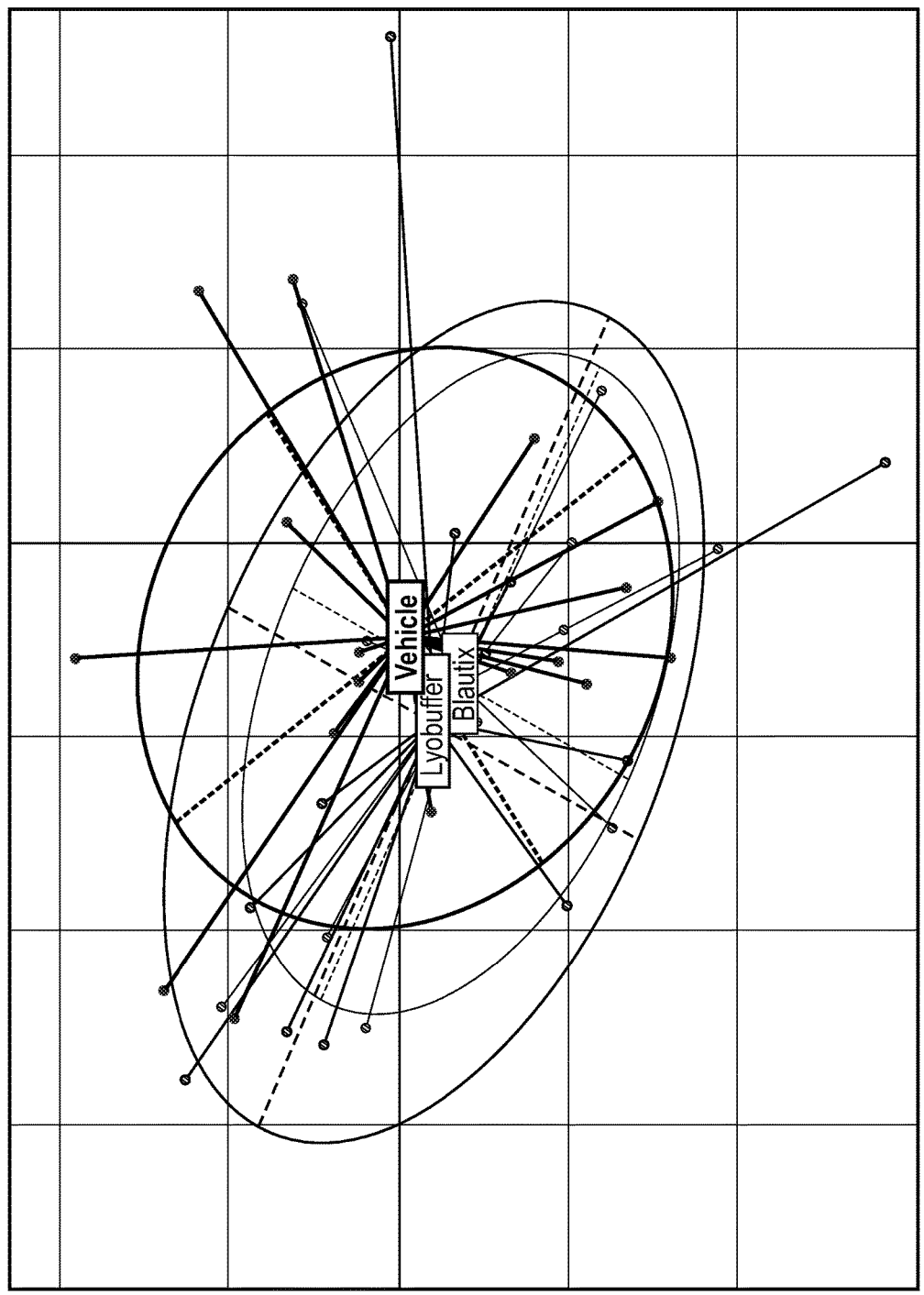
FIGS. 9A-9C.
Figure 9B:
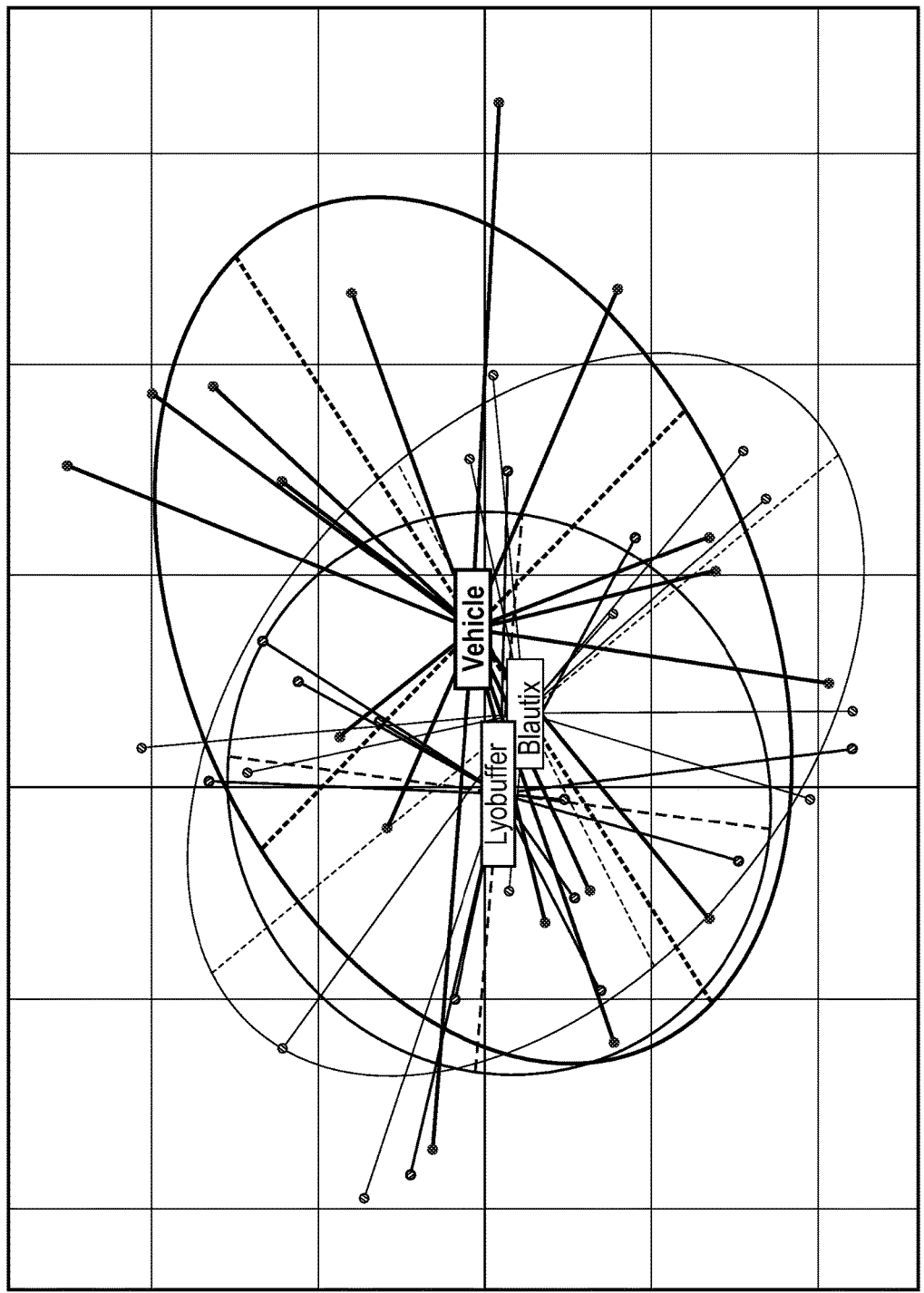
Figure 9C:
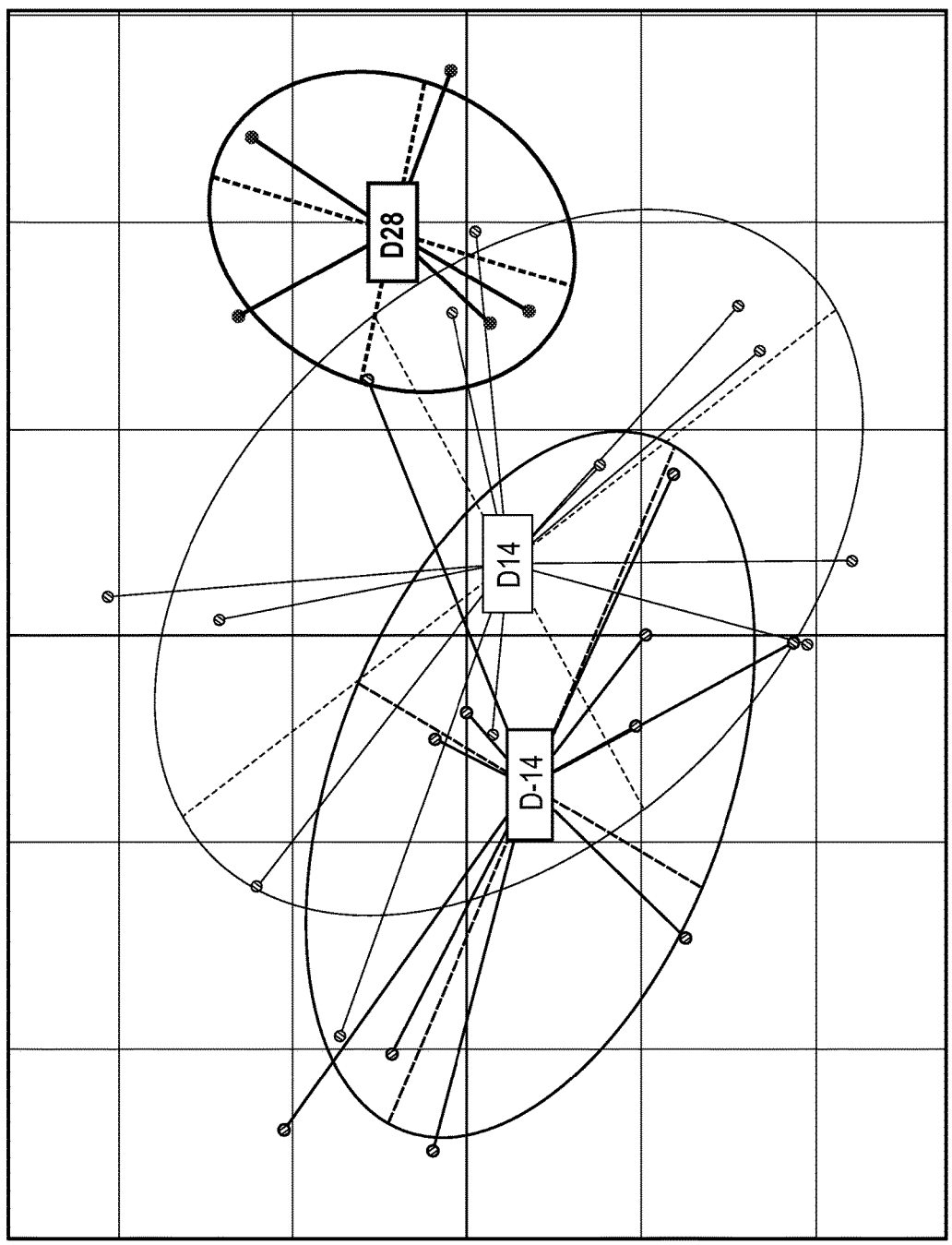

No significant differences in microbiota profiles between the Blautix treatment, Vehicle and Lyobuffer groups were detected at D-14 (p-value=0.177) before administration of Blautix (see FIG. 9A). However, significant differences were observed in microbiota profiles between the different treatment groups at Day 14 (see FIG. 9B) with a p-value of 0.011 observed. The inventors further assessed the temporal variation in the microbiota of the Blautix treated group and found a significant difference (see FIG. 9C) with a p-value of 0.002 observed.

Differential analysis using DESeq2 yielded significant (adjusted p-value <0.05) differentially abundant taxa for the Vehicle, Lyobuffer and Blautix treatment between timepoints in the Stroke study, as shown in Table 2, demonstrating a longer term impact on bacterial diversity imparted by Blautix. The taxa for the Blautix treatment are listed in Table 3, Table 4 and Table 5.

TABLE 2

Significant differentially abundant taxa between time points in the Stroke study.

| — | D-14 −> D14 | D14 −> D28 | D-14 −> D28 |
|---|---|---|---|
| Vehicle | 4 | 0 | 2 |
| Lyobuffer | 17 | 2 | 0 |
| Blautix | 7 | 14 | 12 |

TABLE 3

Significant differentially abundant taxa between D-14 and D14 timepoints for the Blautix treatment in the Stroke study. A positive fold change is interpreted as increased at D14 when compared to D-14.

| OTU_ID | Lowest Level | Classification | log2 fold change | st error | adjusted p-value |
|---|---|---|---|---|---|
| 321825 | Family | Ruminococcaceae | 1.647 | 0.470 | 0.027 |
| 74771 | Species | Alistipes massiliensis | 1.530 | 0.442 | 0.027 |
| 567799 | Genus | Alistipes | −1.215 | 0.308 | 0.008 |
| 77091 | Genus | Clostridium | −1.634 | 0.489 | 0.036 |
| 472737 | Family | Lachnospiraceae | −2.585 | 0.667 | 0.008 |
| 615246 | Family | Lachnospiraceae | −3.003 | 0.711 | 0.007 |
| 166882 | Family | Lachnospiraceae | −5.547 | 1.406 | 0.008 |

TABLE 4

Significant differentially abundant taxa between D14 and D28 timepoints for the Blautix treatment in the Stroke study. A positive fold change is interpreted as increased at D28 when compared to D14.

| OTU_ID | Lowest Level | Classification | log2 fold change | st error | adjusted p-value |
|---|---|---|---|---|---|
| 1101936 | Order | Clostridiales | 3.275 | 0.709 | 0.001 |
| 218505 | Species | Roseburia faecis | 2.568 | 0.630 | 0.002 |
| 948888 | Genus | Barnesiella | 2.499 | 0.575 | 0.001 |
| 612631 | Genus | Clostridium XIVa | 2.473 | 0.723 | 0.011 |
| 201398 | Phylum | Bacteroidetes | 2.045 | 0.605 | 0.011 |
| 1370810 | Species | Barnesiella intestinihominis | 1.878 | 0.579 | 0.016 |
| 770554 | Species | Alistipes putredinis | 1.868 | 0.626 | 0.033 |
| 558330 | Genus | Prevotella | 1.795 | 0.453 | 0.002 |
| 943687 | Family | Porphyromonadaceae | 1.586 | 0.546 | 0.039 |
| 308030 | Species | Barnesiella intestinihominis | 1.324 | 0.361 | 0.005 |
| 176124 | Phylum | Bacteroidetes | 1.163 | 0.294 | 0.002 |
| 565518 | Species | Oscillospira guilliermondii | -1.571 | 0.488 | 0.016 |
| 544582 | Species | Flavonifractor plautii | -1.599 | 0.569 | 0.050 |
| 25678 | Species | Mucispirillum schaedleri | -2.751 | 0.640 | 0.001 |

TABLE 5

Significant differentially abundant taxa between D-14 and D28 timepoints for the Blautix treatment in the Stroke study. A positive fold change is interpreted as increased at D28 when compared to D-14.

| OTU_ID | Lowest Level | Classification | log2 fold change | st error | adjusted p-value |
|---|---|---|---|---|---|
| 688867 | Genus | Clostridium XIVa | 8.296 | 1.136 | 3.8E-11 |
| 612631 | Genus | Clostridium XIVa | 7.814 | 1.348 | 3.1E-07 |
| 560658 | Family | Lachnospiraceae | 5.241 | 1.243 | 0.001 |
| 929749 | Species | Eubacterium ruminantium | 3.190 | 0.829 | 0.003 |
| 518034 | Species | Desulfovibrio fairfieldensis | 3.098 | 0.982 | 0.024 |
| 74771 | Species | Alistipes massiliensis | 2.548 | 0.714 | 0.007 |
| 23310 | Species | Odoribacter laneus | 1.621 | 0.475 | 0.011 |
| 117624 | Order | Clostridiales | -1.748 | 0.612 | 0.049 |
| 411272 | Genus | Clostridium XIVa | -2.923 | 1.019 | 0.049 |
| 39008 | Species | Bacteroides acidifaciens | -2.953 | 0.816 | 0.007 |
| 331352 | Genus | Clostridium XIVa | -3.969 | 0.626 | 1.6E-08 |
| 77091 | Genus | Clostridium | -4.247 | 1.426 | 0.039 |

Differential analysis using DESeq2 yielded significant (adjusted p-value <0.05) differentially abundant taxa for the Blautix treatment vs. Vehicle as well as Blautix treatment vs. Lyobuffer for the Stroke study timepoints, as shown in Table 6. The taxa are listed in Table 7, Table 8 and Table 9.

TABLE 6

Significant differentially abundant taxa for the Blautix treatment in the Stroke study.

| | D-14 | D14 | D28 |
|---|---|---|---|
| Blautix vs. Vehicle | 0 | 10 | 0 |
| Blautix vs. Lyobuffer | 2 | 13 | 0 |

TABLE 7

Significant differentially abundant taxa for the Blautix treatment vs. Vehicle at D14 in the Stroke study.

| OTU_ID | Lowest Level | Classification | log2 fold change | st error | adjusted p-value |
|---|---|---|---|---|---|
| 25678 | Species | Mucispirillum schaedleri | 2.604 | 0.688 | 0.014 |
| 3119687 | Family | Lachnospiraceae | 2.445 | 0.642 | 0.014 |
| 321825 | Family | Ruminococcaceae | 2.174 | 0.564 | 0.014 |
| 627 | Genus | Clostridium XIVa | 1.915 | 0.601 | 0.043 |
| 308030 | Species | Barnesiella intestinihominis | -1.324 | 0.419 | 0.043 |
| 1370810 | Species | Barnesiella intestinihominis | -1.540 | 0.425 | 0.019 |
| 187271 | Species | Ruminococcus flavefaciens | -3.475 | 1.065 | 0.042 |
| 277773 | Species | Alistipes finegoldii | -3.751 | 1.178 | 0.043 |
| 940566 | Species | Staphylococcus lentus | -5.228 | 1.519 | 0.026 |
| 930972 | Genus | Staphylococcus | -5.418 | 1.536 | 0.023 |

TABLE 8

Significant differentially abundant taxa for the Blautix treatment vs. Lyobuffer at D-14 in the Stroke study

| OTU_ID | Lowest Level | Classification | log2 fold change | st error | adjusted p-value |
|---|---|---|---|---|---|
| 1161472 | Family | Lachnospiraceae | 6.511 | 1.403 | 0.001 |
| 392940 | Kingdom | Bacteria | -5.169 | 1.346 | 0.022 |

TABLE 9

Significant differentially abundant taxa for the Blautix treatment vs. Lyobuffer at D14 in the Stroke study

| OTU_ID | Lowest Level | Classification | log2 fold change | st error | adjusted p-value |
|---|---|---|---|---|---|
| 25678 | Species | Mucispirillum schaedleri | 2.704 | 0.753 | 0.012 |

TABLE 9-continued

Significant differentially abundant taxa for the Blautix treatment vs. Lyobuffer at D14 in the Stroke study

| OTU_ID | Lowest Level | Classification | log2 fold change | st error | adjusted p-value |
|---|---|---|---|---|---|
| 1379349 | Genus | Clostridium XIVa | 2.517 | 0.771 | 0.027 |
| 742656 | Species | Oscillibacter valericigenes | 1.738 | 0.459 | 0.009 |
| 558330 | Genus | Prevotella | −1.634 | 0.406 | 0.006 |
| 1370810 | Species | Barnesiella intestinihominis | −1.780 | 0.390 | 0.001 |
| 712755 | Species | Barnesiella intestinihominis | −1.827 | 0.464 | 0.006 |
| 47662 | Species | Barnesiella intestinihominis | −2.109 | 0.606 | 0.014 |
| 1640334 | Species | Barnesiella intestinihominis | −2.260 | 0.693 | 0.027 |
| 1105465 | Genus | Barnesiella | −2.306 | 0.627 | 0.010 |
| 161658 | Family | Lachnospiraceae | −2.565 | 0.816 | 0.037 |
| 277773 | Species | Alistipes finegoldii | −3.619 | 1.034 | 0.014 |
| 187271 | Species | Rum inococcus flavefaciens | −3.924 | 1.057 | 0.010 |
| 459041 | Species | Lactobacillus johnsonii | −4.029 | 0.981 | 0.006 |

Summary

Blautix effects a significant increase in microbiota diversity throughout the period of the study in a mouse model of stroke, when compared to lyobuffer or vehicle control.

EXAMPLE 4—Protective Effect in Models of Neuroinflammatory Conditions

Experimental Autoimmune Encephalomyelitis (EAE) is a mouse model of CNS inflammation that mirrors many aspects of the human disease MS and EAE is the most commonly used experimental model for human MS. EAE is also used more generally as a model for CNS-specific autoimmune disorders [52] and for other specific conditions, including acute disseminated encephalomyelitis. EAE is induced using immunisation with myelin peptides and adjuvants to elicit an immune and inflammatory response that closely corresponds to the mechanisms underlying many autoimmune and inflammatory disorders of the CNS, and in particular MS. Many therapies showing efficacy in EAE have also shown efficacy in treatment of MS in human patients [52]. Most importantly, EAE reproduces key features of MS, including inflammation, demyelination, axonal loss and gliosis. The effects of demyelination are mainly restricted to the spinal cord in EAE, with little alteration of the brain stem and the cerebellum. In EAE the CD4+ T cells are the dominant cell population found in the CNS.

Methodology

Blautia hydrogenotrophica ("Blautix", strain deposited under accession number DSM 10507 and also under accession number DSM 14294) was used as a freeze-dried powder and reconstituted as required.

12 adult female C57BL/6J mice were used.

On Day 0 and Day 7, animals were administered with an emulsion containing MOG35-55 and complete Freund's adjuvant (CFA) supplemented with Mycobacterium Tuberculosis H37Ra by subcutaneous injections under gas (isoflurane) anaesthesia. On Day 0, two subcutaneous injections were performed in the flanks; one in each of the lower quadrant of the back. On Day 7, two subcutaneous injections were performed in the flanks, one in each of the upper quadrant of the back.

On Day 0 and Day 2, animals were administered with pertussis toxin (PTx) in phosphate buffered saline (PBS) by intra-peritoneal injections. On Day 0, PTx administration was performed after MOG injections.

Treatments with Blautix or controls were administered from Day −14 according to the following schedule:
Day 0: MOG/CFA, once, SC
Day 0: PTx, once, IP
Day 2: PTx, once, IP
Day 7: MOG/CFA, once, SC Treatments were administered within 15 minutes of their preparation. Blautix was administered at a dose of 2×10 s; 100 μl/mouse.

From Day 0 until the end of the experiment, animals were scored daily for clinical signs of EAE, including paresis and paralysis of the tail and/or limbs.

On Day −14, Day −1 and Day 34, faecal pellets were collected from each animal, immediately snap-frozen and stored at −80° C.

Results

Figure 10:
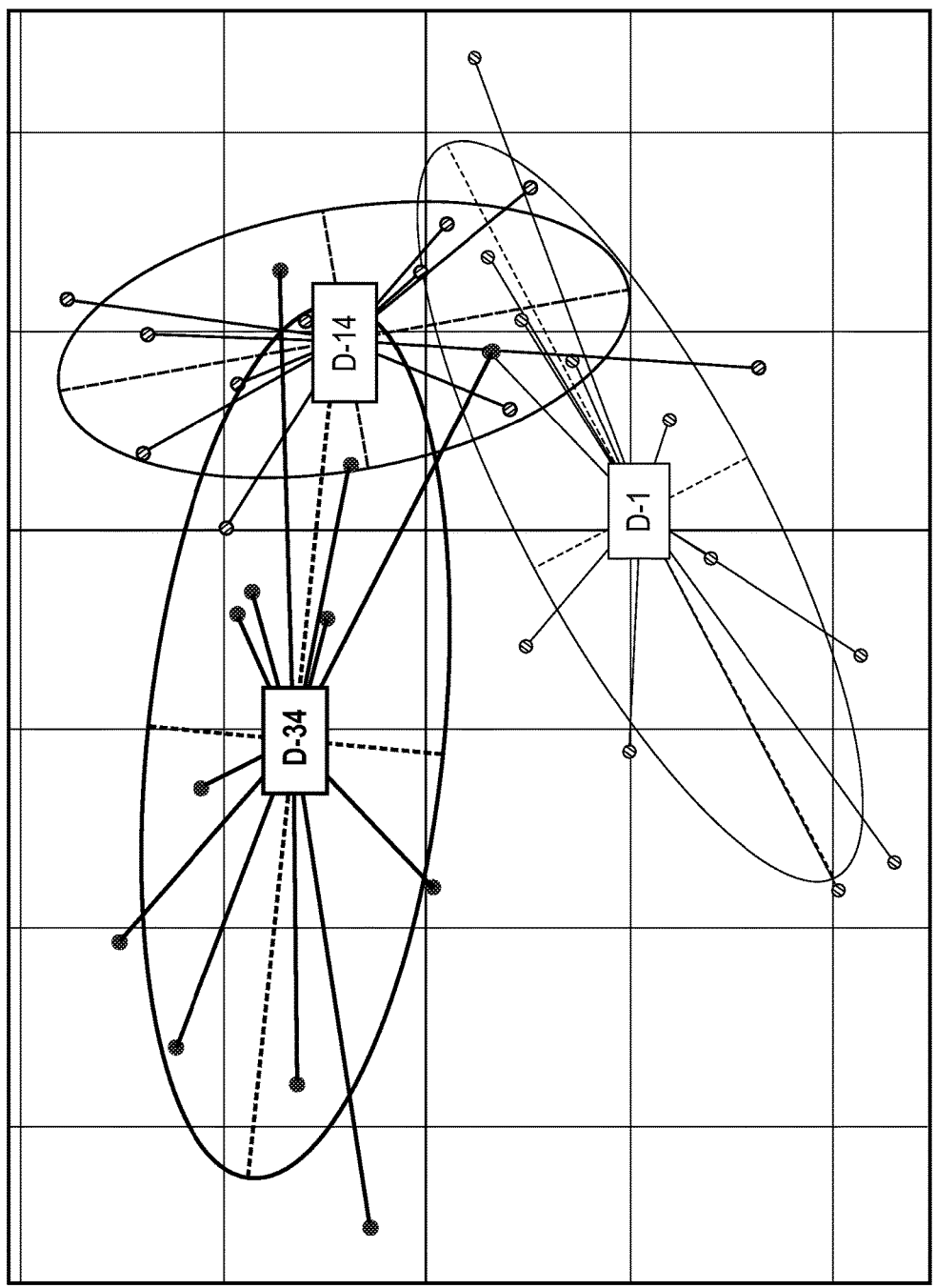
FIG. 10: Comparison of microbiota profiles for Blautix treatment at study timepoints (D-14, D-1, D34) based on Bray-Curtis dissimilarities.

The effect of Blautix treatment on microbiota between timepoints (D-14, D-1, D34) for the MS model is shown in FIG. 10. Significant temporal variation in the microbiota profiles was observed (p-value=0.001) for the study timepoints.

Differential analysis using DESeq2 yielded significant (adjusted p-value<0.05) differentially abundant taxa for the Blautix treatment between study timepoints, as shown in Table 10. The taxa are listed in Table 11, Table 12 and Table 13.

TABLE 10

Significant differentially abundant taxa between timepoints in the MS study.

| — | D-14 −> D-1 | D-1 −> D34 | D-14 −> D34 |
|---|---|---|---|
| MS (Blautix) | 42 | 30 | 58 |

TABLE 11

Significant differentially abundant taxa between D-14 and D-1 timepoints in the MS study. A positive fold change is interpreted as increased at D-1 when compared to D-14.

| OTU_ID | Lowest Level | Classification | log2 fold change | st error | adjusted p-value |
|---|---|---|---|---|---|
| 1105465 | Genus | Barnesiella | 8.076 | 0.702 | 2.2E−28 |
| 48633 | Genus | Clostridium XIVa | 7.304 | 0.825 | 7.0E−17 |
| 490405 | Species | Turicibacter sanguinis | 6.824 | 0.778 | 1.0E−16 |
| 491106 | Species | Flavonifractor plautii | 5.116 | 0.923 | 4.3E−07 |
| 43241 | Genus | Clostridium XIVa | 5.041 | 0.739 | 2.2E−10 |
| 948888 | Genus | Barnesiella | 4.649 | 0.605 | 4.3E−13 |
| 47662 | Species | Barnesiella intestinihominis | 4.276 | 0.501 | 5.1E−16 |

TABLE 11-continued

Significant differentially abundant taxa between D-14 and D-1 timepoints in the MS study. A positive fold change is interpreted as increased at D-1 when compared to D-14.

| OTU_ID | Lowest Level | Classification | log2 fold change | st error | adjusted p-value |
|---|---|---|---|---|---|
| 1288839 | Family | Lachnospiraceae | 4.117 | 1.170 | 0.003 |
| 11297 | Family | Porphyromonadaceae | 4.081 | 0.600 | 2.2E-10 |
| 198591 | Family | Lachnospiraceae | 3.757 | 0.788 | 2.3E-05 |
| 49543 | Family | Lachnospiraceae | 3.275 | 0.897 | 0.002 |
| 1009304 | Species | Oscillospira guilliermondii | 3.140 | 1.043 | 0.015 |
| 930464 | Species | Insolitispirillum peregrinum | 2.804 | 1.033 | 0.029 |
| 1793164 | Genus | Parasutterella | 2.720 | 0.576 | 2.6E-05 |
| 1260915 | Kingdom | Bacteria | 2.678 | 0.804 | 0.006 |
| 36112 | Species | Clostridium leptum | 2.584 | 0.887 | 0.018 |
| 181003 | Genus | Alistipes | 2.581 | 0.555 | 3.3E-05 |
| 149837 | Family | Lachnospiraceae | 2.434 | 0.678 | 0.002 |
| 1056232 | Genus | Clostridium XIVa | 2.308 | 0.856 | 0.030 |
| 770554 | Species | Alistipes putredinis | 2.223 | 0.556 | 0.001 |
| 1176501 | Family | Lachnospiraceae | 2.079 | 0.758 | 0.028 |
| 33530 | Species | Acetatifactor muris | 1.965 | 0.569 | 0.004 |
| 43033 | Genus | Alistipes | 1.788 | 0.379 | 2.6E-05 |
| 576748 | Family | Ruminococcaceae | 1.740 | 0.603 | 0.019 |
| 50759 | Species | Oscillospira guilliermondii | 1.570 | 0.409 | 0.001 |
| 592877 | Species | Pseudoflavonifractor capillosus | 1.512 | 0.418 | 0.002 |
| 712755 | Species | Barnesiella intestinihominis | 1.509 | 0.502 | 0.015 |
| 375558 | Species | Barnesiella intestinihominis | 1.505 | 0.554 | 0.029 |
| 307526 | Species | Bacteroides acidifaciens | 1.499 | 0.492 | 0.014 |
| 74641 | Species | Bacteroides acidifaciens | 1.418 | 0.532 | 0.032 |
| 943687 | Family | Porphyromonadaceae | 1.162 | 0.397 | 0.018 |
| 791734 | Genus | Clostridium XIVa | -1.064 | 0.377 | 0.023 |
| 19031 | Species | Anaerotruncus colihominis | -1.391 | 0.516 | 0.030 |
| 74179 | Species | Alistipes massiliensis | -1.810 | 0.305 | 4.7E-08 |
| 211238 | Species | Anaeroplasma abactoclasticum | -2.662 | 0.859 | 0.012 |
| 76239 | Family | Lachnospiraceae | -2.721 | 0.668 | 4.2E-04 |
| 743544 | Genus | Clostridium XIVa | -3.014 | 0.672 | 7.0E-05 |
| 993522 | Genus | Clostridium XIVa | -3.394 | 0.708 | 2.2E-05 |
| 76325 | Genus | Lactobacillus | -3.621 | 0.575 | 5.2E-09 |
| 209309 | Family | Lachnospiraceae | -3.857 | 1.295 | 0.016 |
| 567799 | Genus | Alistipes | -5.435 | 0.634 | 4.3E-16 |
| 77091 | Genus | Clostridium | -6.877 | 1.048 | 1.0E-09 |

TABLE 12

Significant differentially abundant taxa between D-1 and D34 timepoints in the MS study. A positive fold change is interpreted as increased at D34 when compared to D-1.

| OTU_ID | Lowest Level | Classification | log2 fold change | st error | adjusted p-value |
|---|---|---|---|---|---|
| 1370810 | Species | Barnesiella intestinihominis | 4.794 | 1.196 | 0.001 |
| 1684470 | Species | Parasutterella excrementihominis | 4.434 | 1.167 | 0.002 |
| 1070245 | Species | Eubacterium plexicaudatum | 3.870 | 0.961 | 0.001 |
| 518034 | Species | Desulfovibrio fairfieldensis | 3.867 | 0.962 | 0.001 |
| 1482481 | Species | Clostridium disporicum | 3.228 | 1.112 | 0.029 |
| 567799 | Genus | Alistipes | 3.218 | 0.864 | 0.002 |
| 1404432 | Species | Bacteroides acidifaciens | 2.978 | 0.835 | 0.004 |
| 1067514 | Genus | Barnesiella | 2.967 | 0.921 | 0.011 |
| 76325 | Genus | Lactobacillus | 2.893 | 0.683 | 0.001 |
| 307526 | Species | Bacteroides acidifaciens | 2.218 | 0.351 | 1.8E-08 |
| 1288839 | Family | Lachnospiraceae | 2.084 | 0.746 | 0.035 |
| 866478 | Species | Barnesiella intestinihominis | 1.936 | 0.647 | 0.022 |
| 23133 | Family | Ruminococcaceae | 1.840 | 0.544 | 0.007 |
| 472737 | Family | Lachnospiraceae | 1.697 | 0.524 | 0.011 |
| 842401 | Order | Clostridiales | 1.601 | 0.535 | 0.022 |
| 39008 | Species | Bacteroides acidifaciens | 1.494 | 0.390 | 0.002 |
| 74179 | Species | Alistipes massiliensis | 1.426 | 0.328 | 3.9E-04 |
| 277773 | Species | Alistipes finegoldii | 1.323 | 0.461 | 0.029 |
| 76234 | Family | Lachnospiraceae | -1.183 | 0.333 | 0.004 |
| 948888 | Genus | Barnesiella | -1.453 | 0.520 | 0.035 |
| 150155 | Family | Lachnospiraceae | -1.609 | 0.421 | 0.002 |
| 783115 | Family | Desulfovibrionaceae | -2.262 | 0.608 | 0.002 |
| 773427 | Species | Anaerotruncus colihominis | -2.443 | 0.661 | 0.003 |
| 201157 | Family | Lachnospiraceae | -2.587 | 0.754 | 0.006 |
| 596894 | Genus | Clostridium XIVa | -2.616 | 0.909 | 0.029 |
| 43033 | Genus | Alistipes | -3.236 | 0.718 | 2.2E-04 |
| 1793164 | Genus | Parasutterella | -3.758 | 0.632 | 1.4E-07 |

TABLE 12-continued

Significant differentially abundant taxa between D-1 and D34 timepoints in the MS study. A positive fold change is interpreted as increased at D34 when compared to D-1.

| OTU_ID | Lowest Level | Classification | log2 fold change | st error | adjusted p-value |
|---|---|---|---|---|---|
| 49543 | Family | Lachnospiraceae | −4.849 | 0.920 | 5.5E−06 |
| 490405 | Species | Turicibacter sanguinis | −5.152 | 0.704 | 2.5E−11 |
| 48282 | Family | Lachnospiraceae | −5.460 | 0.666 | 4.7E−14 |

TABLE 13

Significant differentially abundant taxa between D-14 and D34 timepoints in the MS study. A positive fold change is interpreted as increased at D34 when compared to D-14.

| OTU_ID | Lowest Level | Classification | log2 fold change | st error | adjusted p-value |
|---|---|---|---|---|---|
| 1105465 | Genus | Barnesiella | 7.221 | 0.754 | 2.1E−19 |
| 48633 | Genus | Clostridium XIVa | 6.734 | 0.959 | 8.7E−11 |
| 1288839 | Family | Lachnospiraceae | 5.820 | 0.811 | 3.5E−11 |
| 518034 | Species | Desulfovibrio fairfieldensis | 5.459 | 0.999 | 8.3E−07 |
| 1684470 | Species | Parasutterella excrementihominis | 5.289 | 1.408 | 0.001 |
| 1482481 | Species | Clostridium disporicum | 4.947 | 1.295 | 0.001 |
| 1370810 | Species | Barnesiella intestinihominis | 4.734 | 1.263 | 0.001 |
| 1070245 | Species | Eubacterium plexicaudatum | 4.620 | 0.794 | 1.3E−07 |
| 1067514 | Genus | Barnesiella | 4.544 | 1.103 | 2.8E−04 |
| 1575843 | Species | Clostridium ruminantium | 4.393 | 1.743 | 0.040 |
| 43241 | Genus | Clostridium XIVa | 4.284 | 0.817 | 2.4E−06 |
| 47662 | Species | Barnesiella intestinihominis | 4.273 | 0.478 | 3.8E−17 |
| 1728285 | Genus | Lachnospiracea incertae sedis | 4.204 | 1.221 | 0.003 |
| 11297 | Family | Porphyromonadaceae | 3.921 | 0.577 | 3.4E−10 |
| 307526 | Species | Bacteroides acidifaciens | 3.539 | 0.534 | 9.9E−10 |
| 198591 | Family | Lachnospiraceae | 3.273 | 0.762 | 1.4E−04 |
| 236126 | Species | Oscillospira guilliermondii | 3.175 | 1.086 | 0.015 |
| 930464 | Species | Insolitispirillum peregrinum | 3.152 | 0.848 | 0.001 |
| 948888 | Genus | Barnesiella | 3.040 | 0.629 | 1.6E−05 |
| 491106 | Species | Flavonifractor plautii | 3.039 | 1.170 | 0.034 |
| 563211 | Family | Lachnospiraceae | 2.564 | 0.965 | 0.030 |
| 149837 | Family | Lachnospiraceae | 2.562 | 0.890 | 0.016 |
| 770554 | Species | Alistipes putredinis | 2.520 | 0.455 | 6.2E−07 |
| 1260915 | Kingdom | Bacteria | 2.505 | 0.677 | 0.001 |
| 36112 | Species | Clostridium leptum | 2.483 | 0.916 | 0.026 |
| 1056232 | Genus | Clostridium XIVa | 2.319 | 0.664 | 0.002 |
| 39008 | Species | Bacteroides acidifaciens | 2.107 | 0.274 | 9.9E−13 |
| 23133 | Family | Ruminococcaceae | 2.049 | 0.614 | 0.004 |
| 74641 | Species | Bacteroides acidifaciens | 2.002 | 0.457 | 1.0E−04 |
| 712755 | Species | Barnesiella intestinihominis | 1.977 | 0.470 | 2.0E−04 |
| 277773 | Species | Alistipes finegoldii | 1.881 | 0.388 | 1.6E−05 |
| 1404432 | Species | Bacteroides acidifaciens | 1.805 | 0.563 | 0.006 |
| 1176501 | Family | Lachnospiraceae | 1.654 | 0.630 | 0.032 |
| 544582 | Species | Flavonifractor plautii | 1.418 | 0.540 | 0.032 |
| 76234 | Family | Lachnospiraceae | −0.991 | 0.389 | 0.038 |
| 80190 | Family | Lachnospiraceae | −1.113 | 0.348 | 0.006 |
| 182471 | Order | Clostridiales | −1.315 | 0.472 | 0.021 |
| 494032 | Species | Clostridium oroticum | −1.502 | 0.580 | 0.034 |
| 2367602 | Order | Clostridiales | −1.518 | 0.472 | 0.006 |
| 74771 | Species | Alistipes massiliensis | −1.617 | 0.408 | 0.001 |
| 172154 | Genus | Clostridium XIVa | −1.628 | 0.442 | 0.001 |
| 993522 | Genus | Clostridium XIVa | −1.799 | 0.594 | 0.011 |
| 791734 | Genus | Clostridium XIVa | −1.842 | 0.387 | 2.2E−05 |
| 150155 | Family | Lachnospiraceae | −1.859 | 0.532 | 0.002 |
| 743544 | Genus | Clostridium XIVa | −2.196 | 0.558 | 0.001 |
| 567799 | Genus | Alistipes | −2.378 | 0.513 | 3.9E−05 |
| 96345 | Genus | Clostridium XIVa | −2.528 | 0.667 | 0.001 |
| 19031 | Species | Anaerotruncus colihominis | −2.575 | 0.610 | 1.9E−04 |
| 201157 | Family | Lachnospiraceae | −2.615 | 0.866 | 0.011 |
| 578360 | Family | Lachnospiraceae | −2.870 | 0.586 | 1.4E−05 |
| 76239 | Family | Lachnospiraceae | −3.325 | 0.631 | 2.3E−06 |
| 1165458 | Family | Lachnospiraceae | −3.346 | 0.754 | 8.1E−05 |
| 773427 | Species | Anaerotruncus colihominis | −3.475 | 0.776 | 7.0E−05 |
| 209309 | Family | Lachnospiraceae | −3.639 | 1.042 | 0.002 |
| 320120 | Genus | Clostridium XIVa | −3.670 | 0.811 | 5.9E−05 |
| 1628488 | Species | Vallitalea guaymasensis | −4.144 | 1.538 | 0.027 |
| 48282 | Family | Lachnospiraceae | −4.653 | 1.012 | 4.5E−05 |
| 77091 | Genus | Clostridium | −7.493 | 1.192 | 7.9E−09 |

Summary

Blautix effects a significant increase in microbiota diversity and results in significant temporal variation during treatment in an animal model for multiple sclerosis.

The invention has been described above by way of example only and it will be understood that further modifications may be made which fall within the scope of the claims.

Sequences

```
SEQ ID NO: 1 (Blautia stercoris strain GAM6-1 16S ribosomal RNA gene,
partial sequence - HM626177)
   1    tgcaagtcga gcgaagcgct tacgacagaa ccttcggggg aagatgtaag ggactgagcg
  61    gcggacgggt gagtaacgcg tgggtaacct gcctcataca gggggataac agttggaaac
 121    ggctgctaat accgcataag cgcacggtat cgcatgatac agtgtgaaaa actccggtgg
 181    tatgagatgg acccgcgtct gattagctag ttggaggggt aacggcccac caaggcgacg
 241    atcagtagcc ggcctgagag ggtgaacggc cacattggga ctgagacacg gcccagactc
 301    ctacggagg cagcagtggg gaatattgca caatggggga aaccctgatg cagcgacgcc
 361    gcgtgaagga agaagtatct cggtatgtaa acttctatca gcagggaaga aaatgacggt
 421    acctgactaa gaagcccgg ctaactacgt gccagcagcc gcggtaatac gtaggggggca
 481    agcgttatcc ggatttactg ggtgtaaagg gagcgtagac ggaagagcaa gtctgatgtg
 541    aaaggctggg gcttaacccc aggactgcat tggaaactgt ttttcttgag tgccggagag
 601    gtaagcggaa ttcctagtgt agcggtgaaa tgcgtagata ttaggaggaa caccagtggc
 661    gaaggcggct tactgacgg taactgacgt tgaggctcga aagcgtgggg agcaaacagg
 721    attagatacc ctggtagtcc acgccgtaaa cgatgaatac taggtgttgg ggagcaaagc
 781    tcttcggtgc cgcagcaaac gcaataagta ttccacctgg ggagtacgtt cgcaagaatg
 841    aaactcaaag gaattgacgg ggacccgcac aagcggtgga gcatgtggtt taattcgaag
 901    caacgcgaag aaccttacca agtcttgaca tcgatctgac cggttcgtaa tggaaccttt
 961    ccttcgggac agagaagaca ggtggtgcat ggttgtcgtc agctcgtgtc gtgagatgtt
1021    gggttaagtc ccgcaacgag cgcaaccct atcctcagta gccagcaggt gaagctgggc
1081    actctgtgga gactgccagg gataacctgg aggaaggcgg ggacgacgtc aaatcatcat
1141    gccccttatg atttgggcta cacacgtgct acaatggcgt aaacaaaggg aagcgagccc
1201    gcgagggga gcaaatccca aaaataacgt cccagttcgg actgcagtct gcaactcgac
1261    tgcacgaagc tggaatcgct agtaatcgcg aatcagaatg tcgcggtgaa tacgttcccg
1321    ggtcttgtac acaccgcccg tcacaccatg ggagtcagta acgcccgaag tc SEQ ID NO: 2 (Blautia wexlerae strain WAL 14507 16S ribosomal RNA gene,
partial sequence - EF036467)
   1    caagtcgaac gggaattant ttattgaaac ttcggtcgat ttaatttaat tctagtggcg
  61    gacgggtgag taacgcgtgg gtaacctgcc ttatacaggg gataacagt cagaaatggc
 121    tgctaatacc gcataagcgc acagagctgc atggctcagt gtgaaaaact ccggtggtat
 181    aagatggacc cgcgttggat tagcttgttg gtggggtaac ggcccaccaa ggcgacgatc
 241    catagccggc ctgagagggt gaacggccac attgggactg agacacggcc cagactccta
 301    cgggaggcag cagtggggaa tattgcacaa tgggggaaac cctgatgcag cgacgccgcg
 361    tgaaggaaga agtatctcgg tatgtaaact tctatcagca gggaagatag tgacggtacc
 421    tgactaagaa gccccggcta actacgtgcc agcagccgcg gtaatacgta gggggcaagc
 481    gttatccgga tttactgggt gtaaaggag cgtagacggt gtggcaagtc tgatgtgaaa
 541    ggcatgggct caacctgtgg actgcattgg aaactgtcat acttgagtgc cggagggta
```

-continued

```
 601 agcggaattc ctagtgtagc ggtgaaatgc gtagatatta ggaggaacac cagtggcgaa
 661 ggcggcttac tggacggtaa ctgacgttga ggctcgaaag cgtggggagc aaacaggatt
 721 agataccctg gtagtccacg ccgtaaacga tgaataacta ggtgtcgggt ggcaaagcca
 781 ttcggtgccg tcgcaaacgc agtaagtatt ccacctgggg agtacgttcg caagaatgaa
 841 actcaaagga attgacgggg acccgcacaa gcggtggagc atgtggttta attcgaagca
 901 acgcgaagaa ccttaccaag tcttgacatc cgcctgaccg atccttaacc ggatctttcc
 961 ttcgggacag gcgagacagg tggtgcatgg ttgtcgtcag ctcgtgtcgt gagatgttgg
1021 gttaagtccc gcaacgagcg caaccccctat cctcagtagc cagcatttaa ggtgggcact
1081 ctgggagac tgccagggat aacctggagg aaggcgggga tgacgtcaaa tcatcatgcc
1141 ccttatgatt tgggctacac acgtgctaca atggcgtaaa caaaggaag cgagattgtg
1201 agatggagca atcccaaaa ataacgtccc agttcggact gtagtctgca acccgactac
1261 acgaagctgg aatcgctagt aatcgcggat cagaatgccg cggtgaatac gttcccgggt
1321 cttgtacaca ccgcccgtca ccatgggga gtcagtaacg cccgaagtca gtgacctaac
1381 tgcaaagaag gagctgccga aggcgggacc gatgactggg gtgaagtcgt aacaaggt
```

SEQ ID NO: 3 (consensus 16S rRNA sequence for Blautia stercoris strain 830)
TTTKGTCTGGCTCAGGATGAACGCTGGCGGCGTGCTTAACACATGCAAGTCGAGCGAAGCGCTTACGACAGAACCTT

CGGGGGAAGATGTAAGGGACTGAGCGGCGGACGGGTGAGTAACGCGTGGGTAACCTGCCTCATACAGGGGGATAACA

GTTGGAAACGGCTGCTAATACCGCATAAGCGCACAGTATCGCATGATACAGTGTGAAAAACTCCGGTGGTATGAGAT

GGACCCGCGTCTGATTAGCTAGTTGGAGGGGTAACGGCCCACCAAGGCGACGATCAGTAGCCGGCCTGAGAGGGTGA

ACGGCCACATTGGGACTGAGACACGGCCCAGACTCCTACGGGAGGCAGCAGTGGGGAATATTGCACAATGGGGGAAA

CCCTGATGCAGCGACGCCGCGTGAAGGAAGAAGTATCTCGGTATGTAAACTTCTATCAGCAGGGAAGAAAATGACGG

TACCTGACTAAGAAGCCCCGGCTAACTACGTGCCAGCAGCCGCGGTAATACGTAGGGGGCAAGCGTTATCCGGATTT

ACTGGGTGTAAAGGGAGCGTAGACGGAAGAGCAAGTCTGATGTGAAAGGCTGGGCTTAACCCCAGGACTGCATTGG

AAACTGTTTTTCTTGAGTGCCGGAGAGGTAAGCGGAATTCCTAGTGTAGCGGTGAAATGCGTAGATATTAGGAGGAA

CACCAGTGGCGAAGGCGGCTTACTGGACGGTAACTGACGTTGAGGCTCGAAAGCGTGGGGAGCAAACAGGATTAGAT

ACCCTGGTAGTCCACGCCGTAAACGATGAATACTAGGTGTTGGGGAGCAAAGCTCTTCGGTGCCGCAGCAAACGCAA

TAAGTATTCCACCTGGGGAGTACGTTCGCAAGAATGAAACTCAAAGGAATTGACGGGGACCCGCACAAGCGGTGGAG

CATGTGGTTTATTCGAAGCAACGCGAAGAACCTTACCAAGTCTTGACATCGATCTGACCGGTTCGTAATGGAACCTT

TCCTTCGGGACAGAGAAGACAGGTGGTGCATGGTTGTCGTCAGCTCGTGTCGTGAGATGTTGGGTTAAGTCCCGCAA

CGAGCGCAACCCCTATCGTCAGTAGCCAGCAGGTAAAGCTGGGCACTCTGAGGAGACTGCCAGGGATAACCTGGAGG

AAGGCGGGGACGACGTCAAATCATCATGCCCCTTATGATTTGGGCTACACACGTGCTACAATGGCGTAAACAAAGGG

AAGCGAGCCCGCGAGGGGAGCAAATCCCAAAAATAACGTCCCAGTTCGGACTGCAGTCTGCAACTCGACTGCACGA

AGCTGGAATCGCTAGTAATCGCGAATCAGAATGTCGCGGTGAATACGTTCCCGGGTCTTGTACACACCGCCCGTCAC

ACCATGGGAGTCAGTAACGCCCGAAGTCAGTGACCCAACCTTAGGGAGGGAGCTGCCGAAGGCGGGATTGATAACTG

GGGTGAAGTCTAGGGGGT

SEQ ID NO: 4 (consensus 16S rRNA sequence for *Blautia wexlerae* strain MRX008)
TTCATTGAGACTTCGGTGGATTTAGATTCTATTTCTAGTGGCGGACGGGTGAGTAACGCGTGGGTAACCTGCCTTAT

ACAGGGGGATAACAGTCAGAAATGGCTGCTAATACCGCATAAGCGCACAGAGCTGCATGGCTCAGTGTGAAAAACTC

CGGTGGTATAAGATGGACCCGCGTTGGATTAGCTTGTTGGTGGGGTAACGGCCCACCAAGGCGACGATCCATAGCCG

GCCTGAGAGGGTGAACGGCCACATTGGGACTGAGACACGGCCCAGACTCCTACGGGAGGCAGCAGTGGGGAATATTG

CACAATGGGGAAACCCTGATGCAGCGACGCCGCGTGAAGGAAGAAGTATCTCGGTATGTAAACTTCTATCAGCAGG

GAAGATAGTGACGGTACCTGACTAAGAAGCCCCGGCTAACTACGTGCCAGCAGCCGCGGTAATACGTAGGGGGCAAG

CGTTATCCGGATTTACTGGGTGTAAAGGGAGCGTAGACGGTGTGGCAAGTCTGATGTGAAAGGCATGGGCTCAACCT

GTGGACTGCATTGGAAACTGTCATACTTGAGTGCCGGAGGGGTAAGCGGAATTCCTAGTGTAGCGGTGAAATGCGTA

GATATTAGGAGGAACACCAGTGGCGAAGGCGGCTTACTGGACGGTAACTGACGTTGAGGCTCGAAAGCGTGGGGAGC

AAACAGGATTAGATACCCTGGTAGTCCACGCCGTAAACGATGAATACTAGGTGTCNGGGGAGCATGGCTCTTCGGTG

CCGTCGCAAACGCAGTAAGTATTCCACCTGGGGAGTACGTTCGCAAGAATGAAACTCAAAGGAATTGACGGGACCC

GCACAAGCGGTGGAGCATGTGGTTTAATTCGAAGCAACGCGAAGAACCTTACCAAGTCTTGACATCCGCCTGACCGA

TCCTTAACCGGATCTTTCCTTCGGGACAGGCGAGACAGGTGGTGCATGGTTGTCGTCAGCTCGTGTCGTGAGATGTT

GGGTTAAGTCCCGCAACGAGCGCAACCCCTATCCTCAGTAGCCAGCATTTAAGGTGGGCACTCTGGGGAGACTGCCA

GGGATAACCTGGAGGAAGGCGGGGATGACGTCAAATCATCATGCCCCTTATGATTTGGGCTACACACGTGCTACAAT

GGCGTAAACAAAGGGAAGCGAGATCGTGAGATGGAGCAAATCCCAAAAATAACGTCCCAGTTCGGACTGTAGTCTGC

AACCCGACTACACGAAGCTGGAATCGCTAGTAATCGCGGATCAGAATGCCGCGGTGAATACGTTCCCGGGTCTTGTA

CACACCGCCCGTCACACCATGGGAGTCAGTAACGCCCGAAGTCAGTGACCTAACTGCAAAGAAGGAGCTGCCGAA

SEQ ID NO: 5 (*Blautia hydrogenotrophica* strain S5a36 16S ribosomal RNA
gene, partial sequence - X95624.1)
```
   1  gatgaacgct ggcggcgtgc ttaacacatg caagtcgaac gaagcgatag agaacggaga
  61  tttcggttga agttttctat tgactgagtg gcggacgggt gagtaacgcg tgggtaacct
 121  gccctataca ggggataac agttagaaat gactgctaat accgcataag cgcacagctt
 181  cgcatgaagc ggtgtgaaaa actgaggtgg tataggatgg acccgcgttg gattagctag
 241  ttggtgaggt aacggcccac caaggcgacg atccatagcc ggcctgagag ggtgaacggc
 301  cacattggga ctgagacacg gcccaaactc ctacgggagg cagcagtggg gaatattgca
 361  caatggggga aaccctgatg cagcgacgcc gcgtgaagga agaagtatct cggtatgtaa
 421  acttctatca gcagggaaga aagtgacggt acctgactaa gaagccccgg ctaattacgt
 481  gccagcagcc gcggtaatac gtaaggggca agcgttatcc ggatttactg ggtgtaaagg
 541  gagcgtagac ggtttggcaa gtctgatgtg aaaggcatgg gctcaacctg tggactgcat
 601  tggaaactgt cagacttgag tgccggagag gcaagcggaa ttcctagtgt agcggtgaaa
 661  tgcgtagata ttaggaggaa caccagtggc gaaggcggcc tgctggacgg taactgacgt
 721  tgaggctcga aagcgtgggg agcaaacagg attagatacc ctggtagtcc acgctgtaaa
 781  cgatgaatac taggtgtcgg gtggcaaagc cattcggtgc cgcagcaaac gcaataagta
 841  ttcccacctg gggagtacgt tcgcaagaat gaaactcaaa ggaattgacg ggacccgca
 901  caagcggtgg agcatgtggt ttaattcgaa gcaacgcgaa gaaccttacc aaatcttgac
 961  atccctctga ccggaagta atgttccctt tcttcggaa cagaggagac aggtggtgca
1021  tggttgtcgt cagctcgtgt cgtgagatgt tgggttaagt cccgcaacga gcgcaaccct
1081  tattcttagt agccagcagg tagagctggg cactctaggg agactgccag ggataacctg
1141  gaggaaggtg gggatgacgt caaatcatca tgccccttat gatttgggct acacacgtgc
```

```
1201  tacaatggcg taaacaaagg gaagcgaagg ggtgacctgg agcaaatctc aaaaataacg 1261  tctcagttcg gattgtagtc tgcaactcga ctacatgaag ctggaatcgc tagtaatcgc 1321  gaatcagaat gtcgcggtga atacgttccc gggtcttgta cacaccgccc gtcacaccat 1381  gggagtcagt aacgcccgaa gtcagtgacc caaccnaaag gagggagctg ccgaaggtgg 1441  gactgataac tggggtga
```

REFERENCES

[1] Spor et al. (2011) *Nat Rev Microbiol.* 9(4):279-90.
[2] Tap et al. (2009), *Environ Microbiol,* 11(10):2574-84
[3] Macpherson et al. (2001) *Microbes Infect.* 3(12):1021-35
[4] Macpherson et al. (2002) *Cell Mol Life Sci.* 59(12):2088-96.
[5] Mazmanian et al. (2005) *Cell* 15; 122(1):107-18.
[6] Frank et al. (2007) *PNAS* 104(34):13780-5.
[7] Scanlan et al. (2006) *J Clin Microbiol.* 44(11):3980-8.
[8] Kang et al. (2010) *Inflamm Bowel Dis.* 16(12):2034-42.
[9] Machiels et al. (2013) *Gut.* 63(8):1275-83.
[10] WO 2013/050792
[11] WO 03/046580
[12] WO 2013/008039
[13] WO 2014/167338
[14] Lee and Lee (2014) *World J Gastroenterol.* 20(27): 8886-8897.
[15] Xie et al. (2016) Journal Dairy Sci. 99:6913-6921
[16] WO 01/85187
[17] WO2016/086161
[18] Y Q et al. (2016), *J. Dig. Dis., "Therapeutic Modulation of the Gut Microbiota in IBD—More Questions to Be Answered"*, Oct. 15, 1751-2980, 12422, Epub ahead of print.
[19] Lozupone (2012). Nature. 2012 Sep. 13; 489 (7415): 220-230
[20] Claesson, et al. (2012) Nature, 488, 178-184.
[21] Hansen, et al., (2010), Curr. Opin. Gastroenterol., 26(6): 564-571.
[22] Turnbaugh et al. Nature, 457(7228): 480-484.
[23] Wang et al. (2009) ISME J. 3(8): 944-954.
[24] Faith et al. (2013), Science, 341(6141): 1237439
[25] Liu et al. (2008) *Int J Syst Evol Microbiol* 58, 1896-1902.
[26] Bernalier et al. (1996) *Arch. Microbiol.* 166 (3), 176-183.
[27] Park et al. (2012) *Int J Syst Evol Microbiol.* 62(Pt 4):776-9.
[28] Masco et al. (2003) *Systematic and Applied Microbiology,* 26:557-563.
[29] Srütkova et al. (2011) *J. Microbiol. Methods,* 87(1):10-6.
[30] Miyamoto-Shinohara et al. (2008) *J. Gen. Appl. Microbiol.,* 54, 9-24.
[31] Cryopreservation and Freeze-Drying Protocols, ed. by Day and McLellan, Humana Press.
[32] Leslie et al. (1995) *Appl. Environ. Microbiol.* 61, 3592-3597.
[33] Mitropoulou et al. (2013) *J Nutr Metab.* (2013) 716861.
[34] Kailasapathy et al. (2002) *Curr Issues Intest Microbiol.* 3(2):39-48.
[35] Handbook of Pharmaceutical Excipients, 2nd Edition, (1994), Edited by A Wade and PJ Weller
[36] Remington's Pharmaceutical Sciences, Mack Publishing Co. (A. R. Gennaro edit. 1985)
[37] US 2016/0067188
[38] *Handbook of Microbiological Media, Fourth Edition* (2010) Ronald Atlas, CRC Press.
[39] *Maintaining Cultures for Biotechnology and Industry* (1996) Jennie C. Hunter-Cevera, Academic Press
[40] Strobel (2009) *Methods Mol Biol.* 581:247-61.
[41] Gennaro (2000) *Remington: The Science and Practice of Pharmacy.* 20th edition, ISBN: 0683306472.
[42] *Molecular Biology Techniques: An Intensive Laboratory Course,* (Ream et al., eds., 1998, Academic Press).
[43] *Methods In Enzymology* (S. Colowick and N. Kaplan, eds., Academic Press, Inc.)
[44] *Handbook of Experimental Immunology,* Vols. I-IV (D. M. Weir and C. C. Blackwell, eds, 1986, Blackwell Scientific Publications)
[45] Sambrook et al. (2001) *Molecular Cloning: A Laboratory Manual,* 3rd edition (Cold Spring Harbor Laboratory Press).
[46] *Handbook of Surface and Colloidal Chemistry* (Birdi, K. S. ed., CRC Press, 1997)
[47] Ausubel et al. (eds) (2002) *Short protocols in molecular biology,* 5th edition (Current Protocols).
[48] PCR (*Introduction to Biotechniques Series*), 2nd ed. (Newton & Graham eds., 1997, Springer Verlag)
[49] *Current Protocols in Molecular Biology* (F. M. Ausubel et al., eds., 1987) Supplement 30
[50] Smith & Waterman (1981) *Adv. Appl. Math.* 2: 482-489.
[51] Meyza and Blanchard (2017) Neurosci Biobehav Rev.; 76(Pt A):99-110
[52] Constantinescu et al. (2011) *Br J Pharmacol.* 164(4): 1079-1106

The invention claimed is:

1. A method of increasing microbiotic diversity or maintaining microbiotic stability in a gastrointestinal tract of a subject in need thereof, comprising administering to the subject a pharmaceutical composition that comprises an effective amount of a bacteria strain of the species *Blautia hydrogenotrophica* sufficient for increasing microbiotic diversity or maintaining microbiotic stability in the gastrointestinal tract of the subject relative to an amount of microbiotic diversity or microbiotic stability prior to the administering, wherein the bacteria strain comprises a 16s rRNA gene sequence of SEQ ID NO:5, and wherein the administering results in an increase in an amount of a bacteria from at least one genus selected from *Clostridium*, *Bifidobacterium*, and *Prevotella* in the gastrointestinal tract of the subject relative to an amount of the respective bacteria prior to the administering.

2. The method of claim 1, wherein the bacteria strain is active.

3. The method of claim 1, wherein the bacteria strain is encapsulated in one or more capsules.

4. The method of claim 1, wherein the pharmaceutical composition comprises a pharmaceutically acceptable excipient, diluent, or carrier.

5. The method of claim 1, wherein the bacteria strain is lyophilized.

6. The method of claim 1, wherein the pharmaceutical composition is formulated for oral delivery.

7. The method of claim 6, wherein the pharmaceutical composition is enterically formulated.

8. The method of claim 1, wherein the pharmaceutical composition comprises from about $1 \times 10^3$ to about $1 \times 10^{11}$ colony forming units (CFU)/g of the bacteria strain with respect to a total weight of the pharmaceutical composition.

9. The method of claim 1, wherein the method is a method of increasing microbiotic diversity.

10. The method of claim 9, wherein prior to the administering the subject has a reduced microbiotic diversity relative to a healthy subject.

11. The method of claim 10, wherein the subject has less than 99 different bacterial species or less than 190 different bacterial strains in its microbiota.

12. The method of claim 1, wherein the method is a method of maintaining microbiotic stability.

13. The method of claim 10, wherein the administering is sufficient to treat a disease or disorder associated with the reduced microbiotic stability in the subject.

14. The method of claim 1, wherein the increasing microbiotic diversity or maintaining microbiotic stability is for non-acetogenic bacteria, or both acetogenic and non-acetogenic bacteria.

15. The method of claim 1, further comprising administering an additional therapeutic agent to the subject.

16. The method of claim 1, wherein at least 50% of the bacteria strain as measured by an amount of CFU, remains viable after about 1 year of storage when the pharmaceutical composition is stored in a closed container at 25° C. at 95% relative humidity.

17. The method of claim 1, wherein the amount of the bacteria from at least one genus selected from *Clostridium*, *Bifidobacterium*, and *Prevotella* is determined by measuring an amount of the respective bacteria in feces.

* * * * *

UNITED STATES PATENT AND TRADEMARK OFFICE
CERTIFICATE OF CORRECTION

PATENT NO. : 10,086,021 B2  
APPLICATION NO. : 15/915889  
DATED : October 2, 2018  
INVENTOR(S) : Ian Jeffery et al.

Page 1 of 1

It is certified that error appears in the above-identified patent and that said Letters Patent is hereby corrected as shown below:

On the Title Page

In Item (30), Foreign Application Priority Data:  
"Dec. 12, 2017 (GB) ................1621123.7"  
Should read:  
--Dec. 12, 2016 (GB)...............1621123.7--

Signed and Sealed this  
Seventeenth Day of November, 2020

Andrei Iancu  
*Director of the United States Patent and Trademark Office*

SEQUENCE LISTING

<160> NUMBER OF SEQ ID NOS: 5

<210> SEQ ID NO 1
<211> LENGTH: 1372
<212> TYPE: DNA
<213> ORGANISM: Blautia stercoris

<400> SEQUENCE: 1

```
tgcaagtcga gcgaagcgct tacgacagaa ccttcggggg aagatgtaag ggactgagcg    60
gcggacgggt gagtaacgcg tgggtaacct gcctcataca gggggataac agttggaaac   120
ggctgctaat accgcataag cgcacggtat cgcatgatac agtgtgaaaa actccggtgg   180
tatgagatgg acccgcgtct gattagctag ttggaggggt aacggcccac caaggcgacg   240
atcagtagcc ggcctgagag ggtgaacggc cacattggga ctgagacacg gcccagactc   300
ctacgggagg cagcagtggg gaatattgca caatggggga aaccctgatg cagcgacgcc   360
gcgtgaagga agaagtatct cggtatgtaa acttctatca gcagggaaga aaatgacggt   420
acctgactaa gaagcccegg ctaactacgt gccagcagcc gcggtaatac gtaggggca    480 agcgttatcc ggatttactg ggtgtaaagg gagcgtagac ggaagagcaa gtctgatgtg   540
aaaggctggg gcttaacccc aggactgcat tggaaactgt ttttcttgag tgccggagag   600
gtaagcggaa ttcctagtgt agcggtgaaa tgcgtagata ttaggaggaa caccagtggc   660
gaaggcggct tactgacgg taactgacgt tgaggctcga aagcgtgggg agcaaacagg   720
attagatacc ctggtagtcc acgccgtaaa cgatgaatac taggtgttgg ggagcaaagc   780
tcttcggtgc cgcagcaaac gcaataagta ttccacctgg ggagtacgtt cgcaagaatg   840
aaactcaaag gaattgacgg ggacccgcac aagcggtgga gcatgtggtt taattcgaag   900
caacgcgaag aaccttacca agtcttgaca tcgatctgac cggttcgtaa tggaacctt    960 ccttcgggac agagaagaca ggtggtgcat ggttgtcgtc agctcgtgtc gtgagatgtt  1020
gggttaagtc ccgcaacgag cgcaaccect atcctcagta gccagcaggt gaagctgggc  1080
actctgtgga gactgccagg gataacctgg aggaaggcgg ggacgacgtc aaatcatcat  1140
gccccttatg atttgggcta cacacgtgct acaatggcgt aaacaaaggg aagcgagccc  1200
gcgaggggga gcaaatccca aaaataacgt cccagttcgg actgcagtct gcaactcgac  1260
tgcacgaagc tggaatcgct agtaatcgcg aatcagaatg tcgcggtgaa tacgttcccg  1320
ggtcttgtac acaccgcccg tcacaccatg ggagtcagta acgcccgaag tc          1372
```

<210> SEQ ID NO 2
<211> LENGTH: 1438
<212> TYPE: DNA
<213> ORGANISM: Blautia wexlerae
<220> FEATURE:
<221> NAME/KEY: misc_feature
<222> LOCATION: 19
<223> OTHER INFORMATION: 'n' is a, c, g or t
<220> FEATURE:
<221> NAME/KEY: misc_feature
<222> LOCATION: 19
<223> OTHER INFORMATION: 'n' is a, c, g or t

<400> SEQUENCE: 2

```
caagtcgaac gggaattant ttattgaaac ttcggtcgat ttaatttaat tctagtggcg    60
gacgggtgag taacgcgtgg gtaacctgcc ttatacaggg ggataacagt cagaaatggc   120
tgctaatacc gcataagcgc acagagctgc atggctcagt gtgaaaaact ccggtggtat   180
aagatggacc cgcgttggat tagcttgttg gtggggtaac ggcccaccaa ggcgacgatc   240
catagccggc ctgagagggt gaacggccac attgggactg agacacgccc agactcctac   300
cgggaggcag cagtggggaa tattgcacaa tgggggaaac cctgatgcag cgacgccgcg   360
tgaaggaaga agtatctcgg tatgtaaact tctatcagca gggaagatag tgacggtacc   420
tgactaagaa gccccggcta actacgtgcc agcagccgcg gtaatacgta ggggcaagc   480 gttatccgga tttactgggt gtaaagggag cgtagacggt gtgcaagtc tgatgtgaaa   540
```

```
ggcatgggct caacctgtgg actgcattgg aaactgtcat acttgagtgc cggaggggta      600
agcggaattc ctagtgtagc ggtgaaatgc gtagatatta ggaggaacac cagtggcgaa      660
ggcggcttac tggacggtaa ctgacgttga ggctcgaaag cgtggggagc aaacaggatt      720
agataccctg gtagtccacg ccgtaaacga tgaataacta ggtgtcgggt ggcaaagcca      780
ttcggtgccg tcgcaaacgc agtaagtatt ccacctgggg agtacgttcg caagaatgaa      840
actcaaagga attgacgggg acccgcacaa gcggtggagc atgtggttta attcgaagca      900
acgcgaagaa ccttaccaag tcttgacatc cgcctgaccg atccttaacc ggatctttcc      960
ttcgggacag gcgagacagg tggtgcatgg ttgtcgtcag ctcgtgtcgt gagatgttgg     1020
gttaagtccc gcaacgagcg caaccccctat cctcagtagc cagcatttaa ggtgggcact     1080
ctggggagac tgccagggat aacctggagg aaggcgggga tgacgtcaaa tcatcatgcc     1140
ccttatgatt tgggctacac acgtgctaca atggcgtaaa caagggaag cgagattgtg     1200 agatggagca aatcccaaaa ataacgtccc agttcggact gtagtctgca acccgactac     1260
acgaagctgg aatcgctagt aatcgcggat cagaatgccg cggtgaatac gttcccgggt     1320
cttgtacaca ccgcccgtca caccatggga gtcagtaacg cccgaagtca gtgacctaac     1380
tgcaaagaag gagctgccga aggcgggacc gatgactggg gtgaagtcgt aacaaggt     1438
```

<210> SEQ ID NO 3
<211> LENGTH: 1481
<212> TYPE: DNA
<213> ORGANISM: Artificial Sequence
<220> FEATURE:
<223> OTHER INFORMATION: consensus 16s for Blautia stercoris

<400> SEQUENCE: 3

```
tttkgtctgg ctcaggatga acgctggcgg cgtgcttaac acatgcaagt cgagcgaagc       60
gcttacgaca gaaccttcgg gggaagatgt aagggactga gcggcggacg ggtgagtaac      120
gcgtgggtaa cctgcctcat acagggggat aacagttgga aacggctgct aataccgcat      180
aagcgcacag tatcgcatga tacagtgtga aaaactccgg tggtatgaga tggacccgcg      240
tctgattagc tagttggagg ggtaacggcc caccaaggcg acgatcagta gccggcctga      300
gagggtgaac ggccacattg ggactgagac acggcccaga ctcctacggg aggcagcagt      360
ggggaatatt gcacaatggg ggaaaccctg atgcagcgac gccgcgtgaa ggaagaagta      420
tctcggtatg taaacttcta tcagcaggga agaaaatgac ggtacctgac taagaagccc      480
cggctaacta cgtgccagca gccgcggtaa tacgtagggg gcaagcgtta tccggattta      540
ctgggtgtaa agggagcgta gacggaagag caagtctgat gtgaaaggct ggggcttaac      600
cccaggactg cattggaaac tgttttttctt gagtgccgga gaggtaagcg gaattcctag      660
tgtagcggtg aaatgcgtag atattaggag gaacaccagt ggcgaaggcg gcttactgga      720
cggtaactga cgttgaggct cgaaagcgtg ggagcaaac aggattagat accctggtag      780
tccacgccgt aaacgatgaa tactaggtgt tggggagcaa agctcttcgg tgccgcagca      840
aacgcaataa gtattccacc tggggagtac gttcgcaaga atgaaactca aaggaattga      900
cggggacccg cacaagcggt ggagcatgtg gtttattcga agcaacgcga agaaccttac      960
caagtcttga catcgatctg accggttcgt aatggaacct ttccttcggg acagagaaga     1020
caggtggtgc atggttgtcg tcagctcgtg tcgtgagatg ttgggttaag tcccgcaacg     1080
agcgcaaccc ctatcgtcag tagccagcag gtaaagctgg gcactctgag gagactgcca     1140
```

```
gggataaccct ggaggaaggc ggggacgacg tcaaatcatc atgcccctta tgatttgggc    1200
tacacacgtg ctacaatggc gtaaacaaag ggaagcgagc ccgcgagggg gagcaaatcc    1260
caaaaataac gtcccagttc ggactgcagt ctgcaactcg actgcacgaa gctggaatcg    1320
ctagtaatcg cgaatcagaa tgtcgcggtg aatacgttcc cgggtcttgt acacaccgcc    1380
cgtcacacca tgggagtcag taacgcccga agtcagtgac ccaaccttag ggagggagct    1440
gccgaaggcg ggattgataa ctggggtgaa gtctaggggg t                         1481
```

```
<210> SEQ ID NO 4
<211> LENGTH: 1384
<212> TYPE: DNA
<213> ORGANISM: Artificial Sequence
<220> FEATURE:
<223> OTHER INFORMATION: consensus 16s for Blautia wexlerae
<220> FEATURE:
<221> NAME/KEY: misc_feature
<222> LOCATION: 749
<223> OTHER INFORMATION: 'n' is a, c, g or t
<220> FEATURE:
<221> NAME/KEY: misc_feature
<222> LOCATION: 749
<223> OTHER INFORMATION: 'n' is a, c, g or t

<400> SEQUENCE: 4
```

```
ttcattgaga cttcggtgga tttagattct atttctagtg gcggacgggt gagtaacgcg     60
tgggtaacct gccttataca gggggataac agtcagaaat ggctgctaat accgcataag    120
cgcacagagc tgcatggctc agtgtgaaaa actccggtgg tataagatgg acccgcgttg    180
gattagcttg ttggtgggt  aacggcccac caaggcgacg atccatagcc ggcctgagag    240
ggtgaacggc cacattggga ctgagacacg gcccagactc ctacgggagg cagcagtggg    300
gaatattgca caatggggga aaccctgatg cagcgacgcc gcgtgaagga agaagtatct    360
cggtatgtaa acttctatca gcagggaaga tagtgacggt acctgactaa gaagccccgg    420
ctaactacgt gccagcagcc gcggtaatac gtagggggca agcgttatcc ggatttactg    480
ggtgtaaagg gagcgtagac ggtgtggcaa gtctgatgtg aaaggcatgg gctcaacctg    540
tggactgcat tggaaactgt catacttgag tgccggaggg gtaagcggaa ttcctagtgt    600
agcggtgaaa tgcgtagata ttaggaggaa caccagtggc gaaggcggct tactggacgg    660
taactgacgt tgaggctcga aagcgtgggg agcaaacagg attagatacc ctggtagtcc    720
acgccgtaaa cgatgaatac taggtgtcng gggagcatgg ctcttcggtg ccgtcgcaaa    780
cgcagtaagt attccacctg gggagtacgt tcgcaagaat gaaactcaaa ggaattgacg    840
gggacccgca caagcggtgg agcatgtggt ttaattcgaa gcaacgcgaa gaaccttacc    900
aagtcttgac atccgcctga ccgatcctta accggatctt tccttcggga caggcgagac    960
aggtggtgca tggttgtcgt cagctcgtgt cgtgagatgt tgggttaagt cccgcaacga   1020
gcgcaacccc tatcctcagt agccagcatt taaggtgggc actctgggga gactgccagg   1080
gataacctgg aggaaggcgg ggatgacgtc aaatcatcat gccccttatg atttgggcta   1140
cacacgtgct acaatggcgt aaacaaaggg aagcgagatc gtgagatgga gcaaatccca   1200
aaaataacgt cccagttcgg actgtagtct gcaacccgac tacacgaagc tggaatcgct   1260
agtaatcgcg gatcagaatg ccgcggtgaa tacgttcccg ggtcttgtac acaccgcccg   1320
tcacaccatg ggagtcagta acgcccgaag tcagtgacct aactgcaaag aaggagctgc   1380
cgaa                                                                 1384
```

```
<210> SEQ ID NO 5
<211> LENGTH: 1458
<212> TYPE: DNA
<213> ORGANISM: Blautia hydrogenotrophica
<220> FEATURE:
<221> NAME/KEY: misc_feature
<222> LOCATION: 1416
<223> OTHER INFORMATION: 'n' is a, c, g or t
<220> FEATURE:
<221> NAME/KEY: misc_feature
<222> LOCATION: 1416
<223> OTHER INFORMATION: 'n' is a, c, g or t

<400> SEQUENCE: 5
gatgaacgct ggcggcgtgc ttaacacatg caagtcgaac gaagcgatag agaacggaga      60
tttcggttga agttttctat tgactgagtg gcggacgggt gagtaacgcg tgggtaacct     120
gccctataca gggggataac agttagaaat gactgctaat accgcataag cgcacagctt     180
cgcatgaagc ggtgtgaaaa actgaggtgg tataggatgg acccgcgttg gattagctag     240
ttggtgaggt aacggcccac caaggcgacg atccatagcc ggcctgagag ggtgaacggc     300
cacattggga ctgagacacg gcccaaactc ctacgggagg cagcagtggg gaatattgca     360
caatggggga acccctgatg cagcgacgcc gcgtgaagga agaagtatct cggtatgtaa     420
acttctatca gcagggaaga aagtgacggt acctgactaa gaagccccgg ctaattacgt     480
gccagcagcc gcggtaatac gtaaggggca agcgttatcc ggatttactg ggtgtaaagg     540
gagcgtagac ggtttggcaa gtctgatgtg aaaggcatgg gctcaacctg tggactgcat     600
tggaaactgt cagacttgag tgccggagag gcaagcggaa ttcctagtgt agcggtgaaa     660
tgcgtagata ttaggaggaa caccagtggc gaaggcggcc tgctggacgg taactgacgt     720
tgaggctcga agcgtgggg agcaaacagg attagatacc ctggtagtcc acgctgtaaa     780
cgatgaatac taggtgtcgg gtggcaaagc cattcggtgc cgcagcaaac gcaataagta     840
ttcccacctg gggagtacgt tcgcaagaat gaaactcaaa ggaattgacg ggacccgca      900 caagcggtgg agcatgtggt ttaattcgaa gcaacgcgaa gaaccttacc aaatcttgac     960
atccctctga ccgggaagta atgttccctt ttcttcggaa cagaggagac aggtggtgca    1020
tggttgtcgt cagctcgtgt cgtgagatgt tgggttaagt cccgcaacga gcgcaaccct    1080
tattcttagt agccagcagg tagagctggg cactctaggg agactgccag ggataacctg    1140
gaggaaggtg gggatgacgt caaatcatca tgccccttat gatttgggct acacacgtgc    1200
tacaatggcg taaacaaagg gaagcgaagg ggtgacctgg agcaaatctc aaaaataacg    1260
tctcagttcg gattgtagtc tgcaactcga ctacatgaag ctggaatcgc tagtaatcgc    1320
gaatcagaat gtcgcggtga atacgttccc gggtcttgta cacaccgccc gtcacaccat    1380
gggagtcagt aacgcccgaa gtcagtgacc caaccnaaag gagggagctg ccgaaggtgg    1440
gactgataac tggggtga                                                  1458
```